(12) United States Patent
Banner et al.

(10) Patent No.: US 8,461,160 B2
(45) Date of Patent: Jun. 11, 2013

(54) DIHYDROPYRIMIDINONES

(75) Inventors: David Banner, Basel (CH); Hans Hilpert, Muenchenstein (CH); Roland Humm, Auggen (DE); Harald Mauser, Schliengen (DE); Alexander V. Mayweg, Basel (CH); Fabienne Ricklin, Hombourg (FR); Mark Rogers-Evans, Bottmingen (CH)

(73) Assignee: Hoffmann-La Roche, Inc., Nutley, NJ (US)

( * ) Notice: Subject to any disclaimer, the term of this patent is extended or adjusted under 35 U.S.C. 154(b) by 272 days.

(21) Appl. No.: 12/770,802

(22) Filed: Apr. 30, 2010

(65) Prior Publication Data

US 2010/0286158 A1 Nov. 11, 2010

(30) Foreign Application Priority Data

May 8, 2009 (EP) ..................................... 09159740

(51) Int. Cl.
*C07D 239/22* (2006.01)
*C07D 401/12* (2006.01)
*C07D 403/12* (2006.01)
*A61K 31/513* (2006.01)

(52) U.S. Cl.
USPC .................. 514/252.02; 514/255.05; 514/267; 514/272; 544/230; 544/231; 544/238; 544/295; 544/296; 544/321

(58) Field of Classification Search
USPC .................. 544/230, 231, 238, 295, 296, 321; 514/252.02, 255.05, 267, 272
See application file for complete search history.

(56) References Cited

U.S. PATENT DOCUMENTS

| 2007/0027199 A1 | 2/2007 | Malamas et al. | |
| 2011/0237576 A1* | 9/2011 | Yonezawa et al. | ......... 514/230.5 |

FOREIGN PATENT DOCUMENTS

| WO | 2005014576 | 2/2005 |
| WO | 2006/009653 | 1/2006 |
| WO | 2006005486 | 1/2006 |
| WO | 2006/041404 | 4/2006 |
| WO | 2006/041405 | 4/2006 |
| WO | 2007/049532 | 5/2007 |
| WO | 2008/133273 | 11/2008 |
| WO | 2008/133274 | 11/2008 |
| WO | 2010/047372 | 4/2010 |

OTHER PUBLICATIONS

European Search Report for Appl PCT/EP2010/056055 mailed Aug. 17, 2010.
Prentki et al., Journal of Clinical Investigation, 2006, vol. 116, Issue 7, pp. 1802-1812.
Wild et al., Diabetes Care, 2004, vol. 27, Issue 5, pp. 1047-1053.
Zimmet et al., Nature, 2001, vol. 414 Nr. 6865 pp. 782-787.
Baggio et al., Annual Review of Medicine, 2006, vol. 57 pp. 265-281.
Akpinar et al., Cell Metabolism, 2005, vol. 2, Issue 6, pp. 385-397.
Fukui et al., Cell Metabolism, 2005, vol. 2, Issue 6, pp. 373-384.
Finzi et al., Ultrastruct. Pathol. 2008, vol. 32, Issue 6, pp. 246-251.
Hussain et al., Molecular and Cellular Neuroscience, 2000, vol. 16, Issue 5, pp. 609-619.
Kuhn et al., Journal of Biological Chemistry, 2007, vol. 282 (16) pp. 11982-11995.
Tang et al., J. Org. Chem. 1999, vol. 64 p. 12.
Gronowitz et al., Acta Chemica Scandinavica, 1975 B29(2) p. 233.
Frohn et al., Bioorganic and Medicinal Chemistry Letters, 2008 vol. 18, Issue 18 p. 5023.
Blank et al., Journal of Medicinal Chemistry 1974, vol. 17, Issue 10 p. 1065.
Ostermann et al., Journal of Molecular Biology 2006, vol. 355 Issue 2 pp. 249-261.

* cited by examiner

*Primary Examiner* — Deepak Rao

(57) ABSTRACT

This invention relates to dihydropyrimidinones of the formula

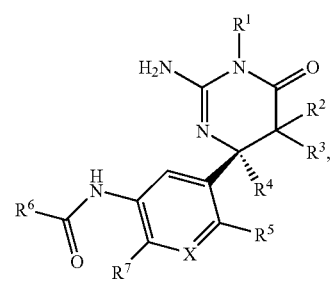

wherein X and $R^1$ to $R^7$ are as defined in the description, as well as pharmaceutically acceptable salts thereof. These compounds are BACE2 inhibitors and can be used as medicaments for the treatment or prevention of diseases such as diabetes.

20 Claims, No Drawings

DIHYDROPYRIMIDINONES

PRIORITY TO RELATED APPLICATION(S)

This application claims the benefit of European Patent Application No. 09159740.1, filed May 8, 2009, which is hereby incorporated by reference in its entirety.

FIELD OF THE INVENTION

The present invention relates to compounds which inhibit BACE2. The compounds are useful for the treatment and prevention of diabetes, particularly type 2 diabetes, metabolic syndrome, hypertension and a wide range of metabolic disorders.

Type 2 diabetes (T2D) is caused by insulin resistance and inadequate insulin secretion from pancreatic beta-cells leading to poor blood-glucose control and hyperglycemia (M Prentki & C J Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000 an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053) making the disease a major healthcare problem. The rise in prevalence of T2D is associated with an increasingly sedentary lifestyle and high-energy food intake of the world's population (P Zimmet, K G M M Alberti & J Shaw, "Global and societal implications of the diabetes epidemic" Nature 2001, 414, 782-787).

Beta-cell failure and consequent dramatic decline in insulin secretion and hyperglycemia marks the onset of T2D (M Prentki & C J Nolan, "Islet beta-cell failure in type 2 diabetes." J. Clin. Investig. 2006, 116(7), 1802-1812). Most current treatments do not prevent the loss of beta-cell mass characterising overt T2D. However, recent developments with GLP-1 analogues, gastrin and other agents show that preservation and proliferation of beta-cells is possible to achieve, leading to an improved glucose tolerance and slower progression to overt T2D (L L Baggio & D J Drucker, "Therapeutic approaches to preserve islet mass in type 2 diabetes", Annu Rev. Med. 2006, 57, 265-281).

Tmem27 has been identified as a protein promoting beta-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of beta-cells, resulting from a degradation of the full-length cellular Tmem27. Overexpression of Tmem27 in a transgenic mouse increases beta-cell mass and improves glucose tolerance in a DIO model of diabetes [K Fukui, Q Yang, Y Cao, N Takahashi et al., "The HNF-1 target Collectrin controls insulin exocytosis by SNARE complex formation", Cell Metab. 2005, 2, 373-384, P Akpinar, S Kuwajima, J Krützfeldt, M Stoffel, "Tmem27: A cleaved and shed plasma membrane protein that stimulates pancreatic (3 cell proliferation", Cell Metab. 2005, 2, 385-397). Furthermore, siRNA knockout of Tmem27 in a rodent beta-cell proliferation assay (eg using INS1e cells) reduces the proliferation rate, indicating a role for Tmem27 in control of beta-cell mass.

In vitro, BACE2 cleaves a peptide based on the sequence of Tmem27. The closely related protease BACE1 does not cleave this peptide and selective inhibition of BACE1 alone does not enhance proliferation of beta-cells. BACE1 (BACE for beta-site APP-cleaving enzyme, also known as beta-secretase) has been implicated in the pathogenesis of Alzheimer disease and in the formation of myelin sheaths in peripheral nerve cells.

The close homolog BACE2 is a membrane-bound aspartyl protease and is colocalised with Tmem27 in rodent pancreatic beta-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995).

Inhibition of BACE2 is therefore proposed as a treatment for T2D with the potential to preserve and restore beta-cell mass and stimulate insulin secretion in pre-diabetic and diabetic patients. It is therefore an object of the present invention to provide selective BACE2 inhibitors. Such compounds are useful as therapeutically active substances, particularly in the treatment and/or prevention of diseases which are associated with the inhibition of BACE2.

The compounds of the present invention exceed the compounds known in the art, inasmuch as they are strong inhibitors of BACE2 and show less penetration into the brain than known BACE1 inhibitors (BACE1 is localized in the brain, BACE2 in the pancreas). They are expected to have an enhanced therapeutic potential compared to the compounds already known in the art and can be used for the treatment and prevention of diabetes, preferably type 2 diabetes, metabolic syndrome, hypertension and a wide range of metabolic disorders.

SUMMARY OF THE INVENTION

The present invention relates to dihydropyrimidinones of the formula

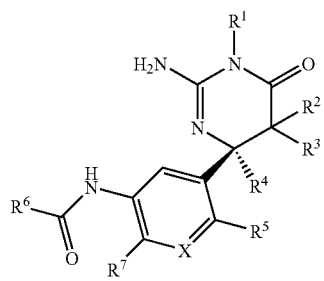

wherein
X is CH or N;
R¹ is selected from the group consisting of hydrogen, $C_{1-7}$-alkyl, $C_{3-7}$-cycloalkyl-$C_{1-7}$-alkyl and benzyl;
R² is hydrogen or $C_{1-7}$-alkyl;

$R^3$ is selected from the group consisting of hydrogen, $C_{1-7}$-alkyl, hydroxy and benzyloxy;

or $R^2$ and $R^3$, together with the C atom to which they are attached, form a $C_{3-7}$-cycloalkyl ring;

$R^4$ is $C_{1-7}$-alkyl or $C_{3-7}$-cycloalkyl;

$R^5$ is selected from the group consisting of hydrogen, $C_{1-7}$-alkyl, halogen, cyano and $C_{1-7}$-alkoxy;

or $R^4$ and $R^5$ together are —$(CH_2)_n$— with n being 2 or 3 and thus form a ring;

$R^6$ is aryl or heteroaryl, said aryl or heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo, $C_{3-7}$-cycloalkyl, imidazolyl, phenylsulfanyl and phenyl, said phenyl being unsubstituted or substituted by halogen; and $R^7$ is hydrogen or halogen;

or a pharmaceutically acceptable salt thereof.

The invention also relates to pharmaceutical compositions comprising a compound as described above and a pharmaceutically acceptable carrier and/or adjuvant.

The invention is also concerned with the manufacture of compounds of formula I.

A further aspect of the invention is a method for the treatment of a disease associated with the inhibition of BACE2 activity comprising administering a therapeutically-active amount of the aforementioned compound.

DETAILED DESCRIPTION OF THE INVENTION

Definitions

Unless otherwise indicated, the following definitions are set forth to illustrate and define the meaning and scope of the various terms used to describe the invention.

The term "halogen" refers to fluorine, chlorine, bromine and iodine, with fluorine, chlorine and bromine being preferred, and with fluorine and chlorine being more preferred.

The term "lower alkyl" or "$C_{1-7}$-alkyl", alone or in combination, signifies a straight-chain or branched-chain alkyl group with 1 to 7 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_{1-7}$ alkyl groups are methyl, ethyl, propyl, isopropyl, butyl, isobutyl, tert.-butyl, the isomeric pentyls, the isomeric hexyls and the isomeric heptyls, preferably methyl and ethyl and most preferred methyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert.-butoxy, preferably methoxy and ethoxy.

The term "benzyloxy" refers to the group R—O—, wherein R is a benzyl group.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclopropyl, cyclobutyl and cyclopentyl.

The term "lower halogenalkyl" or "halogen-$C_{1-7}$-alkyl" refers to lower alkyl groups as defined above wherein at least one of the hydrogen atoms of the lower alkyl group is replaced by a halogen atom, preferably fluoro or chloro, most preferably fluoro. Among the preferred lower halogenalkyl groups are trifluoromethyl, difluoromethyl, trifluoroethyl, 2,2-difluoroethyl, fluoromethyl and chloromethyl, with trifluoromethyl or difluoromethyl being especially preferred.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkoxy groups are trifluoromethoxy, difluoromethoxy, fluoromethoxy and chloromethoxy, with trifluoromethoxy being especially preferred.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the preferred lower hydroxyalkyl groups are hydroxymethyl or hydroxyethyl.

The term "oxo" means the group "=O" bound to a ring atom.

The term "aryl" refers to an aromatic monocyclic or multicyclic ring system having 6 to 14 carbon atoms, preferably 6 to 10 carbon atoms. Preferred aryl groups are phenyl and naphthyl, with phenyl being most preferred.

The term "heteroaryl" refers to an aromatic or partly unsaturated 5- or 6-membered ring which comprises at least one heteroatom selected from nitrogen, oxygen and/or sulphur, and can in addition comprise one or three atoms selected from nitrogen, oxygen and/or sulphur, such as pyridyl, pyrazinyl, pyrimidinyl, pyridazinyl, 6-oxo-1,6-dihydropyridazinyl, 5-oxo-4,5-dihydropyrazinyl, pyrrolyl, furyl, thienyl, oxazolyl, isoxazolyl, oxadiazolyl, thiadiazolyl, tetrazolyl, pyrazolyl, imidazolyl, triazolyl and thiazolyl. The term "heteroaryl" further refers to bicyclic aromatic or partly unsaturated groups comprising two 5- or 6-membered rings, in which one or both rings can contain one, two or three atoms selected from nitrogen, oxygen or sulphur, such as quinolinyl, isoquinolinyl, cinnolinyl, pyrazolo[1,5-a]pyridyl, imidazo[1,2-a]pyridyl, pyrrolo[2,3-b]pyridinyl, thieno[3,2-b]pyridyl, thieno[2,3-c]pyridyl, quinoxalinyl, benzo[b]thienyl, benzothiazolyl, benzotriazolyl, indolyl, indazolyl and 3,4-dihydro-1H-isoquinolinyl. Preferred heteroaryl groups are thienyl, oxazolyl, isoxazolyl, thiazolyl, pyrazolyl, imidazolyl, pyridyl, pyrimidinyl, pyrazinyl, 6-oxo-1,6-dihydropyridazinyl, 5-oxo-4,5-dihydropyrazinyl, imidazo[1,2-a]pyridyl, benzo[b]thienyl, pyrrolo[2,3-b]pyridinyl, thieno[3,2-b]pyridyl, thieno[2,3-c]pyridyl, quinolinyl and isoquinolinyl, with thienyl, oxazolyl, pyridyl, pyrimidinyl and pyrazinyl being more preferred and pyridyl being most preferred.

The term "phenylsulfanyl" refers to the group R"—S— wherein R" is phenyl.

Compounds of formula I can form pharmaceutically acceptable salts. The term "pharmaceutically acceptable salts" refers to those salts which retain the biological effectiveness and properties of the free bases or free acids, which are not biologically or otherwise undesirable. Preferably, the pharmaceutically acceptable salts of the compounds of formula I are the acid addition salts with physiologically compatible mineral acids, such as hydrochloric acid, sulfuric acid, sulfurous acid or phosphoric acid; or with organic acids, such as methanesulfonic acid, ethanesulfonic acid, p-toluenesulfonic acid, formic acid, acetic acid, propionic acid, glycolic acid, pyruvic acid, oxylic acid, lactic acid, trifluoroacetic acid, citric acid, fumaric acid, maleic acid, malonic acid, tartaric acid, benzoic acid, cinnamic acid, mandelic acid, succinic acid or salicylic acid. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. The compound of formula I can also be present in the form of zwitterions. Particularly preferred pharmaceutically acceptable salts of compounds of formula I are the acid addition salts such as the hydrochloride salts, the formate salts or trifluoroacetate salts.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four non-identical substituents is termed a "chiral center".

Inhibitors of BACE2

In detail, the present invention relates to compounds of the formula

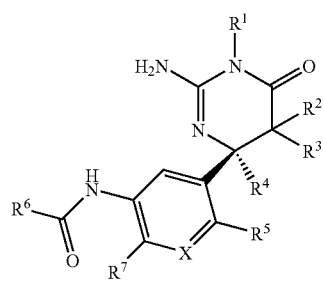

I wherein
X is CH or N;
$R^1$ is selected from the group consisting of hydrogen, $C_{1-7}$-alkyl, $C_{3-7}$-cycloalkyl-$C_{1-7}$-alkyl and benzyl;
$R^2$ is hydrogen or $C_{1-7}$-alkyl;
$R^3$ is selected from the group consisting of hydrogen, $C_{1-7}$-alkyl, hydroxy and benzyloxy;
or $R^2$ and $R^3$, together with the C atom to which they are attached, form a $C_{3-7}$-cycloalkyl ring;
$R^4$ is $C_{1-7}$-alkyl or $C_{3-7}$-cycloalkyl;
$R^5$ is selected from the group consisting of hydrogen, $C_{1-7}$-alkyl, halogen, cyano and $C_{1-7}$-alkoxy;
or $R^4$ and $R^5$ together are —$(CH_2)_n$— with n being 2 or 3 and thus form a ring;
$R^6$ is aryl or heteroaryl, said aryl or heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo, $C_{3-7}$-cycloalkyl, imidazolyl, phenylsulfanyl and phenyl, said phenyl being unsubstituted or substituted by halogen; and
$R^7$ is hydrogen or halogen;
or a pharmaceutically acceptable salt thereof.

Preferred compounds of formula I according to the present invention are those, wherein X is CH. These are the compounds of the formula

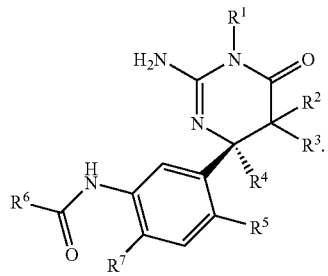

I-A

Furthermore, compounds of formula I wherein X is N are also preferred. These are the compounds of the formula

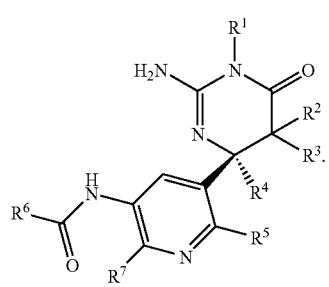

I-B

Especially preferred are those compounds of formula I, wherein $R^1$ is $C_{1-7}$-alkyl, with those compounds wherein $R^1$ is methyl being most preferred.

In addition, compounds of formula I wherein $R^1$ is hydrogen are preferred.

Compounds of formula I wherein $R^1$ is benzyl are further preferred.

Furthermore, preferred compounds of formula I according to the invention are those wherein $R^2$ and $R^3$, independently from each other, are selected from hydrogen or $C_{1-7}$-alkyl. Compounds of formula I wherein $R^2$ and $R^3$ are hydrogen are especially preferred. Also preferred are compounds of formula I wherein $R^2$ and $R^3$ are methyl. Further preferred are compounds of formula I wherein $R^2$ is hydrogen and $R^3$ is selected from the group consisting of methyl, ethyl, hydroxy or benzyloxy.

Preferably, $R^4$ signifies $C_{1-7}$-alkyl or $C_{3-7}$-cycloalkyl. Compounds of formula I of the present invention wherein $R^4$ is $C_{1-7}$-alkyl are preferred, with $R^4$ being methyl or ethyl being more preferred.

Furthermore, compounds of formula I according to the invention wherein $R^5$ is hydrogen or halogen are preferred. More preferably, $R^5$ is hydrogen or fluoro. Especially preferred are compounds of formula I wherein $R^5$ is fluoro. Also preferred are compounds of formula I wherein $R^5$ is hydrogen.

In addition, compounds of formula I wherein $R^4$ and $R^5$ together are —$(CH_2)_n$— with n being 2 or 3 thus forming a ring are preferred. Preferred are those, wherein n is 2, thus having the formula

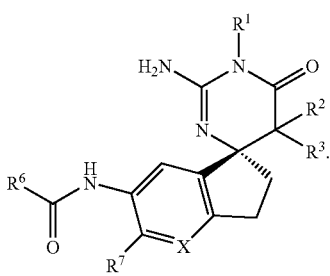

I-C

Furthermore, compounds of formula I of the present invention wherein $R^6$ is heteroaryl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo, $C_{3-7}$-cycloalkyl, imidazolyl, phenylsulfanyl and phenyl, said phenyl being unsubstituted or substituted by halogen are preferred.

Compounds of formula I of the present invention wherein $R^6$ is heteroaryl selected from the group consisting of thienyl, oxazolyl, isoxazolyl, thiazolyl, pyrazolyl, imidazolyl, pyridyl, pyrimidinyl, pyrazinyl, 6-oxo-1,6-dihydropyridazinyl, 5-oxo-4,5-dihydropyrazinyl, imidazo[1,2-a]pyridyl, benzo[b]thienyl, pyrrolo[2,3-b]pyridinyl, thieno[3,2-b]pyridyl, thieno[2,3-c]pyridyl, quinolinyl and isoquinolinyl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo, $C_{3-7}$-cycloalkyl, imidazolyl, phenylsulfanyl and phenyl, said phenyl being unsubstituted or substituted by halogen, are particularly preferred.

Preferably, compounds of formula I according to the invention are those wherein $R^6$ is heteroaryl selected from the group consisting of pyridyl, pyrazinyl, pyrimidinyl, pyridazinyl, 6-oxo-1,6-dihydropyridazinyl, 5-oxo-4,5-dihydropyrazinyl, pyrrolyl, furyl, thienyl, oxazolyl, isoxazolyl, oxadiazolyl, thiadiazolyl, tetrazolyl, pyrazolyl, imidazolyl, triazolyl, thiazolyl, quinolinyl, isoquinolinyl, cinnolinyl, pyrazolo[1,5-a]pyridyl, imidazo[1,2-a]pyridyl, quinoxalinyl, benzothiazolyl, benzotriazolyl, indolyl, indazolyl and 3,4-dihydro-1H-isoquinolinyl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

More preferably, $R^6$ is heteroaryl selected from the group consisting of thienyl, oxazolyl, pyrazolyl, pyridyl, pyrimidinyl and pyrazinyl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo, $C_{3-7}$-cycloalkyl, imidazolyl, phenylsulfanyl and phenyl, said phenyl being unsubstituted or substituted by halogen.

Most preferably, $R^6$ is pyridyl, said pyridyl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo, $C_{3-7}$-cycloalkyl, imidazolyl, phenylsulfanyl and phenyl, said phenyl being unsubstituted or substituted by halogen. More preferably, $R^6$ is pyridyl substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl, with pyridyl being substituted by halogen being most preferred.

Also preferred are compounds of formula I according to the invention wherein $R^6$ is phenyl, said phenyl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo, $C_{3-7}$-cycloalkyl, imidazolyl, phenylsulfanyl and phenyl, said phenyl being unsubstituted or substituted by halogen. Particularly preferred are compounds of formula I, wherein $R^6$ is phenyl, said phenyl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

A particular group of compounds of the present invention are those of the following formula

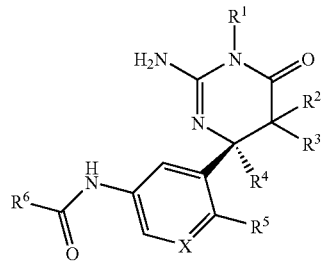

I-D wherein
X is CH or N;
$R^1$ is selected from the group consisting of hydrogen, $C_{1-7}$-alkyl and benzyl;
$R^2$ is hydrogen or $C_{1-7}$-alkyl;
$R^3$ is hydrogen or $C_{1-7}$-alkyl;
or $R^2$ and $R^3$, together with the C atom to which they are attached, form a $C_{3-7}$-cycloalkyl ring;
$R^4$ is $C_{1-7}$-alkyl or $C_{3-7}$-cycloalkyl;
$R^5$ is selected from the group consisting of hydrogen, $C_{1-7}$-alkyl, halogen, cyano and $C_{1-7}$-alkoxy; and
$R^6$ is aryl or heteroaryl, said aryl or heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl;
or a pharmaceutically acceptable salt thereof.

Examples of compounds of formula I of the present invention are the following:
(5-methyl-thiophene-2-carboxylic acid [3-((S)-2-amino-1,4-dimethyl-6-oxo-1,4,5,6-tetrahydro-pyrimidin-4-yl)-phenyl]-amide,
5-chloro-thiophene-2-carboxylic acid [3-((S)-2-amino-1,4-dimethyl-6-oxo-1,4,5,6-tetrahydro-pyrimidin-4-yl)-phenyl]-amide,
2,5-dimethyl-thiophene-3-carboxylic acid [3-((S)-2-amino-1,4-dimethyl-6-oxo-1,4,5,6-tetrahydro-pyrimidin-4-yl)-phenyl]-amide,
2,5-dimethyl-oxazole-4-carboxylic acid [3-((S)-2-amino-1,4-dimethyl-6-oxo-1,4,5,6-tetrahydro-pyrimidin-4-yl)-phenyl]-amide,
2,4-dimethyl-oxazole-5-carboxylic acid [3-((S)-2-amino-1,4-dimethyl-6-oxo-1,4,5,6-tetrahydro-pyrimidin-4-yl)-phenyl]-amide, 3-methyl-isoxazole-5-carboxylic acid [3-((S)-2-amino-1,4-dimethyl-6-oxo-1,4,5,6-tetrahydro-pyrimidin-4-yl)-phenyl]-amide,
1,5-dimethyl-1H-pyrazole-3-carboxylic acid [3-((S)-2-amino-1,4-dimethyl-6-oxo-1,4,5,6-tetrahydro-pyrimidin-4-yl)-phenyl]-amide,
2,5-dimethyl-2H-pyrazole-3-carboxylic acid [3-((S)-2-amino-1,4-dimethyl-6-oxo-1,4,5,6-tetrahydro-pyrimidin-4-yl)-phenyl]-amide,
imidazo[1,2-a]pyridine-2-carboxylic acid [3-((S)-2-amino-1,4-dimethyl-6-oxo-1,4,5,6-tetrahydro-pyrimidin-4-yl)-phenyl]-amide,
5-chloro-pyridine-2-carboxylic acid [3-((S)-2-amino-1,4-dimethyl-6-oxo-1,4,5,6-tetrahydro-pyrimidin-4-yl)-phenyl]-amide,
5-trifluoromethyl-pyridine-2-carboxylic acid [3-((S)-2-amino-1,4-dimethyl-6-oxo-1,4,5,6-tetrahydro-pyrimidin-4-yl)-phenyl]-amide,
5-methyl-pyridine-2-carboxylic acid [3-((S)-2-amino-1,4-dimethyl-6-oxo-1,4,5,6-tetrahydro-pyrimidin-4-yl)-phenyl]-amide,
pyridine-2-carboxylic acid [3-((S)-2-amino-1,4-dimethyl-6-oxo-1,4,5,6-tetrahydro-pyrimidin-4-yl)-phenyl]-amide,
5-methoxy-pyridine-2-carboxylic acid [3-((S)-2-amino-1,4-dimethyl-6-oxo-1,4,5,6-tetrahydro-pyrimidin-4-yl)-phenyl]-amide,
5-cyano-pyridine-2-carboxylic acid [3-((S)-2-amino-1,4-dimethyl-6-oxo-1,4,5,6-tetrahydro-pyrimidin-4-yl)-phenyl]-amide,
5-hydroxymethyl-pyridine-2-carboxylic acid [3-((S)-2-amino-1,4-dimethyl-6-oxo-1,4,5,6-tetrahydro-pyrimidin-4-yl)-phenyl]-amide,
N-[3-((S)-2-amino-1,4-dimethyl-6-oxo-1,4,5,6-tetrahydro-pyrimidin-4-yl)-phenyl]-4-methyl-benzamide,
N-[3-((S)-2-amino-1,4-dimethyl-6-oxo-1,4,5,6-tetrahydro-pyrimidin-4-yl)-phenyl]-4-chloro-benzamide,
N-[3-((S)-2-amino-1,4-dimethyl-6-oxo-1,4,5,6-tetrahydro-pyrimidin-4-yl)-phenyl]-6-chloro-nicotinamide,
5-chloro-pyrimidine-2-carboxylic acid [3-((S)-2-amino-1,4-dimethyl-6-oxo-1,4,5,6-tetrahydro-pyrimidin-4-yl)-phenyl]-amide,
1-methyl-6-oxo-1,6-dihydro-pyridazine-3-carboxylic acid [3-((S)-2-amino-1,4-dimethyl-6-oxo-1,4,5,6-tetrahydro-pyrimidin-4-yl)-phenyl]-amide,
5-methyl-pyrazine-2-carboxylic acid [3-((S)-2-amino-1,4-dimethyl-6-oxo-1,4,5,6-tetrahydro-pyrimidin-4-yl)-phenyl]-amide,
6-oxo-1,6-dihydro-pyridazine-3-carboxylic acid [3-((S)-2-amino-1,4-dimethyl-6-oxo-1,4,5,6-tetrahydro-pyrimidin-4-yl)-phenyl]-amide,
6-methyl-pyrazine-2-carboxylic acid [3-((S)-2-amino-1,4-dimethyl-6-oxo-1,4,5,6-tetrahydro-pyrimidin-4-yl)-phenyl]-amide,
5-chloro-pyrazine-2-carboxylic acid [3-((S)-2-amino-1,4-dimethyl-6-oxo-1,4,5,6-tetrahydro-pyrimidin-4-yl)-phenyl]-amide,
N-[3-((S)-2-amino-1,4-dimethyl-6-oxo-1,4,5,6-tetrahydro-pyrimidin-4-yl)-phenyl]-isonicotinamide,
5-fluoro-pyridine-2-carboxylic acid [3-((S)-2-amino-1,4-dimethyl-6-oxo-1,4,5,6-tetrahydro-pyrimidin-4-yl)-phenyl]-amide,
3-chloro-pyridine-2-carboxylic acid [3-((S)-2-amino-1,4-dimethyl-6-oxo-1,4,5,6-tetrahydro-pyrimidin-4-yl)-phenyl]-amide,
4-chloro-pyridine-2-carboxylic acid [3-((S)-2-amino-1,4-dimethyl-6-oxo-1,4,5,6-tetrahydro-pyrimidin-4-yl)-phenyl]-amide,
4-methyl-pyridine-2-carboxylic acid [3-((S)-2-amino-1,4-dimethyl-6-oxo-1,4,5,6-tetrahydro-pyrimidin-4-yl)-phenyl]-amide,
6-chloro-pyridine-2-carboxylic acid [3-((S)-2-amino-1,4-dimethyl-6-oxo-1,4,5,6-tetrahydro-pyrimidin-4-yl)-phenyl]-amide,
6-methyl-pyridine-2-carboxylic acid [3-((S)-2-amino-1,4-dimethyl-6-oxo-1,4,5,6-tetrahydro-pyrimidin-4-yl)-phenyl]-amide,
N-[3-((S)-2-amino-1,4-dimethyl-6-oxo-1,4,5,6-tetrahydro-pyrimidin-4-yl)-phenyl]-nicotinamide,
N-[3-((S)-2-amino-1,4-dimethyl-6-oxo-1,4,5,6-tetrahydro-pyrimidin-4-yl)-phenyl]-benzamide; salt with formic acid,
2-methyl-pyrimidine-5-carboxylic acid [3-((S)-2-amino-1,4-dimethyl-6-oxo-1,4,5,6-tetrahydro-pyrimidin-4-yl)-phenyl]-amide,
5-oxo-4,5-dihydro-pyrazine-2-carboxylic acid [3-((S)-2-amino-1,4-dimethyl-6-oxo-1,4,5,6-tetrahydro-pyrimidin-4-yl)-phenyl]-amide,
3-phenyl-pyridine-2-carboxylic acid [3-((S)-2-amino-1,4-dimethyl-6-oxo-1,4,5,6-tetrahydro-pyrimidin-4-yl)-phenyl]-amide,
2-methyl-oxazole-4-carboxylic acid [3-((S)-2-amino-1,4-dimethyl-6-oxo-1,4,5,6-tetrahydro-pyrimidin-4-yl)-phenyl]-amide,
5-chloro-pyridine-2-carboxylic acid [3-((S)-2-amino-4-ethyl-1-methyl-6-oxo-1,4,5,6-tetrahydro-pyrimidin-4-yl)-phenyl]-amide,
pyridine-2-carboxylic acid [3-((S)-2-amino-4-ethyl-1-methyl-6-oxo-1,4,5,6-tetrahydro-pyrimidin-4-yl)-phenyl]-amide,
5-chloro-thiophene-2-carboxylic acid [3-((S)-2-amino-4-ethyl-1-methyl-6-oxo-1,4,5,6-tetrahydro-pyrimidin-4-yl)-phenyl]-amide,
6-chloro-pyridine-2-carboxylic acid [3-((S)-2-amino-4-ethyl-1-methyl-6-oxo-1,4,5,6-tetrahydro-pyrimidin-4-yl)-phenyl]-amide,
3-chloro-pyridine-2-carboxylic acid [3-((S)-2-amino-4-ethyl-1-methyl-6-oxo-1,4,5,6-tetrahydro-pyrimidin-4-yl)-phenyl]-amide,
5-chloro-pyrimidine-2-carboxylic acid [3-((S)-2-amino-4-ethyl-1-methyl-6-oxo-1,4,5,6-tetrahydro-pyrimidin-4-yl)-phenyl]-amide,
5-chloro-pyridine-2-carboxylic acid [3-((S)-2-amino-1,4-dimethyl-6-oxo-1,4,5,6-tetrahydro-pyrimidin-4-yl)-4-fluoro-phenyl]-amide,
5-chloro-pyrimidine-2-carboxylic acid [3-((S)-2-amino-1,4-dimethyl-6-oxo-1,4,5,6-tetrahydro-pyrimidin-4-yl)-4-fluoro-phenyl]-amide,
pyridine-2-carboxylic acid [3-((S)-2-amino-1,4-dimethyl-6-oxo-1,4,5,6-tetrahydro-pyrimidin-4-yl)-4-fluoro-phenyl]-amide,
5-trifluoromethyl-pyridine-2-carboxylic acid [3-((S)-2-amino-1,4-dimethyl-6-oxo-1,4,5,6-tetrahydro-pyrimidin-4-yl)-4-fluoro-phenyl]-amide,
5-chloro-pyridine-2-carboxylic acid [3-((S)-2-amino-1-ethyl-4-methyl-6-oxo-1,4,5,6-tetrahydro-pyrimidin-4-yl)-phenyl]-amide,
5-chloro-pyridine-2-carboxylic acid [3-((S)-2-amino-1-benzyl-4-methyl-6-oxo-1,4,5,6-tetrahydro-pyrimidin-4-yl)-phenyl]-amide,
5-chloro-pyridine-2-carboxylic acid [3-((S)-2-amino-4-methyl-6-oxo-1,4,5,6-tetrahydro-pyrimidin-4-yl)-phenyl]-amide,
5-chloro-pyridine-2-carboxylic acid [5-((S)-2-amino-1,4-dimethyl-6-oxo-1,4,5,6-tetrahydro-pyrimidin-4-yl)-pyridin-3-yl]-amide, 5-chloro-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
3,6-dichloro-pyridine-2-carboxylic acid [3-((S)-2-amino-1,4-dimethyl-6-oxo-1,4,5,6-tetrahydro-pyrimidin-4-yl)-phenyl]-amide,
3-propoxy-pyridine-2-carboxylic acid [3-((S)-2-amino-1,4-dimethyl-6-oxo-1,4,5,6-tetrahydro-pyrimidin-4-yl)-phenyl]-amide,
isoquinoline-1-carboxylic acid [3-((S)-2-amino-1,4-dimethyl-6-oxo-1,4,5,6-tetrahydro-pyrimidin-4-yl)-phenyl]-amide,
isoquinoline-3-carboxylic acid [3-((S)-2-amino-1,4-dimethyl-6-oxo-1,4,5,6-tetrahydro-pyrimidin-4-yl)-phenyl]-amide,
quinoline-2-carboxylic acid [3-((S)-2-amino-1,4-dimethyl-6-oxo-1,4,5,6-tetrahydro-pyrimidin-4-yl)-phenyl]-amide,
thieno[3,2-b]pyridine-5-carboxylic acid [3-((S)-2-amino-1,4-dimethyl-6-oxo-1,4,5,6-tetrahydro-pyrimidin-4-yl)-phenyl]-amide,
thieno[2,3-c]pyridine-7-carboxylic acid [3-((S)-2-amino-1,4-dimethyl-6-oxo-1,4,5,6-tetrahydro-pyrimidin-4-yl)-phenyl]-amide,
3-phenylsulfanyl-pyridine-2-carboxylic acid [3-((S)-2-amino-1,4-dimethyl-6-oxo-1,4,5,6-tetrahydro-pyrimidin-4-yl)-phenyl]-amide,
3-trifluoromethyl-pyridine-2-carboxylic acid [3-((S)-2-amino-1,4-dimethyl-6-oxo-1,4,5,6-tetrahydro-pyrimidin-4-yl)-phenyl]-amide,
5-(2,2,2-trifluoro-ethoxy)-pyridine-2-carboxylic acid [3-((S)-2-amino-1,4-dimethyl-6-oxo-1,4,5,6-tetrahydro-pyrimidin-4-yl)-phenyl]-amide,
3,5-dichloro-pyridine-2-carboxylic acid [3-((S)-2-amino-1,4-dimethyl-6-oxo-1,4,5,6-tetrahydro-pyrimidin-4-yl)-phenyl]-amide,
3-methoxy-pyridine-2-carboxylic acid [3-((S)-2-amino-1,4-dimethyl-6-oxo-1,4,5,6-tetrahydro-pyrimidin-4-yl)-phenyl]-amide,
2-trifluoromethyl-thiazole-4-carboxylic acid [3-((S)-2-amino-1,4-dimethyl-6-oxo-1,4,5,6-tetrahydro-pyrimidin-4-yl)-phenyl]-amide,
2-methyl-thiazole-4-carboxylic acid [3-((S)-2-amino-1,4-dimethyl-6-oxo-1,4,5,6-tetrahydro-pyrimidin-4-yl)-phenyl]-amide,
benzo[b]thiophene-2-carboxylic acid [3-((S)-2-amino-1,4-dimethyl-6-oxo-1,4,5,6-tetrahydro-pyrimidin-4-yl)-phenyl]-amide,
1-methyl-1H-pyrazole-3-carboxylic acid [3-((S)-2-amino-1,4-dimethyl-6-oxo-1,4,5,6-tetrahydro-pyrimidin-4-yl)-phenyl]-amide,
3-chloro-5-trifluoromethyl-pyridine-2-carboxylic acid [3-((S)-2-amino-1,4-dimethyl-6-oxo-1,4,5,6-tetrahydro-pyrimidin-4-yl)-phenyl]-amide,
2-phenyl-oxazole-4-carboxylic acid [3-((S)-2-amino-1,4-dimethyl-6-oxo-1,4,5,6-tetrahydro-pyrimidin-4-yl)-phenyl]-amide,
6-chloro-3-trifluoromethyl-pyridine-2-carboxylic acid [3-((S)-2-amino-1,4-dimethyl-6-oxo-1,4,5,6-tetrahydro-pyrimidin-4-yl)-phenyl]-amide,
1-(2,2,2-trifluoro-ethyl)-1H-pyrazole-3-carboxylic acid [3-((S)-2-amino-1,4-dimethyl-6-oxo-1,4,5,6-tetrahydro-pyrimidin-4-yl)-phenyl]-amide,
3-ethoxy-5-trifluoromethyl-pyridine-2-carboxylic acid [3-((S)-2-amino-1,4-dimethyl-6-oxo-1,4,5,6-tetrahydro-pyrimidin-4-yl)-phenyl]-amide,
5-chloro-3-methyl-pyridine-2-carboxylic acid [3-((S)-2-amino-1,4-dimethyl-6-oxo-1,4,5,6-tetrahydro-pyrimidin-4-yl)-phenyl]-amide,
5-(3-trifluoromethyl-pyrazol-1-yl)-pyridine-2-carboxylic acid [3-((S)-2-amino-1,4-dimethyl-6-oxo-1,4,5,6-tetrahydro-pyrimidin-4-yl)-phenyl]-amide,
1,3-dimethyl-1H-pyrazole-4-carboxylic acid [3-((S)-2-amino-1,4-dimethyl-6-oxo-1,4,5,6-tetrahydro-pyrimidin-4-yl)-phenyl]-amide,
1H-pyrrolo[2,3-b]pyridine-2-carboxylic acid [3-((S)-2-amino-1,4-dimethyl-6-oxo-1,4,5,6-tetrahydro-pyrimidin-4-yl)-phenyl]-amide,
2-cyclopropyl-5-methyl-2H-pyrazole-3-carboxylic acid [3-((S)-2-amino-1,4-dimethyl-6-oxo-1,4,5,6-tetrahydro-pyrimidin-4-yl)-phenyl]-amide,
N-[3-((S)-2-amino-1,4-dimethyl-6-oxo-1,4,5,6-tetrahydro-pyrimidin-4-yl)-phenyl]-2-(1H-imidazol-2-yl)-benzamide,
isoxazole-3-carboxylic acid [3-((S)-2-amino-1,4-dimethyl-6-oxo-1,4,5,6-tetrahydro-pyrimidin-4-yl)-phenyl]-amide,
5-methyl-isoxazole-3-carboxylic acid [3-((S)-2-amino-1,4-dimethyl-6-oxo-1,4,5,6-tetrahydro-pyrimidin-4-yl)-phenyl]-amide,
5-ethyl-pyridine-2-carboxylic acid [3-((S)-2-amino-1,4-dimethyl-6-oxo-1,4,5,6-tetrahydro-pyrimidin-4-yl)-phenyl]-amide,
4-methyl-1H-imidazole-2-carboxylic acid [3-((S)-2-amino-1,4-dimethyl-6-oxo-1,4,5,6-tetrahydro-pyrimidin-4-yl)-phenyl]-amide,
5-fluoro-pyridine-2-carboxylic acid [3-((S)-2-amino-4-ethyl-1-methyl-6-oxo-1,4,5,6-tetrahydro-pyrimidin-4-yl)-phenyl]-amide,
5-trifluoromethyl-pyridine-2-carboxylic acid [3-((S)-2-amino-4-ethyl-1-methyl-6-oxo-1,4,5,6-tetrahydro-pyrimidin-4-yl)-phenyl]-amide,
5-chloro-pyridine-2-carboxylic acid [3-((S)-2-amino-1-methyl-6-oxo-4-propyl-1,4,5,6-tetrahydro-pyrimidin-4-yl)-phenyl]-amide,
pyridine-2-carboxylic acid [3-((S)-2-amino-1-methyl-6-oxo-4-propyl-1,4,5,6-tetrahydro-pyrimidin-4-yl)-phenyl]-amide,
1-methyl-1H-pyrazole-3-carboxylic acid [3-((S)-2-amino-1-methyl-6-oxo-4-propyl-1,4,5,6-tetrahydro-pyrimidin-4-yl)-phenyl]-amide,
2-methyl-oxazole-4-carboxylic acid [3-((S)-2-amino-1-methyl-6-oxo-4-propyl-1,4,5,6-tetrahydro-pyrimidin-4-yl)-phenyl]-amide,
5-chloro-pyridine-2-carboxylic acid [3-((4S,5R)-2-amino-1,4,5-trimethyl-6-oxo-1,4,5,6-tetrahydro-pyrimidin-4-yl)-phenyl]-amide,
5-chloro-pyridine-2-carboxylic acid [3-((4S,5R)-2-amino-5-ethyl-1,4-dimethyl-6-oxo-1,4,5,6-tetrahydro-pyrimidin-4-yl)-phenyl]-amide,
3-methoxy-pyridine-2-carboxylic acid [3-((R)-2-amino-1,4,5,5-tetramethyl-6-oxo-1,4,5,6-tetrahydro-pyrimidin-4-yl)-phenyl]-amide,
5-chloro-pyridine-2-carboxylic acid [3-((R)-2-amino-1,4,5,5-tetramethyl-6-oxo-1,4,5,6-tetrahydro-pyrimidin-4-yl)-phenyl]-amide,
5-chloro-3-methyl-pyridine-2-carboxylic acid [3-((R)-2-amino-1,4,5,5-tetramethyl-6-oxo-1,4,5,6-tetrahydro-pyrimidin-4-yl)-phenyl]-amide,
thieno[2,3-c]pyridine-7-carboxylic acid [3-((R)-2-amino-1,4,5,5-tetramethyl-6-oxo-1,4,5,6-tetrahydro-pyrimidin-4-yl)-phenyl]-amide, 3-(2-chloro-phenyl)-pyridine-2-carboxylic acid [3-((R)-2-amino-1,4,5,5-tetramethyl-6-oxo-1,4,5,6-tetrahydro-pyrimidin-4-yl)-phenyl]-amide,
1-methyl-1H-pyrazole-3-carboxylic acid [3-((S)-2-amino-1,4,5,5-tetramethyl-6-oxo-1,4,5,6-tetrahydro-pyrimidin-4-yl)-4-fluoro-phenyl]-amide,
5-chloro-3-methyl-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
2-methyl-oxazole-4-carboxylic acid [3-((S)-2-amino-1,4,5,5-tetramethyl-6-oxo-1,4,5,6-tetrahydro-pyrimidin-4-yl)-4-fluoro-phenyl]-amide,
5-methyl-thiophene-2-carboxylic acid [3-((S)-2-amino-1,4,5,5-tetramethyl-6-oxo-1,4,5,6-tetrahydro-pyrimidin-4-yl)-4-fluoro-phenyl]-amide,
5-difluoromethoxy-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
3-methoxy-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
3-methyl-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
5-chloro-pyrimidine-2-carboxylic acid [3-((S)-2-amino-1,4,5,5-tetramethyl-6-oxo-1,4,5,6-tetrahydro-pyrimidin-4-yl)-4-fluoro-phenyl]-amide,
5-chloro-pyrazine-2-carboxylic acid [3-((S)-2-amino-1,4,5,5-tetramethyl-6-oxo-1,4,5,6-tetrahydro-pyrimidin-4-yl)-4-fluoro-phenyl]-amide,
3-fluoro-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
5-phenyl-oxazole-4-carboxylic acid [3-((S)-2-amino-1,4,5,5-tetramethyl-6-oxo-1,4,5,6-tetrahydro-pyrimidin-4-yl)-4-fluoro-phenyl]-amide,
5-trifluoromethyl-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
1-methyl-1H-imidazole-2-carboxylic acid [3-((S)-2-amino-1,4,5,5-tetramethyl-6-oxo-1,4,5,6-tetrahydro-pyrimidin-4-yl)-4-fluoro-phenyl]-amide,
1-methyl-1H-imidazole-4-carboxylic acid [3-((S)-2-amino-1,4,5,5-tetramethyl-6-oxo-1,4,5,6-tetrahydro-pyrimidin-4-yl)-4-fluoro-phenyl]-amide,
5-methoxy-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
5-fluoro-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
5-cyano-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
5-methyl-isoxazole-3-carboxylic acid [3-((S)-2-amino-1,4,5,5-tetramethyl-6-oxo-1,4,5,6-tetrahydro-pyrimidin-4-yl)-4-fluoro-phenyl]-amide,
oxazole-2-carboxylic acid [3-((S)-2-amino-1,4,5,5-tetramethyl-6-oxo-1,4,5,6-tetrahydro-pyrimidin-4-yl)-4-fluoro-phenyl]-amide,
3-chloro-5-trifluoromethyl-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
6-chloro-3-trifluoromethyl-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
6-chloro-imidazo[1,2-a]pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
1-difluoromethyl-1H-pyrazole-3-carboxylic acid [3-((S)-2-amino-1,4,5,5-tetramethyl-6-oxo-1,4,5,6-tetrahydro-pyrimidin-4-yl)-4-fluoro-phenyl]-amide,
5-chloro-pyridine-2-carboxylic acid [3-((R)-2-amino-5-benzyloxy-1,4-dimethyl-6-oxo-1,4,5,6-tetrahydro-pyrimidin-4-yl)-4-fluoro-phenyl]-amide,
pyridine-2-carboxylic acid [3-((R)-2-amino-5-hydroxy-1,4-dimethyl-6-oxo-1,4,5,6-tetrahydro-pyrimidin-4-yl)-4-fluoro-phenyl]-amide,
5-chloro-pyridine-2-carboxylic acid [3-((S)-2-amino-1-cyclopropylmethyl-4-methyl-6-oxo-1,4,5,6-tetrahydro-pyrimidin-4-yl)-phenyl]-amide,
5-chloro-pyridine-2-carboxylic acid [5-((S)-2-amino-1,4-dimethyl-6-oxo-1,4,5,6-tetrahydro-pyrimidin-4-yl)-2-fluoro-phenyl]-amide,
5-chloro-pyridine-2-carboxylic acid [3-((S)-2-amino-1,4,5,5-tetramethyl-6-oxo-1,4,5,6-tetrahydro-pyrimidin-4-yl)-4-chloro-phenyl]-amide,
N-[(1S)-2'-amino-1'-methyl-6'-oxo-2,3,5',6'-tetrahydro-1'H-spiro[indene-1,4'-pyrimidin]-6-yl]-5-chloropyridine-2-carboxamide,
N-[(1S)-2'-amino-1'-methyl-6'-oxo-2,3,5',6'-tetrahydro-1'H-spiro[indene-1,4'-pyrimidin]-6-yl]pyridine-2-carboxamide,
N-[(1S)-2'-amino-1'-methyl-6'-oxo-2,3,5',6'-tetrahydro-1'H-spiro[indene-1,4'-pyrimidin]-6-yl]-5-(2,2,2-trifluoro-ethoxy)-pyridine-2-carboxamide,
N-[(1S)-2'-amino-1'-methyl-6'-oxo-2,3,5',6'-tetrahydro-1'H-spiro[indene-1,4'-pyrimidin]-6-yl]-3-trifluoromethyl-pyridine-2-carboxamide,
and pharmaceutically acceptable salts of the above compounds.

Particularly preferred compounds of formula I of the present invention are the following:
(5-methyl-thiophene-2-carboxylic acid [3-((S)-2-amino-1,4-dimethyl-6-oxo-1,4,5,6-tetrahydro-pyrimidin-4-yl)-phenyl]-amide,
5-chloro-thiophene-2-carboxylic acid [3-((S)-2-amino-1,4-dimethyl-6-oxo-1,4,5,6-tetrahydro-pyrimidin-4-yl)-phenyl]-amide,
5-chloro-pyridine-2-carboxylic acid [3-((S)-2-amino-1,4-dimethyl-6-oxo-1,4,5,6-tetrahydro-pyrimidin-4-yl)-phenyl]-amide,
5-trifluoromethyl-pyridine-2-carboxylic acid [3-((S)-2-amino-1,4-dimethyl-6-oxo-1,4,5,6-tetrahydro-pyrimidin-4-yl)-phenyl]-amide,
5-methyl-pyridine-2-carboxylic acid [3-((S)-2-amino-1,4-dimethyl-6-oxo-1,4,5,6-tetrahydro-pyrimidin-4-yl)-phenyl]-amide,
pyridine-2-carboxylic acid [3-((S)-2-amino-1,4-dimethyl-6-oxo-1,4,5,6-tetrahydro-pyrimidin-4-yl)-phenyl]-amide,
5-methoxy-pyridine-2-carboxylic acid [3-((S)-2-amino-1,4-dimethyl-6-oxo-1,4,5,6-tetrahydro-pyrimidin-4-yl)-phenyl]-amide,
5-cyano-pyridine-2-carboxylic acid [3-((S)-2-amino-1,4-dimethyl-6-oxo-1,4,5,6-tetrahydro-pyrimidin-4-yl)-phenyl]-amide,
N-[3-((S)-2-amino-1,4-dimethyl-6-oxo-1,4,5,6-tetrahydro-pyrimidin-4-yl)-phenyl]-4-chloro-benzamide, 5-chloro-pyrimidine-2-carboxylic acid [3-((S)-2-amino-1,4-dimethyl-6-oxo-1,4,5,6-tetrahydro-pyrimidin-4-yl)-phenyl]-amide,
5-chloro-pyrazine-2-carboxylic acid [3-((S)-2-amino-1,4-dimethyl-6-oxo-1,4,5,6-tetrahydro-pyrimidin-4-yl)-phenyl]-amide,
5-fluoro-pyridine-2-carboxylic acid [3-((S)-2-amino-1,4-dimethyl-6-oxo-1,4,5,6-tetrahydro-pyrimidin-4-yl)-phenyl]-amide,
3-chloro-pyridine-2-carboxylic acid [3-((S)-2-amino-1,4-dimethyl-6-oxo-1,4,5,6-tetrahydro-pyrimidin-4-yl)-phenyl]-amide,
4-chloro-pyridine-2-carboxylic acid [3-((S)-2-amino-1,4-dimethyl-6-oxo-1,4,5,6-tetrahydro-pyrimidin-4-yl)-phenyl]-amide,
6-chloro-pyridine-2-carboxylic acid [3-((S)-2-amino-1,4-dimethyl-6-oxo-1,4,5,6-tetrahydro-pyrimidin-4-yl)-phenyl]-amide,
3-phenyl-pyridine-2-carboxylic acid [3-((S)-2-amino-1,4-dimethyl-6-oxo-1,4,5,6-tetrahydro-pyrimidin-4-yl)-phenyl]-amide,
2-methyl-oxazole-4-carboxylic acid [3-((S)-2-amino-1,4-dimethyl-6-oxo-1,4,5,6-tetrahydro-pyrimidin-4-yl)-phenyl]-amide,
5-chloro-pyridine-2-carboxylic acid [3-((S)-2-amino-4-ethyl-1-methyl-6-oxo-1,4,5,6-tetrahydro-pyrimidin-4-yl)-phenyl]-amide,
pyridine-2-carboxylic acid [3-((S)-2-amino-4-ethyl-1-methyl-6-oxo-1,4,5,6-tetrahydro-pyrimidin-4-yl)-phenyl]-amide,
5-chloro-pyrimidine-2-carboxylic acid [3-((S)-2-amino-4-ethyl-1-methyl-6-oxo-1,4,5,6-tetrahydro-pyrimidin-4-yl)-phenyl]-amide,
5-chloro-pyridine-2-carboxylic acid [3-((S)-2-amino-1,4-dimethyl-6-oxo-1,4,5,6-tetrahydro-pyrimidin-4-yl)-4-fluoro-phenyl]-amide,
5-chloro-pyrimidine-2-carboxylic acid [3-((S)-2-amino-1,4-dimethyl-6-oxo-1,4,5,6-tetrahydro-pyrimidin-4-yl)-4-fluoro-phenyl]-amide,
pyridine-2-carboxylic acid [3-((S)-2-amino-1,4-dimethyl-6-oxo-1,4,5,6-tetrahydro-pyrimidin-4-yl)-4-fluoro-phenyl]-amide,
5-trifluoromethyl-pyridine-2-carboxylic acid [3-((S)-2-amino-1,4-dimethyl-6-oxo-1,4,5,6-tetrahydro-pyrimidin-4-yl)-4-fluoro-phenyl]-amide,
5-chloro-pyridine-2-carboxylic acid [3-((S)-2-amino-1-ethyl-4-methyl-6-oxo-1,4,5,6-tetrahydro-pyrimidin-4-yl)-phenyl]-amide,
5-chloro-pyridine-2-carboxylic acid [3-((S)-2-amino-1-benzyl-4-methyl-6-oxo-1,4,5,6-tetrahydro-pyrimidin-4-yl)-phenyl]-amide,
5-chloro-pyridine-2-carboxylic acid [3-((S)-2-amino-4-methyl-6-oxo-1,4,5,6-tetrahydro-pyrimidin-4-yl)-phenyl]-amide,
5-chloro-pyridine-2-carboxylic acid [5-((S)-2-amino-1,4-dimethyl-6-oxo-1,4,5,6-tetrahydro-pyrimidin-4-yl)-pyridin-3-yl]-amide,
5-chloro-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
3-chloro-5-trifluoromethyl-pyridine-2-carboxylic acid [3-((S)-2-amino-1,4-dimethyl-6-oxo-1,4,5,6-tetrahydro-pyrimidin-4-yl)-phenyl]-amide,
5-chloro-3-methyl-pyridine-2-carboxylic acid [3-((S)-2-amino-1,4-dimethyl-6-oxo-1,4,5,6-tetrahydro-pyrimidin-4-yl)-phenyl]-amide,
5-chloro-pyridine-2-carboxylic acid [3-((4S,5R)-2-amino-1,4,5-trimethyl-6-oxo-1,4,5,6-tetrahydro-pyrimidin-4-yl)-phenyl]-amide,
5-chloro-pyridine-2-carboxylic acid [3-((4S,5R)-2-amino-5-ethyl-1,4-dimethyl-6-oxo-1,4,5,6-tetrahydro-pyrimidin-4-yl)-phenyl]-amide,
5-chloro-pyridine-2-carboxylic acid [3-((R)-2-amino-1,4,5,5-tetramethyl-6-oxo-1,4,5,6-tetrahydro-pyrimidin-4-yl)-phenyl]-amide,
5-chloro-3-methyl-pyridine-2-carboxylic acid [3-((R)-2-amino-1,4,5,5-tetramethyl-6-oxo-1,4,5,6-tetrahydro-pyrimidin-4-yl)-phenyl]-amide,
5-chloro-3-methyl-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
2-methyl-oxazole-4-carboxylic acid [3-((S)-2-amino-1,4,5,5-tetramethyl-6-oxo-1,4,5,6-tetrahydro-pyrimidin-4-yl)-4-fluoro-phenyl]-amide,
5-chloro-pyrimidine-2-carboxylic acid [3-((S)-2-amino-1,4,5,5-tetramethyl-6-oxo-1,4,5,6-tetrahydro-pyrimidin-4-yl)-4-fluoro-phenyl]-amide,
5-chloro-pyrazine-2-carboxylic acid [3-((S)-2-amino-1,4,5,5-tetramethyl-6-oxo-1,4,5,6-tetrahydro-pyrimidin-4-yl)-4-fluoro-phenyl]-amide,
3-fluoro-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
3-chloro-5-trifluoromethyl-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide,
1-difluoromethyl-1H-pyrazole-3-carboxylic acid [3-((S)-2-amino-1,4,5,5-tetramethyl-6-oxo-1,4,5,6-tetrahydro-pyrimidin-4-yl)-4-fluoro-phenyl]-amide, and
pharmaceutically acceptable salts of the above compounds.

The pharmaceutically acceptable salts of the compounds of formula I also individually constitute preferred compounds of the present invention.

In particular, the invention relates to the salts of compounds of formula I with HCl, formic acid and trifluoroacetic acid (CF$_3$COOH), i.e. the chloride salts, the formate salts and trifluoroacetate salts.

Within this group, the following salts are preferred:
5-methyl-thiophene-2-carboxylic acid [3-((S)-2-amino-1,4-dimethyl-6-oxo-1,4,5,6-tetrahydro-pyrimidin-4-yl)-phenyl]-amide; salt with HCl,
5-chloro-thiophene-2-carboxylic acid [3-((S)-2-amino-1,4-dimethyl-6-oxo-1,4,5,6-tetrahydro-pyrimidin-4-yl)-phenyl]-amide; salt with HCl,
2,5-dimethyl-thiophene-3-carboxylic acid [3-((S)-2-amino-1,4-dimethyl-6-oxo-1,4,5,6-tetrahydro-pyrimidin-4-yl)-phenyl]-amide; salt with HCl,
2,5-dimethyl-oxazole-4-carboxylic acid [3-((S)-2-amino-1,4-dimethyl-6-oxo-1,4,5,6-tetrahydro-pyrimidin-4-yl)-phenyl]-amide; salt with HCl,
2,4-dimethyl-oxazole-5-carboxylic acid [3-((S)-2-amino-1,4-dimethyl-6-oxo-1,4,5,6-tetrahydro-pyrimidin-4-yl)-phenyl]-amide; salt with HCl,
3-methyl-isoxazole-5-carboxylic acid [3-((S)-2-amino-1,4-dimethyl-6-oxo-1,4,5,6-tetrahydro-pyrimidin-4-yl)-phenyl]-amide; salt with formic acid,
1,5-dimethyl-1H-pyrazole-3-carboxylic acid [3-((S)-2-amino-1,4-dimethyl-6-oxo-1,4,5,6-tetrahydro-pyrimidin-4-yl)-phenyl]-amide; salt with HCl,
2,5-dimethyl-2H-pyrazole-3-carboxylic acid [3-((S)-2-amino-1,4-dimethyl-6-oxo-1,4,5,6-tetrahydro-pyrimidin-4-yl)-phenyl]-amide; salt with HCl, imidazo[1,2-a]pyridine-2-carboxylic acid [3-((S)-2-amino-1,4-dimethyl-6-oxo-1,4,5,6-tetrahydro-pyrimidin-4-yl)-phenyl]-amide; salt with HCl, 5-chloro-pyridine-2-carboxylic acid [3-((S)-2-amino-1,4-dimethyl-6-oxo-1,4,5,6-tetrahydro-pyrimidin-4-yl)-phenyl]-amide; salt with HCl, 5-trifluoromethyl-pyridine-2-carboxylic acid [3-((S)-2-amino-1,4-dimethyl-6-oxo-1,4,5,6-tetrahydro-pyrimidin-4-yl)-phenyl]-amide; salt with formic acid, 5-methyl-pyridine-2-carboxylic acid [3-((S)-2-amino-1,4-dimethyl-6-oxo-1,4,5,6-tetrahydro-pyrimidin-4-yl)-phenyl]-amide; salt with HCl, pyridine-2-carboxylic acid [3-((S)-2-amino-1,4-dimethyl-6-oxo-1,4,5,6-tetrahydro-pyrimidin-4-yl)-phenyl]-amide; salt with formic acid, 5-methoxy-pyridine-2-carboxylic acid [3-((S)-2-amino-1,4-dimethyl-6-oxo-1,4,5,6-tetrahydro-pyrimidin-4-yl)-phenyl]-amide; salt with formic acid, 5-cyano-pyridine-2-carboxylic acid [3-((S)-2-amino-1,4-dimethyl-6-oxo-1,4,5,6-tetrahydro-pyrimidin-4-yl)-phenyl]-amide; salt with HCl, 5-hydroxymethyl-pyridine-2-carboxylic acid [3-((S)-2-amino-1,4-dimethyl-6-oxo-1,4,5,6-tetrahydro-pyrimidin-4-yl)-phenyl]-amide; salt with HCl, N-[3-((S)-2-amino-1,4-dimethyl-6-oxo-1,4,5,6-tetrahydro-pyrimidin-4-yl)-phenyl]-4-methyl-benzamide; salt with formic acid, N-[3-((S)-2-amino-1,4-dimethyl-6-oxo-1,4,5,6-tetrahydro-pyrimidin-4-yl)-phenyl]-4-chloro-benzamide; salt with HCl, N-[3-((S)-2-amino-1,4-dimethyl-6-oxo-1,4,5,6-tetrahydro-pyrimidin-4-yl)-phenyl]-6-chloro-nicotinamide; salt with HCl, 5-chloro-pyrimidine-2-carboxylic acid [3-((S)-2-amino-1,4-dimethyl-6-oxo-1,4,5,6-tetrahydro-pyrimidin-4-yl)-phenyl]-amide; salt with HCl, 1-methyl-6-oxo-1,6-dihydro-pyridazine-3-carboxylic acid [3-((S)-2-amino-1,4-dimethyl-6-oxo-1,4,5,6-tetrahydro-pyrimidin-4-yl)-phenyl]-amide; salt with HCl, 5-methyl-pyrazine-2-carboxylic acid [3-((S)-2-amino-1,4-dimethyl-6-oxo-1,4,5,6-tetrahydro-pyrimidin-4-yl)-phenyl]-amide; salt with formic acid, 6-oxo-1,6-dihydro-pyridazine-3-carboxylic acid [3-((S)-2-amino-1,4-dimethyl-6-oxo-1,4,5,6-tetrahydro-pyrimidin-4-yl)-phenyl]-amide; salt with HCl, 6-methyl-pyrazine-2-carboxylic acid [3-((S)-2-amino-1,4-dimethyl-6-oxo-1,4,5,6-tetrahydro-pyrimidin-4-yl)-phenyl]-amide; salt with HCl, 5-chloro-pyrazine-2-carboxylic acid [3-((S)-2-amino-1,4-dimethyl-6-oxo-1,4,5,6-tetrahydro-pyrimidin-4-yl)-phenyl]-amide; salt with formic acid, N-[3-((S)-2-amino-1,4-dimethyl-6-oxo-1,4,5,6-tetrahydro-pyrimidin-4-yl)-phenyl]-isonicotinamide; salt with formic acid, 5-fluoro-pyridine-2-carboxylic acid [3-((S)-2-amino-1,4-dimethyl-6-oxo-1,4,5,6-tetrahydro-pyrimidin-4-yl)-phenyl]-amide; salt with formic acid, 3-chloro-pyridine-2-carboxylic acid [3-((S)-2-amino-1,4-dimethyl-6-oxo-1,4,5,6-tetrahydro-pyrimidin-4-yl)-phenyl]-amide; salt with HCl, 4-methyl-pyridine-2-carboxylic acid [3-((S)-2-amino-1,4-dimethyl-6-oxo-1,4,5,6-tetrahydro-pyrimidin-4-yl)-phenyl]-amide; salt with formic acid, 6-chloro-pyridine-2-carboxylic acid [3-((S)-2-amino-1,4-dimethyl-6-oxo-1,4,5,6-tetrahydro-pyrimidin-4-yl)-phenyl]-amide; salt with formic acid, 6-methyl-pyridine-2-carboxylic acid [3-((S)-2-amino-1,4-dimethyl-6-oxo-1,4,5,6-tetrahydro-pyrimidin-4-yl)-phenyl]-amide; salt with formic acid, N-[3-((S)-2-amino-1,4-dimethyl-6-oxo-1,4,5,6-tetrahydro-pyrimidin-4-yl)-phenyl]-benzamide; salt with formic acid, 2-methyl-pyrimidine-5-carboxylic acid [3-((S)-2-amino-1,4-dimethyl-6-oxo-1,4,5,6-tetrahydro-pyrimidin-4-yl)-phenyl]-amide; salt with CF$_3$COOH, 5-oxo-4,5-dihydro-pyrazine-2-carboxylic acid [3-((S)-2-amino-1,4-dimethyl-6-oxo-1,4,5,6-tetrahydro-pyrimidin-4-yl)-phenyl]-amide; salt with CF$_3$COOH, 3-phenyl-pyridine-2-carboxylic acid [3-((S)-2-amino-1,4-dimethyl-6-oxo-1,4,5,6-tetrahydro-pyrimidin-4-yl)-phenyl]-amide; salt with CF$_3$COOH, 2-methyl-oxazole-4-carboxylic acid [3-((S)-2-amino-1,4-dimethyl-6-oxo-1,4,5,6-tetrahydro-pyrimidin-4-yl)-phenyl]-amide; salt with CF$_3$COOH, 5-chloro-pyridine-2-carboxylic acid [3-((S)-2-amino-4-ethyl-1-methyl-6-oxo-1,4,5,6-tetrahydro-pyrimidin-4-yl)-phenyl]-amide; salt with CF$_3$COOH, pyridine-2-carboxylic acid [3-((S)-2-amino-4-ethyl-1-methyl-6-oxo-1,4,5,6-tetrahydro-pyrimidin-4-yl)-phenyl]-amide; salt with CF$_3$COOH, 5-chloro-thiophene-2-carboxylic acid [3-((S)-2-amino-4-ethyl-1-methyl-6-oxo-1,4,5,6-tetrahydro-pyrimidin-4-yl)-phenyl]-amide; salt with CF$_3$COOH, 6-chloro-pyridine-2-carboxylic acid [3-((S)-2-amino-4-ethyl-1-methyl-6-oxo-1,4,5,6-tetrahydro-pyrimidin-4-yl)-phenyl]-amide; salt with CF$_3$COOH, 3-chloro-pyridine-2-carboxylic acid [3-((S)-2-amino-4-ethyl-1-methyl-6-oxo-1,4,5,6-tetrahydro-pyrimidin-4-yl)-phenyl]-amide; salt with CF$_3$COOH, 5-chloro-pyrimidine-2-carboxylic acid [3-((S)-2-amino-4-ethyl-1-methyl-6-oxo-1,4,5,6-tetrahydro-pyrimidin-4-yl)-phenyl]-amide; salt with CF$_3$COOH, 5-chloro-pyridine-2-carboxylic acid [3-((S)-2-amino-1,4-dimethyl-6-oxo-1,4,5,6-tetrahydro-pyrimidin-4-yl)-4-fluoro-phenyl]-amide; salt with HCl, 5-chloro-pyrimidine-2-carboxylic acid [3-((S)-2-amino-1,4-dimethyl-6-oxo-1,4,5,6-tetrahydro-pyrimidin-4-yl)-4-fluoro-phenyl]-amide; salt with CF$_3$COOH, pyridine-2-carboxylic acid [3-((S)-2-amino-1,4-dimethyl-6-oxo-1,4,5,6-tetrahydro-pyrimidin-4-yl)-4-fluoro-phenyl]-amide; salt with CF$_3$COOH, 5-trifluoromethyl-pyridine-2-carboxylic acid [3-((S)-2-amino-1,4-dimethyl-6-oxo-1,4,5,6-tetrahydro-pyrimidin-4-yl)-4-fluoro-phenyl]-amide; salt with CF$_3$COOH, 5-chloro-pyridine-2-carboxylic acid [3-((S)-2-amino-1-ethyl-4-methyl-6-oxo-1,4,5,6-tetrahydro-pyrimidin-4-yl)-phenyl]-amide; salt with HCl, 5-chloro-pyridine-2-carboxylic acid [3-((S)-2-amino-1-benzyl-4-methyl-6-oxo-1,4,5,6-tetrahydro-pyrimidin-4-yl)-phenyl]-amide; salt with CF$_3$COOH, 5-chloro-pyridine-2-carboxylic acid [3-((S)-2-amino-4-methyl-6-oxo-1,4,5,6-tetrahydro-pyrimidin-4-yl)-phenyl]-amide; salt with CF$_3$COOH, 5-chloro-pyridine-2-carboxylic acid [5-((S)-2-amino-1,4-dimethyl-6-oxo-1,4,5,6-tetrahydro-pyrimidin-4-yl)-pyridin-3-yl]-amide; salt with CF$_3$COOH, 5-chloro-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 3,6-dichloro-pyridine-2-carboxylic acid [3-((S)-2-amino-1,4-dimethyl-6-oxo-1,4,5,6-tetrahydro-pyrimidin-4-yl)-phenyl]-amide; salt with CF$_3$COOH, 3-propoxy-pyridine-2-carboxylic acid [3-((S)-2-amino-1,4-dimethyl-6-oxo-1,4,5,6-tetrahydro-pyrimidin-4-yl)-phenyl]-amide; salt with CF₃COOH,
isoquinoline-1-carboxylic acid [3-((S)-2-amino-1,4-dimethyl-6-oxo-1,4,5,6-tetrahydro-pyrimidin-4-yl)-phenyl]-amide; salt with CF₃COOH,
isoquinoline-3-carboxylic acid [3-((S)-2-amino-1,4-dimethyl-6-oxo-1,4,5,6-tetrahydro-pyrimidin-4-yl)-phenyl]-amide; salt with CF₃COOH,
quinoline-2-carboxylic acid [3-((S)-2-amino-1,4-dimethyl-6-oxo-1,4,5,6-tetrahydro-pyrimidin-4-yl)-phenyl]-amide; salt with CF₃COOH,
thieno[3,2-b]pyridine-5-carboxylic acid [3-((S)-2-amino-1,4-dimethyl-6-oxo-1,4,5,6-tetrahydro-pyrimidin-4-yl)-phenyl]-amide; salt with CF₃COOH,
thieno[2,3-c]pyridine-7-carboxylic acid [3-((S)-2-amino-1,4-dimethyl-6-oxo-1,4,5,6-tetrahydro-pyrimidin-4-yl)-phenyl]-amide; salt with CF₃COOH,
3-phenylsulfanyl-pyridine-2-carboxylic acid [3-((S)-2-amino-1,4-dimethyl-6-oxo-1,4,5,6-tetrahydro-pyrimidin-4-yl)-phenyl]-amide; salt with CF₃COOH,
3-trifluoromethyl-pyridine-2-carboxylic acid [3-((S)-2-amino-1,4-dimethyl-6-oxo-1,4,5,6-tetrahydro-pyrimidin-4-yl)-phenyl]-amide; salt with CF₃COOH,
5-(2,2,2-trifluoro-ethoxy)-pyridine-2-carboxylic acid [3-((S)-2-amino-1,4-dimethyl-6-oxo-1,4,5,6-tetrahydro-pyrimidin-4-yl)-phenyl]-amide; salt with CF₃COOH,
3,5-dichloro-pyridine-2-carboxylic acid [3-((S)-2-amino-1,4-dimethyl-6-oxo-1,4,5,6-tetrahydro-pyrimidin-4-yl)-phenyl]-amide; salt with CF₃COOH,
3-methoxy-pyridine-2-carboxylic acid [3-((S)-2-amino-1,4-dimethyl-6-oxo-1,4,5,6-tetrahydro-pyrimidin-4-yl)-phenyl]-amide; compound with CF₃COOH,
2-trifluoromethyl-thiazole-4-carboxylic acid [3-((S)-2-amino-1,4-dimethyl-6-oxo-1,4,5,6-tetrahydro-pyrimidin-4-yl)-phenyl]-amide; compound with CF₃COOH,
2-methyl-thiazole-4-carboxylic acid [3-((S)-2-amino-1,4-dimethyl-6-oxo-1,4,5,6-tetrahydro-pyrimidin-4-yl)-phenyl]-amide; compound with CF₃COOH,
benzo[b]thiophene-2-carboxylic acid [3-((S)-2-amino-1,4-dimethyl-6-oxo-1,4,5,6-tetrahydro-pyrimidin-4-yl)-phenyl]-amide; compound with CF₃COOH,
1-methyl-1H-pyrazole-3-carboxylic acid [3-((S)-2-amino-1,4-dimethyl-6-oxo-1,4,5,6-tetrahydro-pyrimidin-4-yl)-phenyl]-amide; compound with CF₃COOH,
3-chloro-5-trifluoromethyl-pyridine-2-carboxylic acid [3-((S)-2-amino-1,4-dimethyl-6-oxo-1,4,5,6-tetrahydro-pyrimidin-4-yl)-phenyl]-amide; compound with CF₃COOH,
2-phenyl-oxazole-4-carboxylic acid [3-((S)-2-amino-1,4-dimethyl-6-oxo-1,4,5,6-tetrahydro-pyrimidin-4-yl)-phenyl]-amide; compound with CF₃COOH,
6-chloro-3-trifluoromethyl-pyridine-2-carboxylic acid [3-((S)-2-amino-1,4-dimethyl-6-oxo-1,4,5,6-tetrahydro-pyrimidin-4-yl)-phenyl]-amide; compound with CF₃COOH,
1-(2,2,2-trifluoro-ethyl)-1H-pyrazole-3-carboxylic acid [3-((S)-2-amino-1,4-dimethyl-6-oxo-1,4,5,6-tetrahydro-pyrimidin-4-yl)-phenyl]-amide; compound with CF₃COOH,
3-ethoxy-5-trifluoromethyl-pyridine-2-carboxylic acid [3-((S)-2-amino-1,4-dimethyl-6-oxo-1,4,5,6-tetrahydro-pyrimidin-4-yl)-phenyl]-amide; compound with CF₃COOH,
5-chloro-3-methyl-pyridine-2-carboxylic acid [3-((S)-2-amino-1,4-dimethyl-6-oxo-1,4,5,6-tetrahydro-pyrimidin-4-yl)-phenyl]-amide; compound with CF₃COOH,
5-(3-trifluoromethyl-pyrazol-1-yl)-pyridine-2-carboxylic acid [3-((S)-2-amino-1,4-dimethyl-6-oxo-1,4,5,6-tetrahydro-pyrimidin-4-yl)-phenyl]-amide; compound with CF₃COOH,
1,3-dimethyl-1H-pyrazole-4-carboxylic acid [3-((S)-2-amino-1,4-dimethyl-6-oxo-1,4,5,6-tetrahydro-pyrimidin-4-yl)-phenyl]-amide; compound with CF₃COOH,
1H-pyrrolo[2,3-b]pyridine-2-carboxylic acid [3-((S)-2-amino-1,4-dimethyl-6-oxo-1,4,5,6-tetrahydro-pyrimidin-4-yl)-phenyl]-amide; compound with CF₃COOH,
2-cyclopropyl-5-methyl-2H-pyrazole-3-carboxylic acid [3-((S)-2-amino-1,4-dimethyl-6-oxo-1,4,5,6-tetrahydro-pyrimidin-4-yl)-phenyl]-amide; compound with CF₃COOH,
N-[3-((S)-2-amino-1,4-dimethyl-6-oxo-1,4,5,6-tetrahydro-pyrimidin-4-yl)-phenyl]-2-(1H-imidazol-2-yl)-benzamide; compound with CF₃COOH,
isoxazole-3-carboxylic acid [3-((S)-2-amino-1,4-dimethyl-6-oxo-1,4,5,6-tetrahydro-pyrimidin-4-yl)-phenyl]-amide; compound with CF₃COOH,
5-methyl-isoxazole-3-carboxylic acid [3-((S)-2-amino-1,4-dimethyl-6-oxo-1,4,5,6-tetrahydro-pyrimidin-4-yl)-phenyl]-amide; compound with CF₃COOH,
5-ethyl-pyridine-2-carboxylic acid [3-((S)-2-amino-1,4-dimethyl-6-oxo-1,4,5,6-tetrahydro-pyrimidin-4-yl)-phenyl]-amide; compound with CF₃COOH,
4-methyl-1H-imidazole-2-carboxylic acid [3-((S)-2-amino-1,4-dimethyl-6-oxo-1,4,5,6-tetrahydro-pyrimidin-4-yl)-phenyl]-amide; compound with CF₃COOH,
5-fluoro-pyridine-2-carboxylic acid [3-((S)-2-amino-4-ethyl-1-methyl-6-oxo-1,4,5,6-tetrahydro-pyrimidin-4-yl)-phenyl]-amide; compound with CF₃COOH,
5-trifluoromethyl-pyridine-2-carboxylic acid [3-((S)-2-amino-4-ethyl-1-methyl-6-oxo-1,4,5,6-tetrahydro-pyrimidin-4-yl)-phenyl]-amide; compound with CF₃COOH,
5-chloro-pyridine-2-carboxylic acid [3-((S)-2-amino-1-methyl-6-oxo-4-propyl-1,4,5,6-tetrahydro-pyrimidin-4-yl)-phenyl]-amide; salt with CF₃COOH,
pyridine-2-carboxylic acid [3-((S)-2-amino-1-methyl-6-oxo-4-propyl-1,4,5,6-tetrahydro-pyrimidin-4-yl)-phenyl]-amide; compound with CF₃COOH,
1-methyl-1H-pyrazole-3-carboxylic acid [3-((S)-2-amino-1-methyl-6-oxo-4-propyl-1,4,5,6-tetrahydro-pyrimidin-4-yl)-phenyl]-amide; compound with CF₃COOH,
2-methyl-oxazole-4-carboxylic acid [3-((S)-2-amino-1-methyl-6-oxo-4-propyl-1,4,5,6-tetrahydro-pyrimidin-4-yl)-phenyl]-amide; salt with CF₃COOH,
5-chloro-pyridine-2-carboxylic acid [3-((4S,5R)-2-amino-1,4,5-trimethyl-6-oxo-1,4,5,6-tetrahydro-pyrimidin-4-yl)-phenyl]-amide; salt with CF₃COOH,
5-chloro-pyridine-2-carboxylic acid [3-((4S,5R)-2-amino-5-ethyl-1,4-dimethyl-6-oxo-1,4,5,6-tetrahydro-pyrimidin-4-yl)-phenyl]-amide; salt with CF₃COOH,
3-methoxy-pyridine-2-carboxylic acid [3-((R)-2-amino-1,4,5,5-tetramethyl-6-oxo-1,4,5,6-tetrahydro-pyrimidin-4-yl)-phenyl]-amide; salt with formic acid,
5-chloro-pyridine-2-carboxylic acid [3-((R)-2-amino-1,4,5,5-tetramethyl-6-oxo-1,4,5,6-tetrahydro-pyrimidin-4-yl)-phenyl]-amide; salt with formic acid,
5-chloro-3-methyl-pyridine-2-carboxylic acid [3-((R)-2-amino-1,4,5,5-tetramethyl-6-oxo-1,4,5,6-tetrahydro-pyrimidin-4-yl)-phenyl]-amide; salt with formic acid,
thieno[2,3-c]pyridine-7-carboxylic acid [3-((R)-2-amino-1,4,5,5-tetramethyl-6-oxo-1,4,5,6-tetrahydro-pyrimidin-4-yl)-phenyl]-amide; salt with formic acid,
3-(2-chloro-phenyl)-pyridine-2-carboxylic acid [3-((R)-2-amino-1,4,5,5-tetramethyl-6-oxo-1,4,5,6-tetrahydro-pyrimidin-4-yl)-phenyl]-amide; salt with CF₃COOH,
1-methyl-1H-pyrazole-3-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF₃COOH, 5-chloro-3-methyl-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 2-methyl-oxazole-4-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 5-methyl-thiophene-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 5-difluoromethoxy-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 3-methoxy-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 3-methyl-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 5-chloro-pyrimidine-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 5-chloro-pyrazine-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 3-fluoro-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 5-phenyl-oxazole-4-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 5-trifluoromethyl-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 1-methyl-1H-imidazole-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 1-methyl-1H-imidazole-4-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 5-methoxy-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 5-fluoro-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 5-cyano-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with formic acid, 5-methyl-isoxazole-3-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, oxazole-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 3-chloro-5-trifluoromethyl-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 6-chloro-3-trifluoromethyl-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 6-chloro-imidazo[1,2-a]pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 1-difluoromethyl-1H-pyrazole-3-carboxylic acid [3-((S)-2-amino-1,4,5,5-tetramethyl-6-oxo-1,4,5,6-tetrahydro-pyrimidin-4-yl)-4-fluoro-phenyl]-amide; salt with CF$_3$COOH, 5-chloro-pyridine-2-carboxylic acid [3-((R)-2-amino-5-benzyloxy-1,4-dimethyl-6-oxo-1,4,5,6-tetrahydro-pyrimidin-4-yl)-4-fluoro-phenyl]-amide; salt with CF$_3$COOH, pyridine-2-carboxylic acid [3-((R)-2-amino-5-hydroxy-1,4-dimethyl-6-oxo-1,4,5,6-tetrahydro-pyrimidin-4-yl)-4-fluoro-phenyl]-amide; salt with formic acid, 5-chloro-pyridine-2-carboxylic acid [3-((S)-2-amino-1-cyclopropylmethyl-4-methyl-6-oxo-1,4,5,6-tetrahydro-pyrimidin-4-yl)-phenyl]-amide; salt with CF$_3$COOH, 5-chloro-pyridine-2-carboxylic acid [5-((S)-2-amino-1,4-dimethyl-6-oxo-1,4,5,6-tetrahydro-pyrimidin-4-yl)-2-fluoro-phenyl]-amide; salt with CF$_3$COOH, 5-chloro-pyridine-2-carboxylic acid [3-((S)-2-amino-1,4,5,5-tetramethyl-6-oxo-1,4,5,6-tetrahydro-pyrimidin-4-yl)-4-chloro-phenyl]-amide; salt with CF$_3$COOH, N-[(1S)-2'-amino-1'-methyl-6'-oxo-2,3,5',6'-tetrahydro-1'H-spiro[indene-1,4'-pyrimidin]-6-yl]-5-chloropyridine-2-carboxamide; salt with CF$_3$COOH, N-[(1S)-2'-amino-1'-methyl-6'-oxo-2,3,5',6'-tetrahydro-1'H-spiro[indene-1,4'-pyrimidin]-6-yl]pyridine-2-carboxamide; salt with CF$_3$COOH, N-[(1S)-2'-amino-1'-methyl-6'-oxo-2,3,5',6'-tetrahydro-1'H-spiro[indene-1,4'-pyrimidin]-6-yl]-5-(2,2,2-trifluoroethoxy)-pyridine-2-carboxamide; salt with CF$_3$COOH, and N-[(1S)-2'-amino-1'-methyl-6'-oxo-2,3,5',6'-tetrahydro-1'H-spiro[indene-1,4'-pyrimidin]-6-yl]-3-trifluoromethyl-pyridine-2-carboxamide; salt with CF$_3$COOH.

5-Chloro-pyridine-2-carboxylic acid [3-((S)-2-amino-1,4-dimethyl-6-oxo-1,4,5,6-tetrahydro-pyrimidin-4-yl)-phenyl]-amide or its pharmaceutically acceptable salts are particularly preferred.

The skilled person in the art will recognize that the compounds of formula I can exist in tautomeric forms, e.g. in the following tautomeric form:

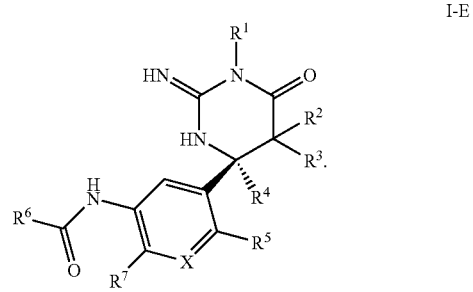

I-E

All tautomeric forms are encompassed in the present invention.

Compounds of formula I possess one asymmetric carbon atom and can exist in the form of optically pure enantiomers and mixtures of enantiomers such as, for example, racemates. The optically active forms can be obtained for example by resolution of the racemates, by asymmetric synthesis or asymmetric chromatography (chromatography with a chiral adsorbents or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Synthesis

A further aspect of the present invention is the process for the manufacture of compounds of formula I as defined above, which process comprises a) reacting an amine of the formula II

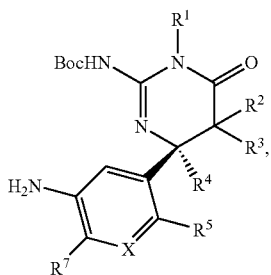

II wherein X, $R^1$ to $R^5$ and $R^7$ are as defined above and Boc is the protecting group tert-butyloxycarbonyl, with a carboxylic acid of the formula III

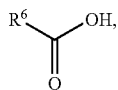

III wherein $R^6$ is as defined above, in the presence of a coupling reagent under basic conditions to obtain a compound of the formula IV

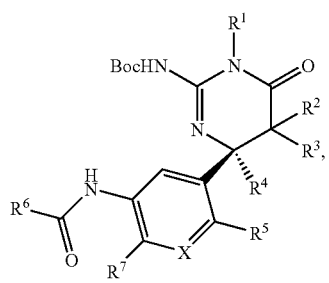

IV and deprotecting the compound of formula IV with the help of a mineral acid to obtain the compound of formula I

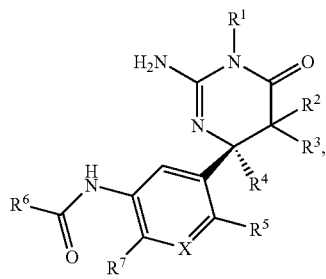

I wherein X and $R^1$ to $R^7$ are as defined above.

Appropriate coupling agents are carbodiimides or uronium salts, such as for example N,N'-carbonyldiimidazole (CDI), N,N'-dicyclohexylcarbodiimide (DCC), N-(3-dimethylaminopropyl)-N'-ethyl-carbodiimide-hydrochloride (EDCI), O-(benzotriazol-1-yl)-N,N,N',N'-tetramethyluronium tetrafluoroborate (TBTU) and 1-[bis(dimethylamino)methylene]-1H-1,2,3-triazolo[4,5-b]pyridinium-3-oxide hexafluorophosphate (HATU). The term "under basic conditions" means the presence of a base, preferably an alkylamine such as diisopropylethylamine (DIEA) or triethylamine (TEA), or a tertiary amine such as N-methylmorpholine or 4-(dimethylamino)-pyridine. The reaction is carried out in a suitable solvent such as for example N,N-dimethylformamide (DMF) or dimethylacetamide (DMAc), at temperatures between 0° C. and ambient temperature.

Preferred mineral acids for the deprotection are sulfuric acid or hydrochloric acid, more preferably hydrochloric acid in a solvent such as an ether, preferably diethyl ether or 1,4-dioxane, or neat trifluoroacetic acid.

The invention further relates to compounds of formula I as defined above obtainable according to a process as defined above.

In more detail, compounds of formula I according to the present invention can be prepared by the methods and procedures given below. A typical procedure for the preparation of compounds of formula I is illustrated in Scheme 1.

Sulfinyl imines of general formula A can be prepared in analogy to T. P. Tang & J. A. Ellman, J. Org. Chem. 1999, 64, 12, by condensation of an aryl ketone and a sulfinamide, e.g. an alkyl sulfinamide, most preferably (R)-(+)-tert-butylsulfinamide in the presence of a Lewis acid such as e.g. a titanium (IV)alkoxide, more preferably titanium(IV)ethoxide in a solvent such as an ether, e.g. diethyl ether or more preferably THF.

The conversion of the sulfinyl imine A to the sulfinamide ester B proceeds stereoselectively by the chiral directing group as described by Tang & Ellman. The sulfinyl imine A can be reacted with a titanium enolate generated from e.g. an alkyl acetate, preferably methyl acetate, LDA and chlorotriisopropoxytitanium at low temperature, preferably at −78° C. in a solvent such as an ether, e.g. diethyl ether or more preferably THF.

Hydrolysis of the chiral directing group in the sulfinamide ester B to give the amino ester C can be accomplished with a mineral acid, e.g. sulfuric acid or preferably hydrochloric acid in a solvent such as an ether, e.g. diethyl ether or more preferably 1,4-dioxane.

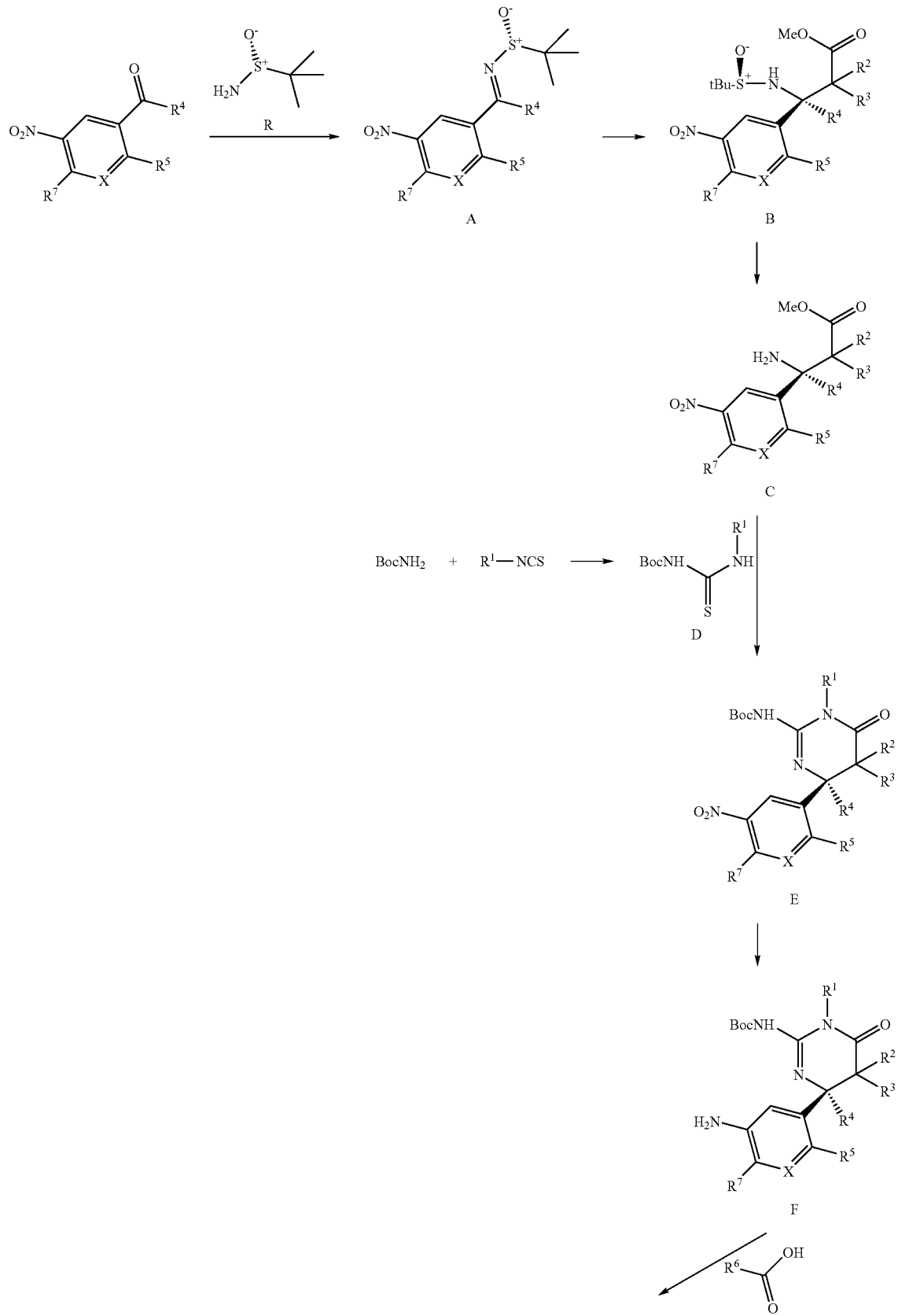

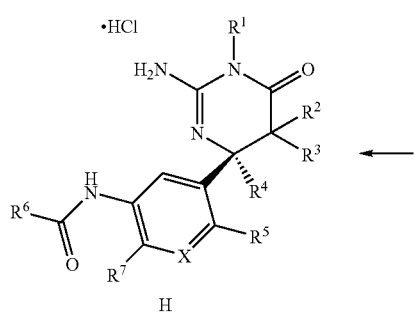

H

-continued

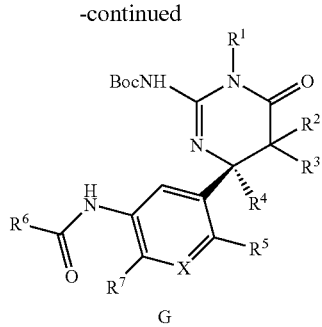

G

Thioureas D can be prepared by the deprotonation of tert-butylcarbamate with an alkali hydride, preferably sodium hydride followed by the reaction with an alkyl isothiocyanate in a solvent such as an ether, e.g. diethyl ether or more preferably THF.

The reaction of the amino ester C and the thiourea D to give the aminodihydro-pyrimidinone E can be effected with a carbodiimide, e.g. DCC or more preferably EDCI and an alkylamine, e.g. TEA or more preferably DIEA, in a solvent such as an alkyl formamide, preferably DMF.

The reduction of the nitro group in the aminodihydropyrimidinone E to the aniline F can be accomplished by hydrogenation using a catalysts such as Pd/C in protic solvents, such as alcohols, preferrably ethanol or methanol.

Amide coupling of the aniline F and a carboxylic acid to give the amide G can be effected with a carbodiimide, e.g. DCC or EDCI or preferably with an uronium salt such as HATU and an alkylamine, e.g. TEA or more preferably DIEA in a solvent such as an alkyl formamide, preferably DMF. Deprotection of the tert-butyloxycarbonyl group in G is effected with a mineral acid, e.g. sulfuric acid or preferably hydrochloric acid in a solvent such as an ether, e.g. diethyl ether or more preferably 1,4-dioxane or in neat trifluoroacetic acid.

Pharmaceutical Compositions and Administration

The invention also relates to pharmaceutical compositions comprising a compound as defined above and a pharmaceutically acceptable carrier and/or adjuvant. More specifically, the invention relates to pharmaceutical compositions useful for the treatment of diseases which are associated with the inhibition of BACE2 activity.

Further, the invention relates to compounds of formula I as defined above for use as medicaments, particularly as medicaments for the treatment or prevention of diseases which are associated with the inhibition of BACE2 activity. Especially preferred are compounds of formula I for use in diabetes, particularly type 2 diabetes.

In another aspect, the invention relates to a method for the treatment or prevention of diseases which are associated with the inhibition of BACE2 activity, which method comprises administering a therapeutically active amount of a compound of formula I to a human being or animal. A method for the treatment of diabetes, particularly type 2 diabetes, is preferred.

The invention further relates to the use of compounds of formula I as defined above for the treatment of diseases which are associated with the inhibition of BACE2 activity.

In addition, the invention relates to the use of compounds of formula I as defined above for the preparation of medicaments for the treatment or prevention of diseases which are associated with the inhibition of BACE2 activity. The use of compounds of formula I as defined above for the preparation of medicaments for the treatment or prevention of diabetes, particularly, type 2 diabetes, is especially preferred.

The compounds of formula I and their pharmaceutically acceptable salts can be used as medicaments, e.g., in the form of pharmaceutical preparations for enteral, parenteral or topical administration. They can be administered, for example, perorally, e.g., in the form of tablets, coated tablets, dragées, hard and soft gelatine capsules, solutions, emulsions or suspensions, rectally, e.g., in the form of suppositories, parenterally, e.g., in the form of injection solutions or suspensions or infusion solutions, or topically, e.g., in the form of ointments, creams or oils. Oral administration is preferred.

The production of the pharmaceutical preparations can be effected in a manner which will be familiar to any person skilled in the art by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1-500 mg, preferably 1-100 mg, of a compound of formula I.

Indications and Methods of Treatment

As described herein before, the compounds of formula I of the present invention can be used as medicaments for the treatment of diseases which are associated with the inhibition of BACE2.

As described herein before, the compounds of formula I of the invention will be useful in preserving and restoring beta-cell function and stimulating insulin secretion in diabetic patients and in non-diabetic patients who have impaired glucose tolerance or who are in a pre-diabetic condition. They may be useful in treating type 1 diabetes or in delaying or preventing a patient with type 2 diabetes from needing insulin therapy. The compounds of formula I are further useful to ameliorate hyperinsulinemia, which often occurs in diabetic or pre-diabetic patients and in reducing the risks associated with metabolic syndrome, they may also be useful in treating vascular diseases such as hypertension.

Accordingly, an aspect of the invention is a method for the treatment of a disease associated with the inhibition of BACE2 activity comprising administering a therapeutically-active amount of the aforementioned compound.

The expression 'diseases which are associated with the inhibition of BACE2 activity' means diseases such as metabolic and cardiovascular diseases, in particular diabetes, more particularly type 2 diabetes, gestational diabetes, impaired fasting glucose, impaired glucose tolerance, insulin resistance, pre-diabetes, metabolic syndrome, diabetes type 1, complications of diabetes including diabetic nephropathy, diabetic retinopathy and diabetic neuropathy, chronic kidney disease, dyslipidemia, atherosclerosis, myocardial infarction, hypertension and further metabolic and cardiovascular disorders.

In a preferable aspect, the expression 'diseases which are associated with the inhibition of BACE2 activity' relates to diabetes, particularly type II diabetes, impaired glucose tolerance, pre-diabetes, metabolic syndrome and hypertension. More preferably, the expression 'diseases which are associated with the inhibition of BACE2 activity' relates to diabetes, most preferably type 2 diabetes.

EXAMPLES

The following examples serve to illustrate the present invention in more detail. They are, however, not intended to limit its scope in any manner.

Abbreviations:

DCC=N,N'-diisopropyl-carbodiimide, DIEA=diisopropylethylamine, DMAc=dimethylacetamide, DMAP=4-dimethylaminopyridine, DMF=N,N-dimethylformamide, DMSO=dimethyl sulfoxide, EDCI=N-(3-dimethylaminopropyl)-N'-ethyl-carbodiimide hydrochloride, HATU=1-[bis(dimethylamino)methylene]-1H-1,2,3-triazolo[4,5-b]pyridinium-3-oxide hexafluorophosphate, HCl=hydrogen chloride, HPLC=high performance liquid chromatography, LDA=lithium diisopropylamide, MS=mass spectrum, NMR=nuclear magnetic resonance, TEA=triethylamine, and THF=tetrahydrofuran.

A. Synthesis of the Intermediate Sulfinyl Imines A

General Procedure

To a solution of the (R)-(+)-tert-butylsulfinamide (66 mmole) in THF (350 ml) was added subsequently the ketone (72.6 mmole) and titanium(IV)ethoxide (132 mmole) and the solution was stirred at reflux temperature for 5 h. The mixture was cooled to 22° C., treated with brine (400 ml), the suspension was stirred for 10 min and filtered over dicalite. The layers were separated, the aqueous layer was extracted with ethyl acetate, the combined organic layers were washed with water, dried and evaporated. The residue was chromatographed on silica using cyclohexane/ethyl acetate (2:1) to give the pure sulfinyl imine A.

Intermediate A1: Starting from 1-(3-nitro-phenyl)-ethanone (66 mmole), the product (R)-2-methyl-propane-2-sulfinic acid [1-(3-nitro-phenyl)-(E)-ethylidene]-amide (12.65 g) was obtained as a pale yellow solid. MS (ESI): m/z=269.2 [M+H]$^+$.

Intermediate A2: Starting from 1-(3-nitro-phenyl)-propan-1-one (25.7 mmole), the product (R)-2-ethyl-propane-2-sulfinic acid [1-(3-nitro-phenyl)-(E)-propylidene]-amide (5.70 g) was obtained as a pale yellow solid. MS (ESI): m/z=283.1 [M+H]$^+$.

Intermediate A3: Starting from 1-(2-fluoro-5-nitro-phenyl)-ethanone (27.3 mmole), the product (R)-2-methyl-propane-2-sulfinic acid [1-(2-fluoro-5-nitro-phenyl)-(E)-ethylidene]-amide (7.0 g) was obtained as a pale yellow solid. MS (ESI): m/z=287.0 [M+H]$^+$.

Intermediate A4: Starting from 1-(5-nitro-pyridin-3-yl)-ethanone (3.68 mmole) prepared according to A. R. Katritzky et al., Org. Biomol. Chem. 2005, 3, 538, the product (R)-2-methyl-propane-2-sulfinic acid [1-(5-nitro-pyridin-3-yl)-eth-(E)-ylidene]-amide (720 mg) was obtained as a pale yellow solid. MS (ESI): m/z=270.4 [M+H]$^+$.

B. Synthesis of the Intermediate Sulfinamide Esters B

General Procedure

To a solution of diisopropylamide (21.9 ml) in THF (250 ml) was added at −78° C. n-butyllithium (1.6 M solution in hexane, 97.2 ml) and stirring was continued at −78° C. for 30 min. The solution was treated with methyl acetate (12.4 ml) and after 30 min a solution of chlorotriisopropoxytitanium (43.0 g) in THF (50 ml) was added and stirring was continued at −78° C. for 30 min. The mixture was treated with a solution of the sulfinyl imine A (47.1 mmole) in THF (25 ml) and stirring was continued at −78° C. for 3 h. The mixture was quenched with saturated aqueous NH$_4$Cl solution (300 ml) and the mixture was filtered over dicalite. The layers were separated, the aqueous layer was extracted with ethyl acetate, the combined organic layers were washed with water, dried and evaporated. The residue was chromatographed on silica using cyclohexane/ethyl acetate (1:2) to give the pure sulfinamide ester B.

Intermediate B1: Starting from (R)-2-methyl-propane-2-sulfinic acid [1-(3-nitro-phenyl)-(E)-ethylidene]-amide (47 mmole), the product (S)-3-((R)-2-methyl-propane-2-sulfinylamino)-3-(3-nitro-phenyl)-butyric acid methyl ester (15.44 g) was obtained as a pale yellow oil. MS (ESI): m/z=343.1 calc [M+H]$^+$.

Intermediate B2: Starting from (R)-2-ethyl-propane-2-sulfinic acid [1-(3-nitro-phenyl)-(E)-propylidene]-amide (1.77 mmole), the product (S)-3-((R)-2-methyl-propane-2-sulfinylamino)-3-(3-nitro-phenyl)-pentanoic acid methyl ester (450 mg) was obtained as a white solid. MS (ESI): m/z=357.1 [M+H]$^+$.

Intermediate B3: Starting from (R)-2-methyl-propane-2-sulfinic acid [1-(2-fluoro-5-nitro-phenyl)-(E)-ethylidene]-amide (10 mmole), the product (S)-3-(2-fluoro-5-nitro-phenyl)-3-((R)-2-methyl-propane-2-sulfinylamino)-butyric acid methyl ester (1.36 g) was obtained as a pale yellow solid. MS (ESI): m/z=361.2 [ M+H]$^+$.

Intermediate B4: Starting from (R)-2-methyl-propane-2-sulfinic acid [1-(5-nitro-pyridin-3-yl)-eth-(E)-ylidene]-amide (2.64 mmole), the product (S)-3-((R)-2-ethyl-propane-2-sulfinylamino)-3-(5-nitro-pyridin-3-yl)-butyric acid methyl ester (255 mg) was obtained as a pale yellow solid. MS (ESI): m/z=344.3 [ M+H]$^+$.

Intermediate B5: Starting from (R)-2-methyl-propane-2-sulfinic acid [1-(2-fluoro-5-nitro-phenyl)-(E)-ethylidene]-amide (3.5 mmole), the product (S)-3-(2-fluoro-5-nitro-phenyl)-2,2-dimethyl-3-((R)-2-methyl-propane-2-sulfinylamino)-butyric acid methyl ester (565 mg) was obtained as a pale yellow solid. MS (ESI): m/z=389.3 [ M+H]$^+$.

C. Synthesis of the Intermediate Amino Esters C

General Procedure

A solution of the sulfinamide ester B (42.2 mmole) in methanol (400 ml) was treated with a solution of HCl in 1,4-dioxane (4 M, 530 ml) and stirring was continued at 22° C. for 2 h. The mixture was evaporated and the residue was partitioned between dichloromethane and 1 M aqueous hydrochloric acid. The aqueous layer was separated, diluted with saturated aqueous Na$_2$CO$_3$ until the pH was ca. 10 and extracted with dichloromethane. The organic layer was dried and evaporated to give the pure aminoester C.

Intermediate C1: Starting from (S)-3-((R)-2-methyl-propane-2-sulfinylamino)-3-(3-nitro-phenyl)-butyric acid methyl ester (42.2 mmole), the product (S)-3-amino-3-(3-nitro-phenyl)-butyric acid methyl ester (9.0 g) was obtained as a colourless oil. MS (ESI): m/z=239.1 [ M+H]$^+$.

Intermediate C2: Starting from (S)-3-((R)-2-methyl-propane-2-sulfinylamino)-3-(3-nitro-phenyl)-pentanoic acid methyl ester (1.30 mmole) the product (S)-3-amino-3-(3-nitro-phenyl)-pentanoic acid methyl ester (306 mg) was obtained as a colourless oil. MS (ESI): m/z=253.3 calc [M+H]$^+$.

Intermediate C3: Starting from (S)-3-(2-fluoro-5-nitro-phenyl)-3-((R)-2-methyl-propane-2-sulfinylamino)-butyric acid methyl ester (16.0 mmole), the product (S)-3-amino-3-(2-fluoro-5-nitro-phenyl)-butyric acid methyl ester (3.80 g) was obtained as a pale yellow oil. MS (ESI): m/z=257.3 [ M+H]$^+$.

Intermediate C4: Starting from (S)-3-((R)-2-ethyl-propane-2-sulfinylamino)-3-(5-nitro-pyridin-3-yl)-butyric acid methyl ester (0.73 mmole), the product (S)-3-amino-3-(5-nitro-pyridin-3-yl)-butyric acid methyl ester (157 mg) was obtained as a pale yellow oil. MS (ESI): m/z=240.2 [ M+H]$^+$.

Intermediate C5: Starting from (S)-3-(2-fluoro-5-nitro-phenyl)-2,2-dimethyl-3-((R)-2-methyl-propane-2-sulfinylamino)-butyric acid methyl ester (2.0 mmole), the product (S)-3-amino-3-(2-fluoro-5-nitro-phenyl)-2,2-dimethyl-butyric acid methyl ester (510 mg) was obtained as a pale yellow oil. MS (ESI): m/z=285.3 [ M+H]$^+$.

D. Synthesis of the Intermediate Thioureas D

General Procedure

To a solution of tert-butylcarbamate (5 mmole) in THF (5.0 ml) was added at 22° C. NaH (60% in oil, 5 mmole) in several portions and stirring was continued at 22° C. for 15 min until gas evolution ceased. The mixture was treated with a solution of the isothiocyanate (5.0 mmole) in THF (5.0 ml) and stirring was continued at 22° C. for 15 min. The mixture was poured into ice-water, extracted with diethylether, the organic layer was washed with water, dried, evaporated and the residue was chromatographed on silica using n-heptane/ethyl acetate or triturated with pentane to give the thiourea D.

Intermediate D1: Starting from isothiocyanatomethane (150.5 mmole), the product tert-butyl [(methylamino)carbonothioyl]carbamate (12.4 g) was obtained as a colourless solid. MS (ESI): m/z=191.4 [ M+H]$^+$.

Intermediate D2: Starting from isothiocyanatoethane (60 mmole), the product tert-butyl [(ethylamino)carbonothioyl]carbamate was obtained (1.30 g) after trituration with pentane as a colourless solid containing some tert-butylcarbamate. MS (ESI): m/z=205.1 [ M+H]$^+$ Intermediate D3: Starting from isothiocyanatomethyl-benzene (21.4 mmole) the product tert-butyl [(benzylamino)carbonothioyl]carbamate was obtained (450 mg) after trituration with pentane as a white solid. MS (ESI): m/z=267.1 [ M+H]$^+$.

E. Synthesis of the Intermediate Aminodihydropyrimidinones E

General Procedure

To a solution of the amino ester C (21 mmole) in DMF (50 ml) was added subsequently the thiourea (23.1 mmole), DIEA (84 mmole) and EDCI (29.4 mmole) and the mixture was stirred at 22° C. for 16 h. The mixture was partitioned between water and ethyl acetate, the organic layer was dried, evaporated and the residue was chromatographed on silica using cyclohexane/ethyl acetate (2:1) to give the pure aminodihydropyrimidinone E.

Intermediate E1: Starting from (S)-3-amino-3-(3-nitro-phenyl)-butyric acid methyl ester (21 mmole) and tert-butyl [(methylamino)carbonothioyl]carbamate, the product [(S)-1,4-dimethyl-4-(3-nitro-phenyl)-6-oxo-1,4,5,6-tetrahydro-pyrimidin-2-yl]-carbamic acid tert-butyl ester (7.22 g) was obtained as white solid. MS (ESI): m/z=361.4 [M–H]$^-$.

Intermediate E2: Starting from (S)-3-amino-3-(3-nitro-phenyl)-pentanoic acid methyl ester (1.2 mmole) and tert-butyl [(methylamino)carbonothioyl]carbamate, the product [(S)-4-ethyl-1-methyl-4-(3-nitro-phenyl)-6-oxo-1,4,5,6-tetrahydro-pyrimidin-2-yl]-carbamic acid tert-butyl ester (372 mg) was obtained as white solid. MS (ESI): m/z=375.4 [ M–H]$^-$.

Intermediate E3: Starting from (S)-3-amino-3-(2-fluoro-5-nitro-phenyl)-butyric acid methyl ester (14.8 mmole) and tert-butyl [(methylamino)carbonothioyl]carbamate, the product [(S)-4-(2-fluoro-5-nitro-phenyl)-1,4-dimethyl-6-oxo-1,4,5,6-tetrahydro-pyrimidin-2-yl]-carbamic acid tert-butyl ester (3.13 g) was obtained as pale yellow foam. MS (ESI): m/z=381.2 [ M+H]$^+$.

Intermediate E4: Starting from (S)-3-amino-3-(3-nitro-phenyl)-butyric acid methyl ester (0.42 mmole) and tert-butyl [(ethylamino)carbonothioyl]carbamate the product [(S)-1-ethyl-4-methyl-4-(3-nitro-phenyl)-6-oxo-1,4,5,6-tetrahydro-pyrimidin-2-yl]-carbamic acid tert-butyl ester (153 mg) was obtained as colourless oil. MS (ESI): m/z=377.3 [ M+H]$^+$.

Intermediate E5: Starting from (S)-3-amino-3-(3-nitro-phenyl)-butyric acid methyl ester (0.42 mmole) and tert-butyl [(benzylamino)carbonothioyl]carbamate, the product [(S)-1-benzyl-4-methyl-4-(3-nitro-phenyl)-6-oxo-1,4,5,6-tetrahydro-pyrimidin-2-yl]-carbamic acid tert-butyl ester (165 mg) was obtained as a white solid. MS (ESI): m/z=439.3 [ M+H]$^+$.

Intermediate E6: Starting from (S)-3-amino-3-(5-nitro-pyridin-3-yl)-butyric acid methyl ester (0.66 mmole) and tert-butyl [(methylamino)carbonothioyl]carbamate the product

[(S)-1,4-dimethyl-4-(5-nitro-pyridin-3-yl)-6-oxo-1,4,5,6-tetrahydro-pyrimidin-2-yl]-carbamic acid tert-butyl ester (225 mg) was obtained as white solid. MS (ESI): m/z=362.1 [M–H]⁻.

Intermediate E7: Starting from (S)-3-amino-3-(2-fluoro-5-nitro-phenyl)-2,2-dimethyl-butyric acid methyl ester and tert-butyl [(methylamino)carbonothioyl]carbamate (1.8 mmole), the product [(S)-4-(2-fluoro-5-nitro-phenyl)-1,4,5,5-tetramethyl-6-oxo-1,4,5,6-tetrahydro-pyrimidin-2-yl]-carbamic acid tert-butyl ester (31 mg) was obtained as pale yellow oil. MS (ESI): m/z=407.3 [M–H]⁻. A second fraction contained [(R)-4-(2-methoxy-5-nitro-phenyl)-1,4,5,5-tetramethyl-6-oxo-1,4,5,6-tetrahydro-pyrimidin-2-yl]-carbamic acid tert-butyl ester (270 mg) as a white solid. MS (ESI): m/z=419.3 [ M–H]⁻.

F. Synthesis of the Intermediate Anilines F
General Procedure

A suspension of the aminodihydropyrimidinone E (12.1 mmole) in ethylalcohol (100 ml) and Pd/C (10%, 400 mg) was hydrogenated at normal pressure and 22° C. for 2 h. The mixture was filtered, the filtrate evaporated and the residue was chromatographed on silica using cyclohexane/ethyl acetate (1:1) to give the pure aniline F.

Intermediate F1: Starting from [(S)-1,4-dimethyl-4-(3-nitro-phenyl)-6-oxo-1,4,5,6-tetrahydro-pyrimidin-2-yl]-carbamic acid tert-butyl ester (12.1 mmole), the product [(S)-4-(3-amino-phenyl)-1,4-dimethyl-6-oxo-1,4,5,6-tetrahydro-pyrimidin-2-yl]-carbamic acid tert-butyl ester (4.02 g) was obtained as a white amorphous solid. MS (ESI): m/z=331.4 [M–H]⁻.

Intermediate F2: Starting from [(S)-4-ethyl-1-methyl-4-(3-nitro-phenyl)-6-oxo-1,4,5,6-tetrahydro-pyrimidin-2-yl]-carbamic acid tert-butyl ester (1.0 mmole), the product [(S)-4-(3-amino-phenyl)-4-ethyl-1-methyl-6-oxo-1,4,5,6-tetrahydro-pyrimidin-2-yl]-carbamic acid tert-butyl ester (372 mg) was obtained as a white amorphous solid. MS (ESI): m/z=347.2 calc [M+H]⁺.

Intermediate F3: Starting from [(S)-4-(2-fluoro-5-nitro-phenyl)-1,4-dimethyl-6-oxo-1,4,5,6-tetrahydro-pyrimidin-2-yl]-carbamic acid tert-butyl ester (14.8 mmole), the product [(S)-4-(5-amino-2-fluoro-phenyl)-1,4-dimethyl-6-oxo-1,4,5,6-tetrahydro-pyrimidin-2-yl]-carbamic acid tert-butyl ester (2.60 g) was obtained as a white amorphous solid. MS (ESI): m/z=349.4 calc [M–H]⁻.

Intermediate F4: Starting from [(S)-1-ethyl-4-methyl-4-(3-nitro-phenyl)-6-oxo-1,4,5,6-tetrahydro-pyrimidin-2-yl]-carbamic acid tert-butyl ester (0.40 mmole), the product [(S)-4-(3-amino-phenyl)-1-ethyl-4-methyl-6-oxo-1,4,5,6-tetrahydro-pyrimidin-2-yl]-carbamic acid tert-butyl ester (123 mg) was obtained as a colourless oil. MS (ESI): m/z=347.3 [ M+H]⁺.

Intermediate F5: Starting from [(S)-1-benzyl-4-methyl-4-(3-nitro-phenyl)-6-oxo-1,4,5,6-tetrahydro-pyrimidin-2-yl]-carbamic acid tert-butyl ester (0.98 mmole), the crude material was chromatographed on silica using n-heptane/ethyl acetate (5:2) to give a first fraction containing [(S)-4-(3-amino-phenyl)-1-benzyl-4-methyl-6-oxo-1,4,5,6-tetrahydro-pyrimidin-2-yl]-carbamic acid tert-butyl ester (224 mg) as a colourless foam. MS (ESI): m/z=409.4 [ M+H]⁺ The second fraction was obtained using ethyl acetate/MeOH (9:1) to give [(S)-4-(3-amino-phenyl)-4-methyl-6-oxo-1,4,5,6-tetrahydro-pyrimidin-2-yl]-carbamic acid tert-butyl ester (49 mg) as a colourless oil. MS (ESI): m/z=319.3 [ M+H]⁺.

Intermediate F6: Starting from [(S)-1,4-dimethyl-4-(5-nitro-pyridin-3-yl)-6-oxo-1,4,5,6-tetrahydro-pyrimidin-2-yl]-carbamic acid tert-butyl ester (0.62 mmole), the product [(S)-4-(5-amino-pyridin-3-yl)-1,4-dimethyl-6-oxo-1,4,5,6-tetrahydro-pyrimidin-2-yl]-carbamic acid tert-butyl ester (113 mg) was obtained as a pale yellow solid. MS (ESI): m/z=334.4 [ M+H]⁺.

Intermediate F7: Starting from [(S)-4-(2-fluoro-5-nitro-phenyl)-1,4,5,5-tetramethyl-6-oxo-1,4,5,6-tetrahydro-pyrimidin-2-yl]-carbamic acid tert-butyl ester (0.08 mmole), the product [(S)-4-(5-amino-2-fluoro-phenyl)-1,4,5,5-tetramethyl-6-oxo-1,4,5,6-tetrahydro-pyrimidin-2-yl]-carbamic acid tert-butyl ester (29 mg) was obtained as a colorless oil. MS (ESI): m/z=379.3 [ M+H]⁺.

G. Synthesis of the Amides G and H
General Procedure

To a solution of the aniline F (0.30 mmole) in DMF (2 ml) was added subsequently HATU (0.60 mmole), the carbonic acid (0.45 mmole) and DIEA (0.90 mmole) and stirring was continued at 22° C. for 16 h. The mixture was purified on prep. RP-18 HPLC using a gradient of acetonitrile and water (containing 0.1% of formic acid) to give the t-butyloxycarbonyl protected intermediate G.

The t-butyloxycarbonyl protected intermediate G was treated with a solution of HCl in 1,4-dioxane (4 M, 1 ml) and MeOH (1 ml) or with a mixture of CF₃COOH (1 ml) in dichloromethane (18 ml) and stirring was continued at 22° C. for 16 h. The mixture was evaporated and the residue was purified either by trituration with ethyl ether to give the pure amide H as the HCl or CF₃COOH salt or by prep. RP-18 HPLC using a gradient of acetonitrile and water (containing 0.1% of formic acid) to give the pure amide H as the formic acid salt in yields of 10-90%.

xample 1

5-Methyl-thiophene-2-carboxylic acid [3-((S)-2-amino-1,4-dimethyl-6-oxo-1,4,5,6-tetrahydro-pyrimidin-4-yl)-phenyl]-amide; salt with HCl

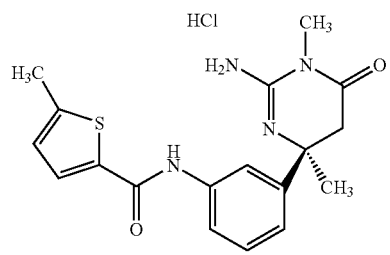 [SMILES: Cl ; Cc1ccc(C(=O)Nc2cccc([C@]3(C)CC(=O)N(C)C(N)=N3)c2)s1]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 5-methyl-thiophene-2-carboxylic acid followed by deprotection of the intermediate yielded the title compound as a colourless solid. MS (ESI): m/z=357.1 [ M+H]⁺.

Example 2

5-Chloro-thiophene-2-carboxylic acid [3-((S)-2-amino-1,4-dimethyl-6-oxo-1,4,5,6-tetrahydro-pyrimidin-4-yl)-phenyl]amide; salt with HCl

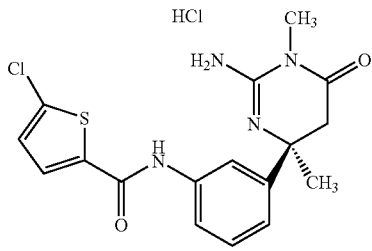 [SMILES: Cl ; CN1C(=O)C[C@@](C)(c2cccc(NC(=O)c3ccc(Cl)s3)c2)N=C1N]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 5-chloro-thiophene-2-carboxylic acid followed by deprotection of the intermediate yielded the title compound as a colourless solid. MS (ESI): m/z=377.3 [ M+H]$^+$.

Example 3

2,5-Dimethyl-thiophene-3-carboxylic acid [3-((S)-2-amino-1,4-dimethyl-6-oxo-1,4,5,6-tetrahydro-pyrimidin-4-yl)-phenyl]amide; salt with HCl

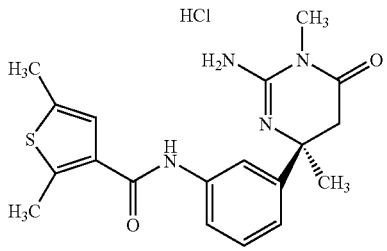 [SMILES: Cl ; Cc1cc(C(=O)Nc2cccc([C@]3(C)CC(=O)N(C)C(N)=N3)c2)c(C)s1]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 2,5-dimethyl-thiophene-3-carboxylic acid followed by deprotection of the intermediate yielded the title compound as a pale yellow oil. MS (ESI): m/z=371.1 [ M+H]$^+$

Example 4

2,5-Dimethyl-oxazole-4-carboxylic acid [3-((S)-2-amino-1,4-dimethyl-6-oxo-1,4,5,6-tetrahydro-pyrimidin-4-yl)-phenyl]amide; salt with HCl

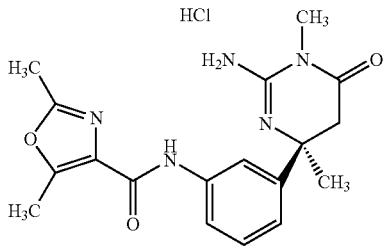 [SMILES: Cl ; Cc1nc(C(=O)Nc2cccc([C@]3(C)CC(=O)N(C)C(N)=N3)c2)c(C)o1]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 2,5-dimethyl-oxazole-4-carboxylic acid followed by deprotection of the intermediate yielded the title compound as a colourless oil. MS (ESI): m/z=356.2 [ M+H]$^+$.

Example 5

2,4-Dimethyl-oxazole-5-carboxylic acid [3-((S)-2-amino-1,4-dimethyl-6-oxo-1,4,5,6-tetrahydro-pyrimidin-4-yl)-phenyl]amide; salt with HCl

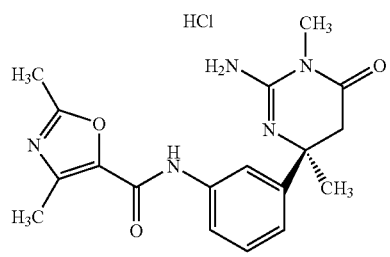 [SMILES: Cl ; Cc1nc(C)c(C(=O)Nc2cccc([C@]3(C)CC(=O)N(C)C(N)=N3)c2)o1]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 2,4-dimethyl-oxazole-5-carboxylic acid followed by deprotection of the intermediate yielded the title compound as an off-white solid. MS (ESI): m/z=356.1 [ M+H]$^+$

Example 6

3-Methyl-isoxazole-5-carboxylic acid [3-((S)-2-amino-1,4-dimethyl-6-oxo-1,4,5,6-tetrahydro-pyrimidin-4-yl)-phenyl]amide; salt with formic acid

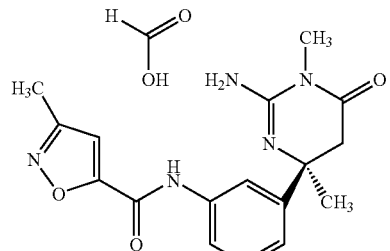

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 3-methyl-isoxazole-5-carboxylic acid followed by deprotection of the intermediate yielded the title compound as a colourless solid. MS (ESI): m/z=342.2 [ M+H]$^+$

Example 7

1,5-Dimethyl-1H-pyrazole-3-carboxylic acid [3-((S)-2-amino-1,4-dimethyl-6-oxo-1,4,5,6-tetrahydro-pyrimidin-4-yl)-phenyl]amide; salt with HCl

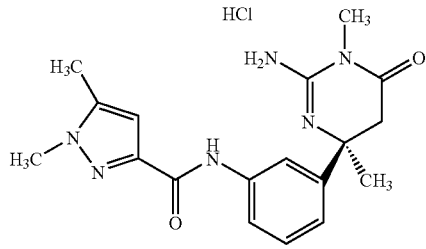 [SMILES: Cl ; Cc1cc(C(=O)Nc2cccc([C@]3(C)CC(=O)N(C)C(N)=N3)c2)nn1C]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 1,5-dimethyl-1H-pyrazole-3-carboxylic acid followed by deprotection of the intermediate yielded the title compound as a pale yellow solid. MS (ESI): m/z=355.2 [ M+H]$^+$

Example 8

2,5-Dimethyl-2H-pyrazole-3-carboxylic acid [3-((S)-2-amino-1,4-dimethyl-6-oxo-1,4,5,6-tetrahydro-pyrimidin-4-yl)-phenyl]amide; salt with HCl

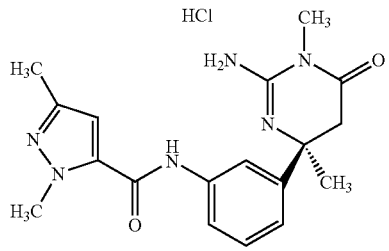 [SMILES: Cl ; Cc1cc(C(=O)Nc2cccc([C@]3(C)CC(=O)N(C)C(N)=N3)c2)n(C)n1]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 2,5-dimethyl-2H-pyrazole-3-carboxylic acid followed by deprotection of the intermediate yielded the title compound as a pale yellow solid. MS (ESI): m/z=355.2 [ M+H]$^+$.

Example 9

Imidazo[1,2-a]pyridine-2-carboxylic acid [3-((S)-2-amino-1,4-dimethyl-6-oxo-1,4,5,6-tetrahydro-pyrimidin-4-yl)-phenyl]amide; salt with HCl

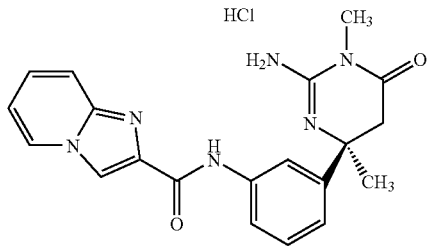 [SMILES: Cl ; CN1C(=O)C[C@@](C)(c2cccc(NC(=O)c3cn4ccccc4n3)c2)N=C1N]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and imidazo[1,2-a]pyridine-2-carboxylic acid followed by deprotection of the intermediate yielded the title compound as a pale yellow solid. MS (ESI): m/z=377.4 [ M+H]$^+$

Example 10

5-Chloro-pyridine-2-carboxylic acid [3-((S)-2-amino-1,4-dimethyl-6-oxo-1,4,5,6-tetrahydro-pyrimidin-4-yl)-phenyl]amide; salt with HCl

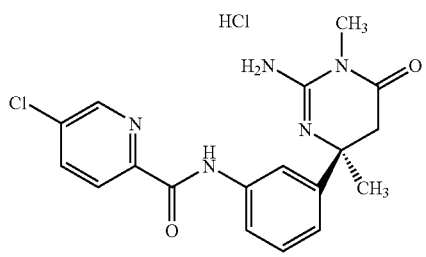 [SMILES: Cl ; CN1C(=O)C[C@@](C)(c2cccc(NC(=O)c3ccc(Cl)cn3)c2)N=C1N]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 5-chloro-pyridine-2-carboxylic acid followed by deprotection of the intermediate yielded the title compound as a white solid. MS (ESI): m/z=372.1 [ M+H]$^+$.

Example 11

5-Trifluoromethyl-pyridine-2-carboxylic acid [3-((S)-2-amino-1,4-dimethyl-6-oxo-1,4,5,6-tetrahydro-pyrimidin-4-yl)-phenyl]amide; salt with formic acid

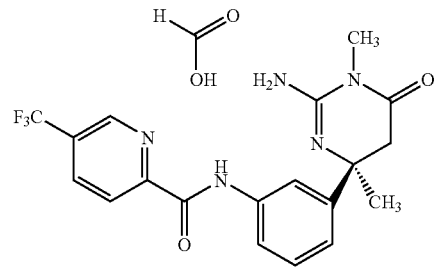 [SMILES: CN1C(=O)C[C@@](C)(c2cccc(NC(=O)c3ccc(C(F)(F)F)cn3)c2)N=C1N ; O=CO]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 5-trifluoromethyl-pyridine-2-carboxylic acid followed by deprotection of the intermediate yielded the title compound as a colourless foam. MS (ESI): m/z=406.3 [ M+H]$^+$.

Example 12

5-Methyl-pyridine-2-carboxylic acid [3-((S)-2-amino-1,4-dimethyl-6-oxo-1,4,5,6-tetrahydro-pyrimidin-4-yl)-phenyl]amide; salt with HCl

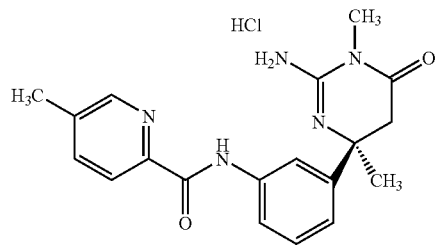 [SMILES: Cc1ccc(C(=O)Nc2cccc([C@]3(C)CC(=O)N(C)C(N)=N3)c2)nc1 ; Cl]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 5-methyl-pyridine-2-carboxylic acid followed by deprotection of the intermediate yielded the title compound as a pale yellow solid. MS (ESI): m/z=352.3 [ M+H]$^+$.

Example 13

Pyridine-2-carboxylic acid [3-((S)-2-amino-1,4-dimethyl-6-oxo-1,4,5,6-tetrahydro-pyrimidin-4-yl)-phenyl]-amide; salt with formic acid

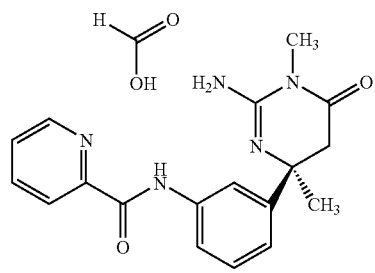 [SMILES: CN1C(=O)C[C@@](C)(c2cccc(NC(=O)c3ccccn3)c2)N=C1N ; O=CO]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and pyridine-2-carboxylic acid followed by deprotection of the intermediate yielded the title compound as a colourless foam. MS (ESI): m/z=338.2 [ M+H]$^+$.

Example 14

5-Methoxy-pyridine-2-carboxylic acid [3-((S)-2-amino-1,4-dimethyl-6-oxo-1,4,5,6-tetrahydro-pyrimidin-4-yl)-phenyl]-amide; salt with formic acid

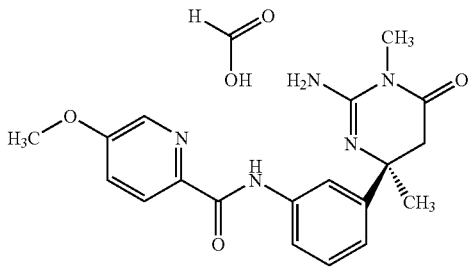 [SMILES: COc1ccc(C(=O)Nc2cccc([C@]3(C)CC(=O)N(C)C(N)=N3)c2)nc1 ; O=CO]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 5-methoxy-pyridine-2-carboxylic acid followed by deprotection of the intermediate yielded the title compound as a colourless solid. MS (ESI): m/z=368.2 [ M+H]$^+$.

Example 15

5-Cyano-pyridine-2-carboxylic acid [3-((S)-2-amino-1,4-dimethyl-6-oxo-1,4,5,6-tetrahydro-pyrimidin-4-yl)-phenyl]amide; salt with HCl

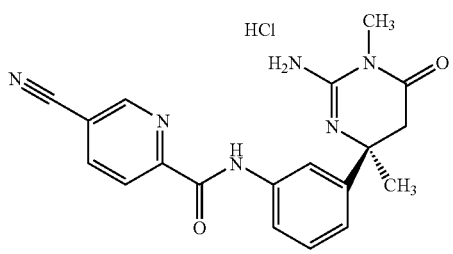 [SMILES: CN1C(=O)C[C@@](C)(c2cccc(NC(=O)c3ccc(C#N)cn3)c2)N=C1N ; Cl]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 5-cyano-pyridine-2-carboxylic acid followed by deprotection of the intermediate yielded the title compound as a colourless solid. MS (ESI): m/z=363.2 [ M+H]$^+$.

Example 16

5-Hydroxymethyl-pyridine-2-carboxylic acid [3-((S)-2-amino-1,4-dimethyl-6-oxo-1,4,5,6-tetrahydro-pyrimidin-4-yl)-phenyl]amide; salt with HCl

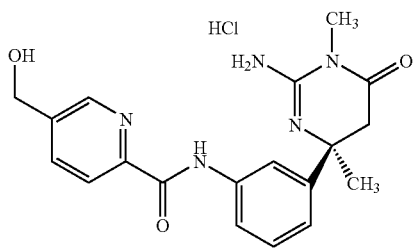 [SMILES: CN1C(=O)C[C@@](C)(c2cccc(NC(=O)c3ccc(CO)cn3)c2)N=C1N ; Cl]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 5-hydroxymethyl-pyridine-2-carboxylic acid (prepared according to G. Galley et al., Int. patent appl. WO2006005486) followed by deprotection of the intermediate yielded the title compound as a colourless foam. MS (ESI): m/z=368.2 [M+H]$^+$.

Example 17

N-[3-((S)-2-Amino-1,4-dimethyl-6-oxo-1,4,5,6-tetrahydro-pyrimidin-4-yl)-phenyl]-4-methyl-benzamide; salt with formic acid

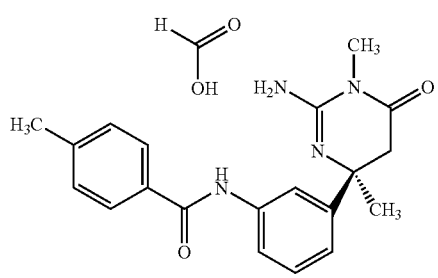 [SMILES: Cc1ccc(C(=O)Nc2cccc([C@]3(C)CC(=O)N(C)C(N)=N3)c2)cc1 ; O=CO]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 4-methyl-benzoic acid followed by deprotection of the intermediate yielded the title compound as a colourless solid. MS (ESI): m/z=351.3 [M+H]$^+$.

Example 18

N-[3-((S)-2-Amino-1,4-dimethyl-6-oxo-1,4,5,6-tetrahydro-pyrimidin-4-yl)-phenyl]-4-chloro-benzamide; salt with HCl

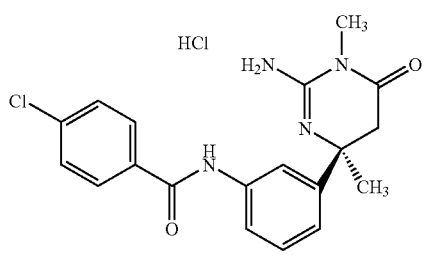 [SMILES: CN1C(=O)C[C@@](C)(c2cccc(NC(=O)c3ccc(Cl)cc3)c2)N=C1N ; Cl]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 4-chloro-benzoic acid followed by deprotection of the intermediate yielded the title compound as a colourless oil. MS (ESI): m/z=371.1 [M+H]$^+$.

Example 19

N-[3-((S)-2-Amino-1,4-dimethyl-6-oxo-1,4,5,6-tetrahydro-pyrimidin-4-yl)-phenyl]-6-chloro-nicotinamide; salt with HCl

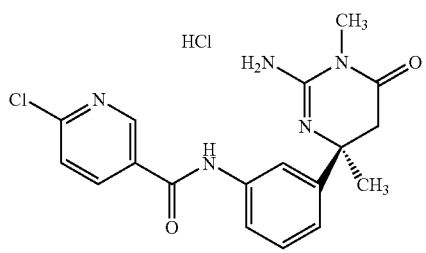 [SMILES: CN1C(=O)C[C@@](C)(c2cccc(NC(=O)c3ccc(Cl)nc3)c2)N=C1N ; Cl]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 6-chloro-nicotinic acid followed by deprotection of the intermediate yielded the title compound as a colourless oil. MS (ESI): m/z=372.1 [M+H]$^+$.

Example 20

5-Chloro-pyrimidine-2-carboxylic acid [3-((S)-2-amino-1,4-dimethyl-6-oxo-1,4,5,6-tetrahydro-pyrimidin-4-yl)-phenyl]amide; salt with HCl

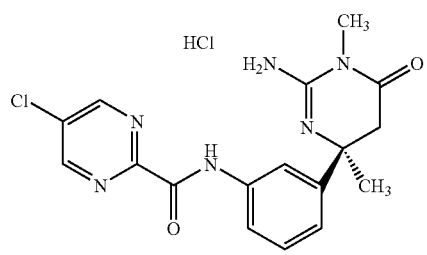 [SMILES: CN1C(=O)C[C@@](C)(c2cccc(NC(=O)c3ncc(Cl)cn3)c2)N=C1N ; Cl]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 5-chloro-pyrimidine-2-carboxylic acid followed by deprotection of the intermediate yielded the title compound as a pale yellow solid. MS (ESI): m/z=373.1 [M+H]$^+$.

Example 21

1-Methyl-6-oxo-1,6-dihydro-pyridazine-3-carboxylic acid [3-((S)-2-amino-1,4-dimethyl-6-oxo-1,4,5,6-tetrahydro-pyrimidin-4-yl)-phenyl]amide; salt with HCl

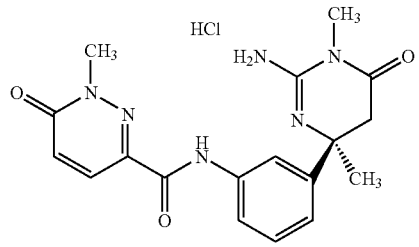 [SMILES: CN1C(=O)C[C@@](C)(c2cccc(NC(=O)c3ccc(=O)n(C)n3)c2)N=C1N ; Cl]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 1-methyl-6-oxo-1,6-dihydro-pyridazine-3-carboxylic acid followed by deprotection of the intermediate yielded the title compound as a pale brown solid. MS (ESI): m/z=369.2 [M+H]$^+$.

Example 22

5-Methyl-pyrazine-2-carboxylic acid [3-((S)-2-amino-1,4-dimethyl-6-oxo-1,4,5,6-tetrahydro-pyrimidin-4-yl)-phenyl]amide; salt with formic acid

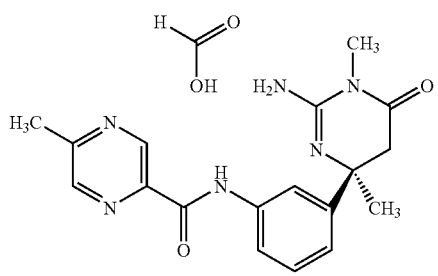 [SMILES: Cc1cnc(C(=O)Nc2cccc([C@]3(C)CC(=O)N(C)C(N)=N3)c2)cn1 ; O=CO]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 5-methyl-pyrazine-2-carboxylic acid followed by deprotection of the intermediate yielded the title compound as a colourless foam. MS (ESI): m/z=353.2 [M+H]$^+$.

Example 23

6-Oxo-1,6-dihydro-pyridazine-3-carboxylic acid [3-((S)-2-amino-1,4-dimethyl-6-oxo-1,4,5,6-tetrahydro-pyrimidin-4-yl)-phenyl]amide; salt with HCl

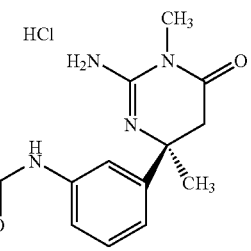

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 6-oxo-1,6-dihydro-pyridazine-3-carboxylic acid followed by deprotection of the intermediate yielded the title compound as a pale brown solid. MS (ESI): m/z=355.2 [M+H]$^+$

Example 24

6-Methyl-pyrazine-2-carboxylic acid [3-((S)-2-amino-1,4-dimethyl-6-oxo-1,4,5,6-tetrahydro-pyrimidin-4-yl)-phenyl]amide; salt with HCl

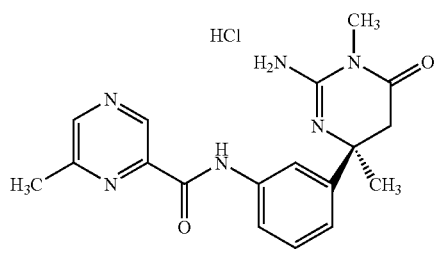 [SMILES: Cc1cncc(C(=O)Nc2cccc([C@]3(C)CC(=O)N(C)C(N)=N3)c2)n1 ; Cl]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 6-methyl-pyrazine-2-carboxylic acid followed by deprotection of the intermediate yielded the title compound as a pale yellow solid. MS (ESI): m/z=353.2 [M+H]$^+$

Example 25

5-Chloro-pyrazine-2-carboxylic acid [3-((S)-2-amino-1,4-dimethyl-6-oxo-1,4,5,6-tetrahydro-pyrimidin-4-yl)-phenyl]-amide; salt with formic acid

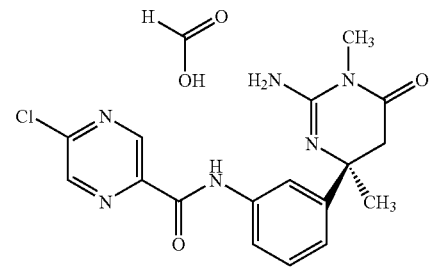 [SMILES: CN1C(=O)C[C@@](C)(c2cccc(NC(=O)c3cnc(Cl)cn3)c2)N=C1N ; O=CO]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 5-chloro-pyrazine-2-carboxylic acid followed by deprotection of the intermediate yielded the title compound as a colourless oil. MS (ESI): m/z=373.2 [M+H]$^+$.

Example 26

N-[3-((S)-2-Amino-1,4-dimethyl-6-oxo-1,4,5,6-tetrahydro-pyrimidin-4-yl)-phenyl]-isonicotinamide; salt with formic acid

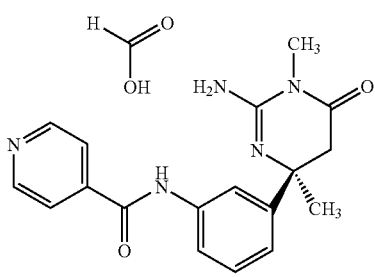 [SMILES: CN1C(=O)C[C@@](C)(c2cccc(NC(=O)c3ccncc3)c2)N=C1N ; O=CO]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and isonicotinic acid followed by deprotection of the intermediate yielded the title compound as a colourless solid. MS (ESI): m/z=338.2 [M+H]$^+$.

Example 27

5-Fluoro-pyridine-2-carboxylic acid [3-((S)-2-amino-1,4-dimethyl-6-oxo-1,4,5,6-tetrahydro-pyrimidin-4-yl)-phenyl]amide; salt with formic acid

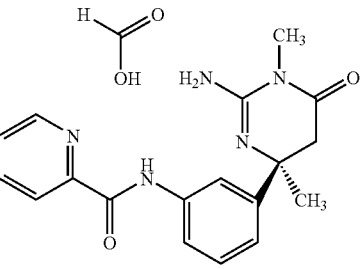

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 5-fluoro-pyridine-2-carboxylic acid followed by deprotection of the intermediate yielded the title compound as a colourless solid. MS (ESI): m/z=356.1 [M+H]$^+$.

Example 28

3-Chloro-pyridine-2-carboxylic acid [3-((S)-2-amino-1,4-dimethyl-6-oxo-1,4,5,6-tetrahydro-pyrimidin-4-yl)-phenyl]amide; salt with HCl

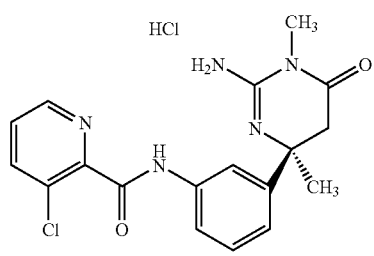 [SMILES: CN1C(=O)C[C@@](C)(c2cccc(NC(=O)c3ncccc3Cl)c2)N=C1N ; Cl]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 3-chloro-pyridine-2-carboxylic acid followed by deprotection of the intermediate yielded the title compound as a pale yellow solid. MS (ESI): m/z=372.2 [M+H]$^+$.

Example 29

4-Chloro-pyridine-2-carboxylic acid [3-((S)-2-amino-1,4-dimethyl-6-oxo-1,4,5,6-tetrahydro-pyrimidin-4-yl)-phenyl]-amide

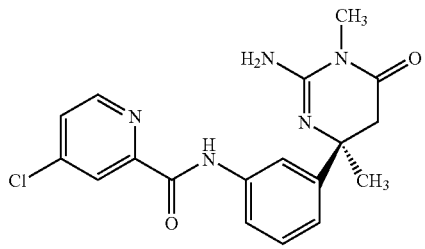 [SMILES: CN1C(=O)C[C@@](C)(c2cccc(NC(=O)c3cc(Cl)ccn3)c2)N=C1N]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 4-chloro-pyridine-2-carboxylic acid followed by deprotection of the intermediate yielded the title compound as a colourless solid. MS (ESI): m/z=372.1 [M+H]$^+$.

Example 30

4-Methyl-pyridine-2-carboxylic acid [3-((S)-2-amino-1,4-dimethyl-6-oxo-1,4,5,6-tetrahydro-pyrimidin-4-yl)-phenyl]-amide; salt with formic acid

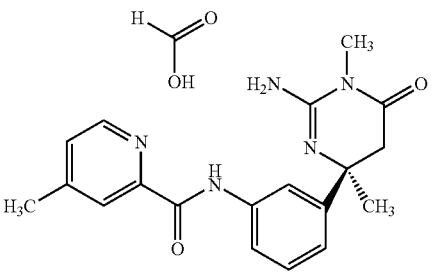 [SMILES: Cc1ccnc(C(=O)Nc2cccc([C@]3(C)CC(=O)N(C)C(N)=N3)c2)c1 ; O=CO]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 4-methyl-pyridine-2-carboxylic acid followed by deprotection of the intermediate yielded the title compound as a colourless solid. MS (ESI): m/z=352.2 [M+H]$^+$.

Example 31

6-Chloro-pyridine-2-carboxylic acid [3-((S)-2-amino-1,4-dimethyl-6-oxo-1,4,5,6-tetrahydro-pyrimidin-4-yl)-phenyl]-amide; salt with formic acid

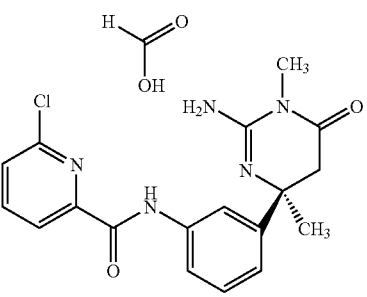 [SMILES: CN1C(=O)C[C@@](C)(c2cccc(NC(=O)c3cccc(Cl)n3)c2)N=C1N ; O=CO]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 6-chloro-pyridine-2-carboxylic acid followed by deprotection of the intermediate yielded the title compound as a colourless solid. MS (ESI): m/z=372.1 [M+H]$^+$.

Example 32

6-Methyl-pyridine-2-carboxylic acid [3-((S)-2-amino-1,4-dimethyl-6-oxo-1,4,5,6-tetrahydro-pyrimidin-4-yl)-phenyl]-amide; salt with formic acid

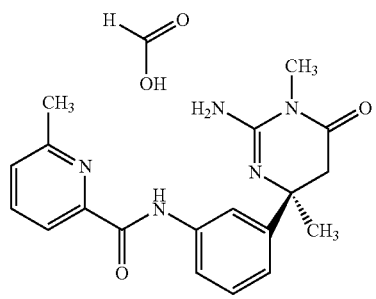 [SMILES: Cc1cccc(C(=O)Nc2cccc([C@]3(C)CC(=O)N(C)C(N)=N3)c2)n1 ; O=CO]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 6-methyl-pyridine-2-carboxylic acid followed by deprotection of the intermediate yielded the title compound as a colourless solid. MS (ESI): m/z=352.3 [ M+H]$^+$.

Example 33

N-[3-((S)-2-Amino-1,4-dimethyl-6-oxo-1,4,5,6-tetrahydro-pyrimidin-4-yl)-phenyl]-nicotinamide

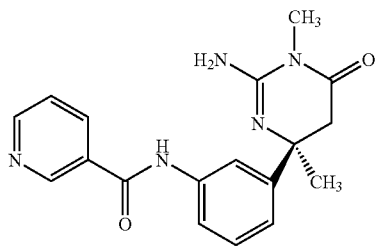 [SMILES: CN1C(=O)C[C@@](C)(c2cccc(NC(=O)c3cccnc3)c2)N=C1N]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and nicotinic acid followed by deprotection of the intermediate yielded the title compound as a colourless solid. MS (ESI): m/z=338.4 [ M+H]$^+$.

Example 34

N-[3-((S)-2-Amino-1,4-dimethyl-6-oxo-1,4,5,6-tetrahydro-pyrimidin-4-yl)-phenyl]-benzamide; salt with formic acid

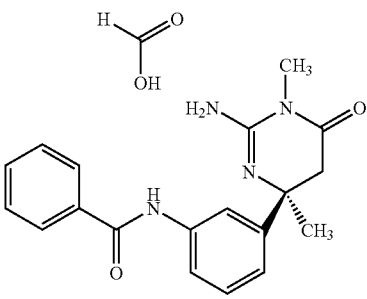 [SMILES: CN1C(=O)C[C@@](C)(c2cccc(NC(=O)c3ccccc3)c2)N=C1N ; O=CO]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and benzoic acid followed by deprotection of the intermediate yielded the title compound as a colourless solid. MS (ESI): m/z=337.2 [ M+H]$^+$

Example 35

2-Methyl-pyrimidine-5-carboxylic acid [3-((S)-2-amino-1,4-dimethyl-6-oxo-1,4,5,6-tetrahydro-pyrimidin-4-yl)-phenyl]-amide; salt with CF$_3$COOH

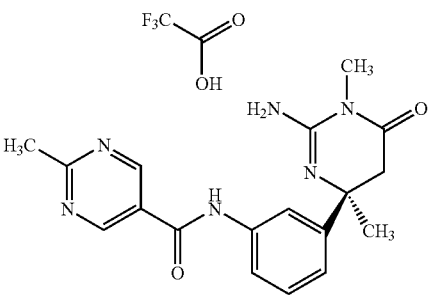 [SMILES: Cc1ncc(C(=O)Nc2cccc([C@]3(C)CC(=O)N(C)C(N)=N3)c2)cn1 ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 2-methyl-pyrimidine-5-carboxylic acid followed by deprotection of the intermediate yielded the title compound as a white solid. MS (ESI): m/z=353.4 [ M+H]$^+$.

Example 36

5-Oxo-4,5-dihydro-pyrazine-2-carboxylic acid [3-((S)-2-amino-1,4-dimethyl-6-oxo-1,4,5,6-tetrahydro-pyrimidin-4-yl)-phenyl]-amide; salt with CF$_3$COOH

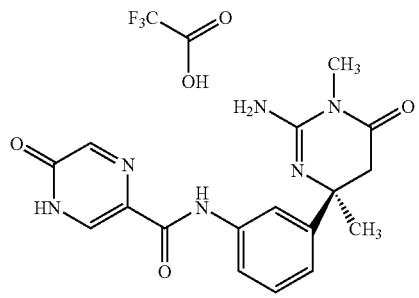 [SMILES: CN1C(=O)C[C@@](C)(c2cccc(NC(=O)c3c[nH]c(=O)cn3)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 5-oxo-4,5-dihydro-pyrazine-2-carboxylic acid followed by deprotection of the intermediate yielded the title compound as a pale brown solid. MS (ESI): m/z=355.4 [ M+H]$^+$.

Example 37

3-Phenyl-pyridine-2-carboxylic acid [3-((S)-2-amino-1,4-dimethyl-6-oxo-1,4,5,6-tetrahydro-pyrimidin-4-yl)-phenyl]-amide; salt with CF$_3$COOH

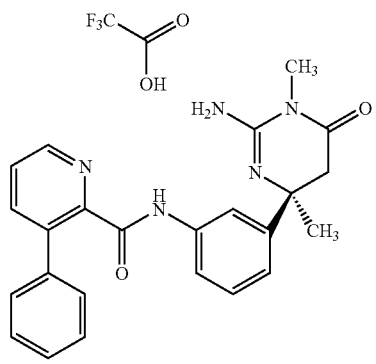 [SMILES: CN1C(=O)C[C@@](C)(c2cccc(NC(=O)c3ncccc3-c3ccccc3)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 3-phenyl-pyridine-2-carboxylic acid followed by deprotection of the intermediate yielded the title compound as a white solid. MS (ESI): m/z=414.3 [ M+H]$^+$.

Example 38

2-Methyl-oxazole-4-carboxylic acid [3-((S)-2-amino-1,4-dimethyl-6-oxo-1,4,5,6-tetrahydro-pyrimidin-4-yl)-phenyl]-amide; salt with CF$_3$COOH

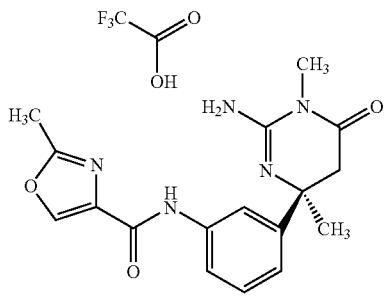 [SMILES: Cc1nc(C(=O)Nc2cccc([C@]3(C)CC(=O)N(C)C(N)=N3)c2)co1 ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester from experiment F1 and 2-methyl-oxazole-4-carboxylic acid followed by deprotection of the intermediate yielded the title compound as a white solid. MS (ESI): m/z=342.2 [ M+H]$^+$.

Example 39

5-Chloro-pyridine-2-carboxylic acid [3-((S)-2-amino-4-ethyl-1-methyl-6-oxo-1,4,5,6-tetrahydro-pyrimidin-4-yl)-phenyl]-amide; salt with CF$_3$COOH

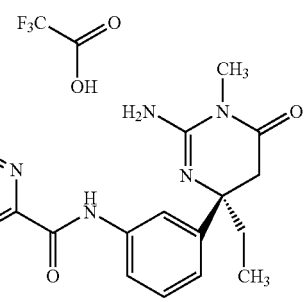

The coupling of [(S)-4-(3-amino-phenyl)-4-ethyl-1-methyl-6-oxo-1,4,5,6-tetrahydro-pyrimidin-2-yl]-carbamic acid tert-butyl ester from experiment F2 and 5-chloro-pyridine-2-carboxylic acid followed by deprotection of the intermediate yielded the title compound as a pale brown solid. MS (ESI): m/z=386.4 [ M+H]$^+$.

Example 40

Pyridine-2-carboxylic acid [3-((S)-2-amino-4-ethyl-1-methyl-6-oxo-1,4,5,6-tetrahydro-pyrimidin-4-yl)-phenyl]-amide; salt with CF₃COOH

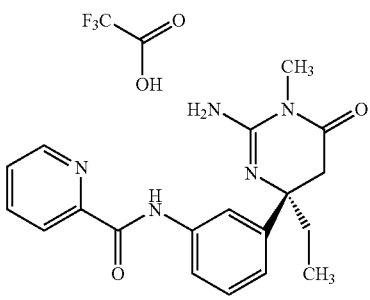 [SMILES: CC[C@@]1(c2cccc(NC(=O)c3ccccn3)c2)CC(=O)N(C)C(N)=N1 ; O=C(O)C(F)(F)F]

The coupling of [(S)-4-(3-amino-phenyl)-4-ethyl-1-methyl-6-oxo-1,4,5,6-tetrahydro-pyrimidin-2-yl]-carbamic acid tert-butyl ester from experiment F2 and pyridine-2-carboxylic acid followed by deprotection of the intermediate yielded the title compound as a white solid. MS (ESI): m/z=352.4 [M+H]⁺.

Example 41

5-Chloro-thiophene-2-carboxylic acid [3-((S)-2-amino-4-ethyl-1-methyl-6-oxo-1,4,5,6-tetrahydro-pyrimidin-4-yl)-phenyl]-amide; salt with CF₃COOH

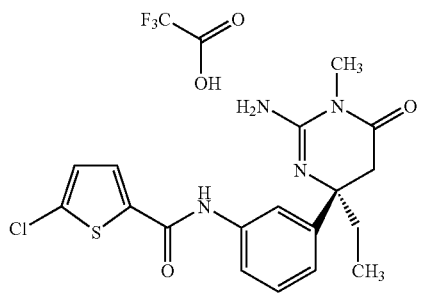 [SMILES: CC[C@@]1(c2cccc(NC(=O)c3ccc(Cl)s3)c2)CC(=O)N(C)C(N)=N1 ; O=C(O)C(F)(F)F]

The coupling of [(S)-4-(3-amino-phenyl)-4-ethyl-1-methyl-6-oxo-1,4,5,6-tetrahydro-pyrimidin-2-yl]-carbamic acid tert-butyl ester from experiment F2 and 5-chloro-thiophene-2-carboxylic acid followed by deprotection of the intermediate yielded the title compound as a white solid. MS (ESI): m/z=391.3 [M+H]⁺.

Example 42

6-Chloro-pyridine-2-carboxylic acid [3-((S)-2-amino-4-ethyl-1-methyl-6-oxo-1,4,5,6-tetrahydro-pyrimidin-4-yl)-phenyl]-amide; salt with CF₃COOH

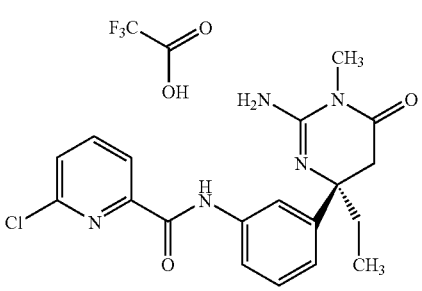 [SMILES: CC[C@@]1(c2cccc(NC(=O)c3cccc(Cl)n3)c2)CC(=O)N(C)C(N)=N1 ; O=C(O)C(F)(F)F]

The coupling of [(S)-4-(3-amino-phenyl)-4-ethyl-1-methyl-6-oxo-1,4,5,6-tetrahydro-pyrimidin-2-yl]-carbamic acid tert-butyl ester from experiment F2 and 6-chloro-pyridine-2-carboxylic acid followed by deprotection of the intermediate yielded the title compound as a white solid. MS (ESI): m/z=386.4 [M+H]⁺.

Example 43

3-Chloro-pyridine-2-carboxylic acid [3-((S)-2-amino-4-ethyl-1-methyl-6-oxo-1,4,5,6-tetrahydro-pyrimidin-4-yl)-phenyl]-amide; salt with CF₃COOH

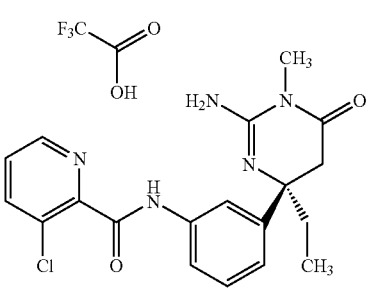 [SMILES: CC[C@@]1(c2cccc(NC(=O)c3ncccc3Cl)c2)CC(=O)N(C)C(N)=N1 ; O=C(O)C(F)(F)F]

The coupling of [(S)-4-(3-amino-phenyl)-4-ethyl-1-methyl-6-oxo-1,4,5,6-tetrahydro-pyrimidin-2-yl]-carbamic acid tert-butyl ester from experiment F2 and 3-chloro-pyridine-2-carboxylic acid followed by deprotection of the intermediate yielded the title compound as a white solid. MS (ESI): m/z=386.4 [M+H]⁺.

Example 44

5-Chloro-pyrimidine-2-carboxylic acid [3-((S)-2-amino-4-ethyl-1-methyl-6-oxo-1,4,5,6-tetrahydro-pyrimidin-4-yl)-phenyl]-amide; salt with CF₃COOH

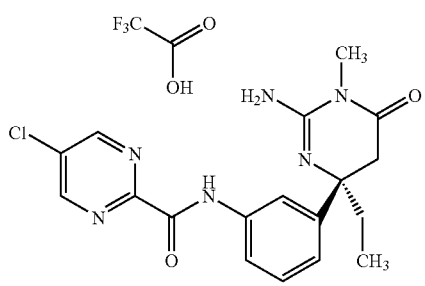 [SMILES: CC[C@@]1(c2cccc(NC(=O)c3ncc(Cl)cn3)c2)CC(=O)N(C)C(N)=N1 ; O=C(O)C(F)(F)F]

The coupling of [(S)-4-(3-amino-phenyl)-4-ethyl-1-methyl-6-oxo-1,4,5,6-tetrahydro-pyrimidin-2-yl]-carbamic acid tert-butyl ester from experiment F2 and 5-Chloro-pyrimidine-2-carboxylic acid followed by deprotection of the intermediate yielded the title compound as a white solid. MS (ESI): m/z=387.3 [ M+H]⁺.

Example 45

5-Chloro-pyridine-2-carboxylic acid [3-((S)-2-amino-1,4-dimethyl-6-oxo-1,4,5,6-tetrahydro-pyrimidin-4-yl)-4-fluoro-phenyl]amide; salt with HCl

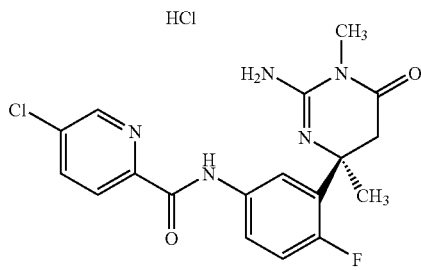 [SMILES: Cl ; CN1C(=O)C[C@@](C)(c2cc(NC(=O)c3ccc(Cl)cn3)ccc2F)N=C1N]

The coupling of [(S)-4-(5-amino-2-fluoro-phenyl)-1,4-dimethyl-6-oxo-1,4,5,6-tetrahydro-pyrimidin-2-yl]-carbamic acid tert-butyl ester from experiment F3 and 5-chloro-pyridine-2-carboxylic acid followed by deprotection of the intermediate yielded the title compound as a white solid. MS (ESI): m/z=390.3 [ M+H]⁺.

Example 46

5-Chloro-pyrimidine-2-carboxylic acid [3-((S)-2-amino-1,4-dimethyl-6-oxo-1,4,5,6-tetrahydro-pyrimidin-4-yl)-4-fluoro-phenyl]amide; salt with CF₃COOH

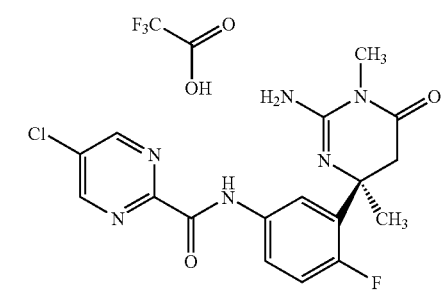 [SMILES: CN1C(=O)C[C@@](C)(c2cc(NC(=O)c3ncc(Cl)cn3)ccc2F)N=C1N ; O=C(O)C(F)(F)F]

The coupling of [(S)-4-(5-amino-2-fluoro-phenyl)-1,4-dimethyl-6-oxo-1,4,5,6-tetrahydro-pyrimidin-2-yl]-carbamic acid tert-butyl ester from experiment F3 and 5-chloro-pyrimidine-2-carboxylic acid followed by deprotection of the intermediate yielded the title compound as a white solid. MS (ESI): m/z=391.3 [ M+H]⁺.

Example 47

Pyridine-2-carboxylic acid [3-((S)-2-amino-1,4-dimethyl-6-oxo-1,4,5,6-tetrahydro-pyrimidin-4-yl)-4-fluoro-phenyl]amide; salt with CF₃COOH

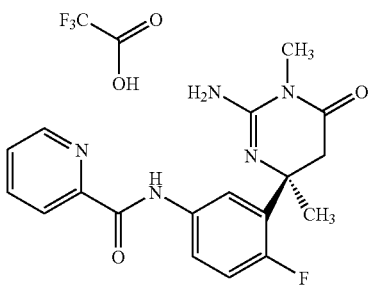 [SMILES: CN1C(=O)C[C@@](C)(c2cc(NC(=O)c3ccccn3)ccc2F)N=C1N ; O=C(O)C(F)(F)F]

The coupling of [(S)-4-(5-amino-2-fluoro-phenyl)-1,4-dimethyl-6-oxo-1,4,5,6-tetrahydro-pyrimidin-2-yl]-carbamic acid tert-butyl ester from experiment F3 and pyridine-2-carboxylic acid followed by deprotection of the intermediate yielded the title compound as a white solid. MS (ESI): m/z=356.3 [ M+H]⁺.

Example 48

5-Trifluoromethyl-pyridine-2-carboxylic acid [3-((S)-2-amino-1,4-dimethyl-6-oxo-1,4,5,6-tetrahydro-pyrimidin-4-yl)-4-fluoro-phenyl]amide; salt with CF$_3$COOH

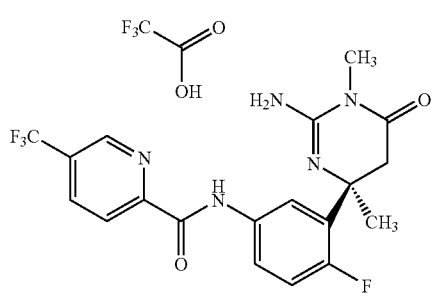 [SMILES: CN1C(=O)C[C@@](C)(c2cc(NC(=O)c3ccc(C(F)(F)F)cn3)ccc2F)N=C1N ; O=C(O)C(F)(F)F]

The coupling of [(S)-4-(5-amino-2-fluoro-phenyl)-1,4-dimethyl-6-oxo-1,4,5,6-tetrahydro-pyrimidin-2-yl]-carbamic acid tert-butyl ester from experiment F3 and 5-trifluoromethyl-pyridine-2-carboxylic acid followed by deprotection of the intermediate yielded the title compound as a white solid. MS (ESI): m/z=424.3 [ M+H]$^+$.

Example 49

5-Chloro-pyridine-2-carboxylic acid [3-((S)-2-amino-1-ethyl-4-methyl-6-oxo-1,4,5,6-tetrahydro-pyrimidin-4-yl)-phenyl]amide; salt with HCl

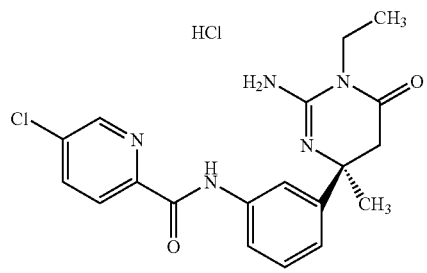 [SMILES: CCN1C(=O)C[C@@](C)(c2cccc(NC(=O)c3ccc(Cl)cn3)c2)N=C1N ; Cl]

The coupling of [(S)-4-(3-amino-phenyl)-1-ethyl-4-methyl-6-oxo-1,4,5,6-tetrahydro-pyrimidin-2-yl]-carbamic acid tert-butyl ester from experiment F4 and 5-chloro-pyridine-2-carboxylic acid followed by deprotection of the intermediate yielded the title compound as a pale yellow solid. MS (ESI): m/z=386.2 [ M+H]$^+$.

Example 50

5-Chloro-pyridine-2-carboxylic acid [3-((S)-2-amino-1-benzyl-4-methyl-6-oxo-1,4,5,6-tetrahydro-pyrimidin-4-yl)-phenyl]amide; salt with CF$_3$COOH

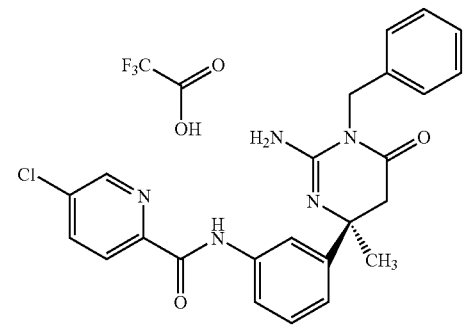 [SMILES: C[C@@]1(c2cccc(NC(=O)c3ccc(Cl)cn3)c2)CC(=O)N(Cc2ccccc2)C(N)=N1 ; O=C(O)C(F)(F)F]

The coupling of [(S)-4-(3-amino-phenyl)-1-benzyl-4-methyl-6-oxo-1,4,5,6-tetrahydro-pyrimidin-2-yl]-carbamic acid tert-butyl ester from experiment F5, first fraction and 5-chloro-pyridine-2-carboxylic acid followed by deprotection of the intermediate yielded the title compound as a pale brown solid. MS (ESI): m/z=448.3 [ M+H]$^+$.

Example 51

5-Chloro-pyridine-2-carboxylic acid [3-((S)-2-amino-4-methyl-6-oxo-1,4,5,6-tetrahydro-pyrimidin-4-yl)-phenyl]amide; salt with CF$_3$COOH

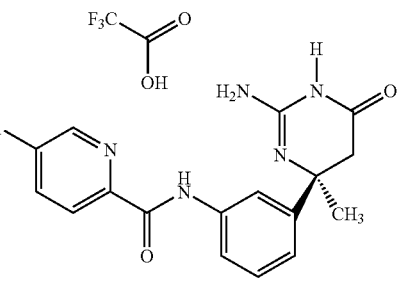

The coupling of [(S)-4-(3-amino-phenyl)-4-methyl-6-oxo-1,4,5,6-tetrahydro-pyrimidin-2-yl]-carbamic acid tert-butyl ester from experiment F5, second fraction and 5-chloro-pyridine-2-carboxylic acid followed by deprotection of the intermediate yielded the title compound as a pale brown solid. MS (ESI): m/z=358.2 [ M+H]$^+$.

Example 52

5-Chloro-pyridine-2-carboxylic acid [5-((S)-2-amino-1,4-dimethyl-6-oxo-1,4,5,6-tetrahydro-pyrimidin-4-yl)-pyridin-3-yl]-amide; salt with CF$_3$COOH

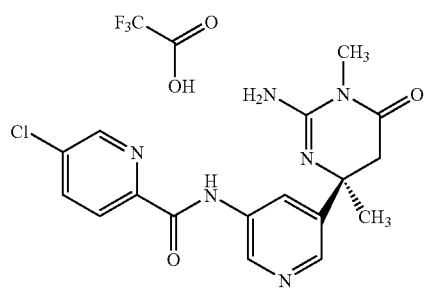 [SMILES: CN1C(=O)C[C@@](C)(c2cncc(NC(=O)c3ccc(Cl)cn3)c2)N=C1N ; O=C(O)C(F)(F)F]

The coupling of [(S)-4-(5-amino-pyridin-3-yl)-1,4-dimethyl-6-oxo-1,4,5,6-tetrahydro-pyrimidin-2-yl]-carbamic acid tert-butyl ester from experiment F6 and 5-chloro-pyridine-2-carboxylic acid followed by deprotection of the intermediate yielded the title compound as a white solid. MS (ESI): m/z=373.1 [ M+H]$^+$.

Example 53

5-Chloro-pyridine-2-carboxylic acid [3-((S)-2-amino-1,4,5,5-tetramethyl-6-oxo-1,4,5,6-tetrahydro-pyrimidin-4-yl)-4-fluoro-phenyl]amide; salt with CF$_3$COOH

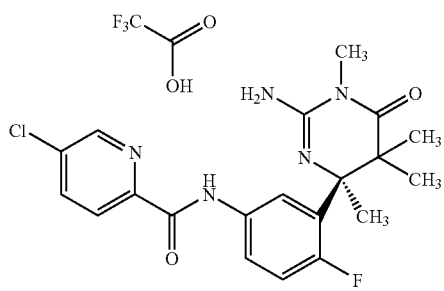 [SMILES: CN1C(=O)C(C)(C)[C@@](C)(c2cc(NC(=O)c3ccc(Cl)cn3)ccc2F)N=C1N ; O=C(O)C(F)(F)F]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester from experiment F7 and 5-chloro-pyridine-2-carboxylic acid followed by deprotection of the intermediate yielded the title compound as a white solid. MS (ESI): m/z=418.3 [ M+H]$^+$.

Example 54

3,6-Dichloro-pyridine-2-carboxylic acid [3-((S)-2-amino-1,4-dimethyl-6-oxo-1,4,5,6-tetrahydro-pyrimidin-4-yl)-phenyl]-amide; salt with trifluoro-acetic acid

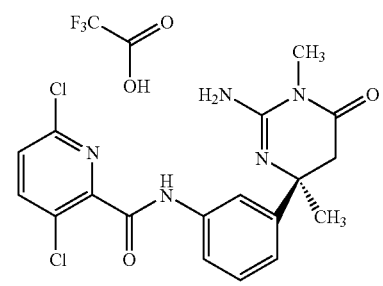 [SMILES: CN1C(=O)C[C@@](C)(c2cccc(NC(=O)c3nc(Cl)ccc3Cl)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 3,6-dichloro-pyridine-2-carboxylic acid followed by deprotection of the intermediate yielded the title compound as a pale yellow solid. MS (ESI): m/z=408.3 [ M+H]$^+$.

Example 55

3-Propoxy-pyridine-2-carboxylic acid [3-((S)-2-amino-1,4-dimethyl-6-oxo-1,4,5,6-tetrahydro-pyrimidin-4-yl)-phenyl]-amide; salt with trifluoro-acetic acid

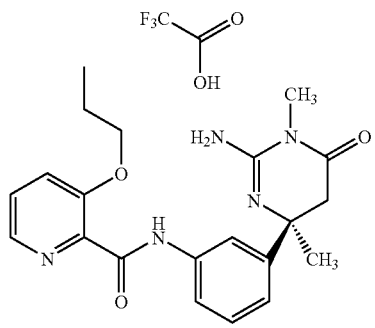

The coupling of [(S)-4-(3-amino-phenyl)-1,4-dimethyl-6-oxo-1,4,5,6-tetrahydro-pyrimidin-2-yl]-carbamic acid tert-butyl ester and 3-propoxy-pyridine-2-carboxylic acid followed by deprotection of the intermediate yielded the title compound as a pale yellow solid. MS (ESI): m/z=396.3 [ M+H]$^+$.

Example 56

Isoquinoline-1-carboxylic acid [3-((S)-2-amino-1,4-dimethyl-6-oxo-1,4,5,6-tetrahydro-pyrimidin-4-yl)-phenyl]-amide; salt with trifluoro-acetic acid

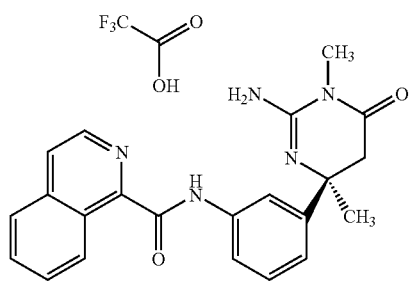 [SMILES: CN1C(=O)C[C@@](C)(c2cccc(NC(=O)c3nccc4ccccc34)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and isoquinoline-1-carboxylic acid followed by deprotection of the intermediate yielded the title compound as a yellow semi solid. MS (ESI): m/z=388.3 [ M+H]$^+$.

Example 57

Isoquinoline-3-carboxylic acid [3-((S)-2-amino-1,4-dimethyl-6-oxo-1,4,5,6-tetrahydro-pyrimidin-4-yl)-phenyl]amide; salt with trifluoro-acetic acid

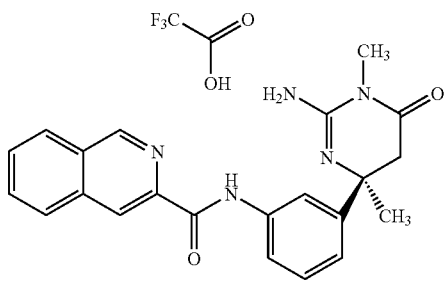 [SMILES: CN1C(=O)C[C@@](C)(c2cccc(NC(=O)c3cc4ccccc4cn3)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and isoquinoline-3-carboxylic acid followed by deprotection of the intermediate yielded the title compound as a colorless semi solid. MS (ESI): m/z=388.3 [ M+H]$^+$.

Example 58

Quinoline-2-carboxylic acid [3-((S)-2-amino-1,4-dimethyl-6-oxo-1,4,5,6-tetrahydro-pyrimidin-4-yl)-phenyl]-amide; salt with trifluoro-acetic acid

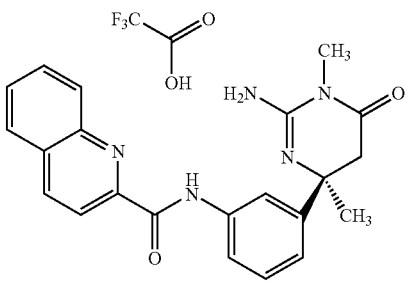 [SMILES: CN1C(=O)C[C@@](C)(c2cccc(NC(=O)c3ccc4ccccc4n3)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and quinoline-2-carboxylic acid followed by deprotection of the intermediate yielded the title compound as a yellow semi solid. MS (ESI): m/z=388.3 [ M+H]$^+$.

Example 59

Thieno[3,2-b]pyridine-5-carboxylic acid [3-((S)-2-amino-1,4-dimethyl-6-oxo-1,4,5,6-tetrahydro-pyrimidin-4-yl)-phenyl]-amide; salt with trifluoro-acetic acid

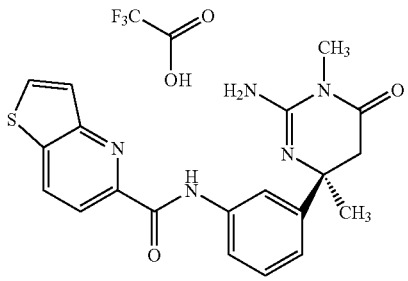 [SMILES: CN1C(=O)C[C@@](C)(c2cccc(NC(=O)c3ccc4sccc4n3)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and thieno[3,2-b]pyridine-5-carboxylic acid (prepared according to Gronowitz, S. et al., Acta Chemica Scand., Series B: Organic Chemistry and Biochemistry (1975), B29 (2), 233) followed by deprotection of the intermediate yielded the title compound as a pale yellow semi solid. MS (ESI): m/z=394.2 [ M+H]$^+$.

Example 60

Thieno[2,3-c]pyridine-7-carboxylic acid [3-((S)-2-amino-1,4-dimethyl-6-oxo-1,4,5,6-tetrahydro-pyrimidin-4-yl)-phenyl]-amide; salt with trifluoro-acetic acid

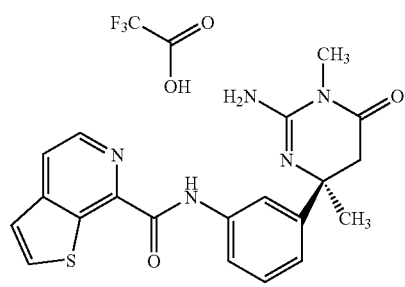 [SMILES: CN1C(=O)C[C@@](C)(c2cccc(NC(=O)c3nccc4ccsc34)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and thieno[2,3-c]pyridine-7-carboxylic acid (prepared according to Frohn, Mike et al., Bioorg. & Med. Chem. Lett. (2008), 18(18) 5023) followed by deprotection of the intermediate yielded the title compound as a yellow semi solid. MS (ESI): m/z=394.2 [ M+H]$^+$.

Example 61

3-Phenylsulfanyl-pyridine-2-carboxylic acid [3-((S)-2-amino-1,4-dimethyl-6-oxo-1,4,5,6-tetrahydro-pyrimidin-4-yl)-phenyl]-amide; salt with trifluoro-acetic acid

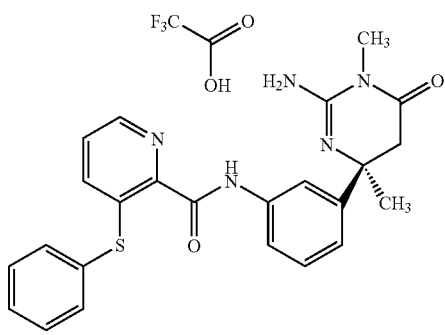 [SMILES: CN1C(=O)C[C@@](C)(c2cccc(NC(=O)c3ncccc3Sc3ccccc3)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl and 3-phenylsulfanyl-pyridine-2-carboxylic acid (prepared according to Blank, Benjamin et al., J. Med. Chem. (1974), 17(10) 1065) followed by deprotection of the intermediate yielded the title compound as a yellow semi solid. MS (ESI): m/z=446.2 [ M+H]$^+$.

Example 62

3-Trifluoromethyl-pyridine-2-carboxylic acid [3-((S)-2-amino-1,4-dimethyl-6-oxo-1,4,5,6-tetrahydro-pyrimidin-4-yl)-phenyl]-amide; salt with trifluoro-acetic acid

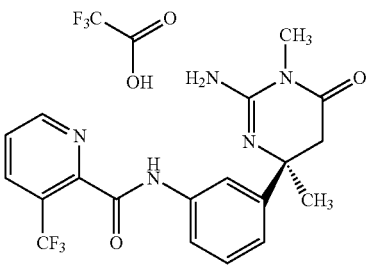 [SMILES: CN1C(=O)C[C@@](C)(c2cccc(NC(=O)c3ncccc3C(F)(F)F)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 3-trifluoromethyl-pyridine-2-carboxylic acid followed by deprotection of the intermediate yielded the title compound as a reddish semi solid. MS (ESI): m/z=406.4 [ M+H]$^+$.

Example 63

5-(2,2,2-Trifluoro-ethoxy)-pyridine-2-carboxylic acid [3-((S)-2-amino-1,4-dimethyl-6-oxo-1,4,5,6-tetrahydro-pyrimidin-4-yl)-phenyl]-amide; salt with trifluoro-acetic acid

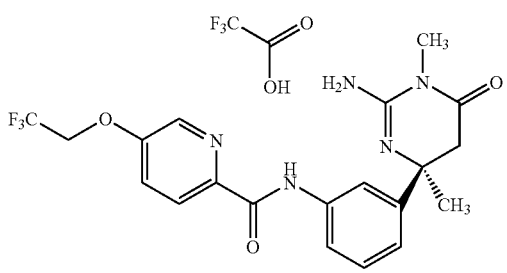 [SMILES: CN1C(=O)C[C@@](C)(c2cccc(NC(=O)c3ccc(OCC(F)(F)F)cn3)c2)N=C1N ; O=C(O)C(F)(F)F]

To a solution of 5-hydroxy-pyridine-2-carboxylic acid methyl ester (200 mg) in DMF (2.0 ml) was added at 22° C. NaH (55% in oil, 64 mg) and stirring was continued until gas evolution ceased. The suspension was cooled to 0° C. and treated with trifluoromethyl trifluoromethanesulphonate (728 mg) and stirring was continued at 22° C. for 2 h. The mixture was partitioned between saturated NaHCO$_3$ and ethyl acetate and the organic layer was dried and evaporated. The residue was chromatographed on silica using n-heptane/ethyl acetate (3:1) to give 5-(2,2,2-trifluoro-ethoxy)-pyridine-2-carboxylic acid methyl ester (216 mg) as a white solid. MS (ESI): m/z=236.3 [ M+H]$^+$.

A solution of 5-(2,2,2-trifluoro-ethoxy)-pyridine-2-carboxylic acid methyl ester (216 mg) in MeOH (1 ml) was treated with a solution of LiOH (78 mg) in water (0.1 ml) and stirring was continued at 22° C. for 2 h. The solution was evaporated and the residue triturated with 1N aqueous HCl. The suspension was filtered, the residue washed with water and dried to give 5-(2,2,2-trifluoro-ethoxy)-pyridine-2-carboxylic acid (125 mg) as a white solid. MS (ESI): m/z=220.1 [M−H]⁻.

The coupling of [(S)-4-(3-amino-phenyl)-1,4-dimethyl-6-oxo-1,4,5,6-tetrahydro-pyrimidin-2-yl]-carbamic acid tert-butyl ester and 5-(2,2,2-trifluoro-ethoxy)-pyridine-2-carboxylic acid followed by deprotection of the intermediate yielded the title compound as a pale yellow semi solid. MS (ESI): m/z=436.3 [M+H]⁺.

Example 64

3,5-Dichloro-pyridine-2-carboxylic acid [3-((S)-2-amino-1,4-dimethyl-6-oxo-1,4,5,6-tetrahydro-pyrimidin-4-yl)-phenyl]-amide; salt with trifluoro-acetic acid

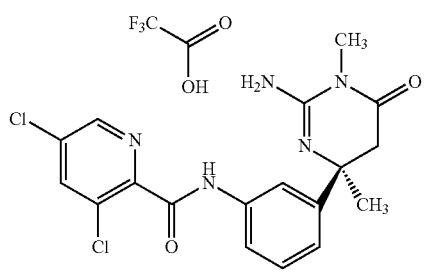 [SMILES: CN1C(=O)C[C@@](C)(c2cccc(NC(=O)c3ncc(Cl)cc3Cl)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 3,5-dichloro-pyridine-2-carboxylic acid followed by deprotection of the intermediate yielded the title compound as a pale yellow semi solid. MS (ESI): m/z=406.3 [M+H]⁺.

Example 65

3-Methoxy-pyridine-2-carboxylic acid [3-((S)-2-amino-1,4-dimethyl-6-oxo-1,4,5,6-tetrahydro-pyrimidin-4-yl)-phenyl]-amide; compound with trifluoro-acetic acid

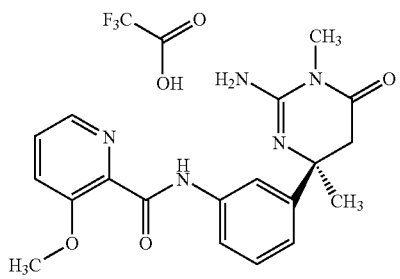 [SMILES: COc1cccnc1C(=O)Nc1cccc([C@]2(C)CC(=O)N(C)C(N)=N2)c1 ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 3-methoxy-pyridine-2-carboxylic acid followed by deprotection of the intermediate yielded the title compound as a pale brown solid. MS (ESI): m/z=368.2 [M+H]⁺.

Example 66

2-Trifluoromethyl-thiazole-4-carboxylic acid [3-((S)-2-amino-1,4-dimethyl-6-oxo-1,4,5,6-tetrahydro-pyrimidin-4-yl)-phenyl]-amide; compound with trifluoro-acetic acid

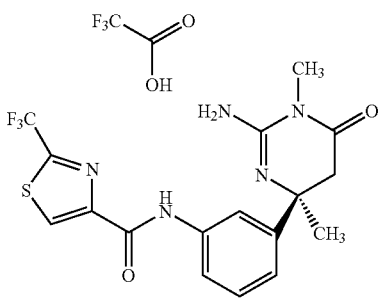 [SMILES: CN1C(=O)C[C@@](C)(c2cccc(NC(=O)c3csc(C(F)(F)F)n3)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 2-trifluoromethyl-thiazole-4-carboxylic acid followed by deprotection of the intermediate yielded the title compound as a white solid. MS (ESI): m/z=412.3 [M+H]⁺.

Example 67

2-Methyl-thiazole-4-carboxylic acid [3-((S)-2-amino-1,4-dimethyl-6-oxo-1,4,5,6-tetrahydro-pyrimidin-4-yl)-phenyl]-amide; compound with trifluoro-acetic acid

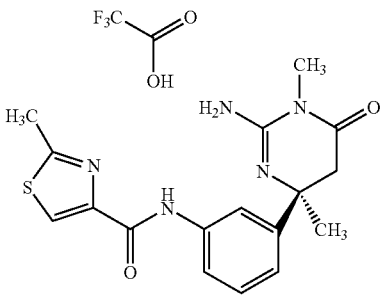

The coupling of [(S)-4-(3-amino-phenyl)-1,4-dimethyl-6-oxo-1,4,5,6-tetrahydro-pyrimidin-2-yl]-carbamic acid tert-butyl ester and 2-trifluoromethyl-thiazole-4-carboxylic acid followed by deprotection of the intermediate yielded the title compound as a white solid. MS (ESI): m/z=358.3 [M+H]⁺.

Example 68

Benzo[b]thiophene-2-carboxylic acid [3-((S)-2-amino-1,4-dimethyl-6-oxo-1,4,5,6-tetrahydro-pyrimidin-4-yl)-phenyl]-amide; compound with trifluoro-acetic acid

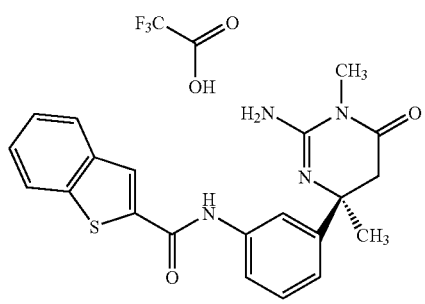 [SMILES: CN1C(=O)C[C@@](C)(c2cccc(NC(=O)c3cc4ccccc4s3)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and benzo[b]thiophene-2-carboxylic acid followed by deprotection of the intermediate yielded the title compound as a white solid. MS (ESI): m/z=393.2 [M+H]$^+$.

Example 69

1-Methyl-1H-pyrazole-3-carboxylic acid [3-((S)-2-amino-1,4-dimethyl-6-oxo-1,4,5,6-tetrahydro-pyrimidin-4-yl)-phenyl]-amide; compound with trifluoro-acetic acid

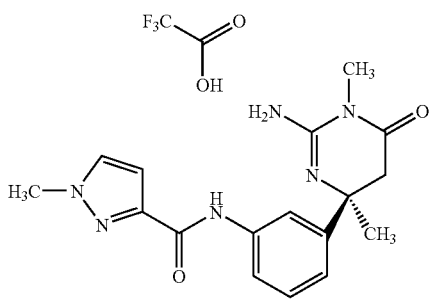 [SMILES: CN1C(=O)C[C@@](C)(c2cccc(NC(=O)c3ccn(C)n3)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 1-methyl-1H-pyrazole-3-carboxylic acid followed by deprotection of the intermediate yielded the title compound as a white solid. MS (ESI): m/z=341.3 [M+H]$^+$.

Example 70

3-Chloro-5-trifluoromethyl-pyridine-2-carboxylic acid [3-((S)-2-amino-1,4-dimethyl-6-oxo-1,4,5,6-tetrahydro-pyrimidin-4-yl)-phenyl]-amide; compound with trifluoro-acetic acid

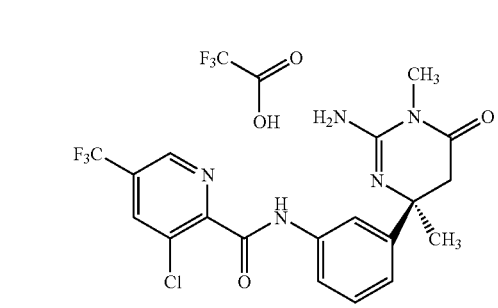 [SMILES: CN1C(=O)C[C@@](C)(c2cccc(NC(=O)c3ncc(C(F)(F)F)cc3Cl)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 3-chloro-5-trifluoromethyl-pyridine-2-carboxylic acid followed by deprotection of the intermediate yielded the title compound as a pale yellow solid. MS (ESI): m/z=440.3 [M+H]$^+$.

Example 71

2-Phenyl-oxazole-4-carboxylic acid [3-((S)-2-amino-1,4-dimethyl-6-oxo-1,4,5,6-tetrahydro-pyrimidin-4-yl)-phenyl]-amide; compound with trifluoro-acetic acid

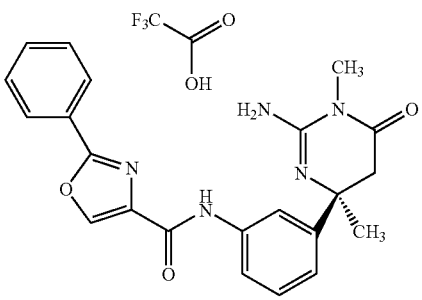 [SMILES: CN1C(=O)C[C@@](C)(c2cccc(NC(=O)c3coc(-c4ccccc4)n3)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 2-phenyl-oxazole-4-carboxylic acid followed by deprotection of the intermediate yielded the title compound as a white foam. MS (ESI): m/z=404.5 [M+H]$^+$.

Example 72

6-Chloro-3-trifluoromethyl-pyridine-2-carboxylic acid [3-((S)-2-amino-1,4-dimethyl-6-oxo-1,4,5,6-tetrahydro-pyrimidin-4-yl)-phenyl]-amide; compound with trifluoro-acetic acid

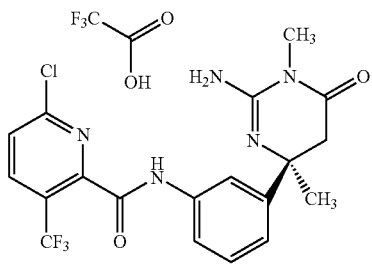 [SMILES: CN1C(=O)C[C@@](C)(c2cccc(NC(=O)c3nc(Cl)ccc3C(F)(F)F)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 6-chloro-3-trifluoromethyl-pyridine-2-carboxylic acid followed by deprotection of the intermediate yielded the title compound as a pale brown solid. MS (ESI): m/z=440.3 [M+H]$^+$.

Example 73

1-(2,2,2-Trifluoro-ethyl)-1H-pyrazole-3-carboxylic acid [3-((S)-2-amino-1,4-dimethyl-6-oxo-1,4,5,6-tetrahydro-pyrimidin-4-yl)-phenyl]-amide; compound with trifluoro-acetic acid

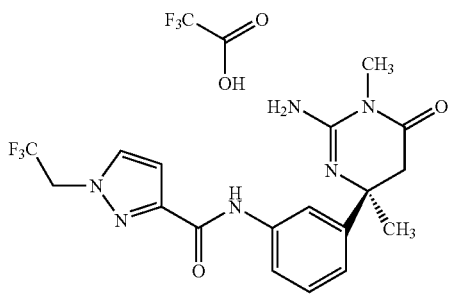 [SMILES: CN1C(=O)C[C@@](C)(c2cccc(NC(=O)c3ccn(CC(F)(F)F)n3)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 1-(2,2,2-trifluoro-ethyl)-1H-pyrazole-3-carboxylic acid followed by deprotection of the intermediate yielded the title compound as a pale red solid. MS (ESI): m/z=409.3 [M+H]$^+$.

Example 74

3-Ethoxy-5-trifluoromethyl-pyridine-2-carboxylic acid [3-((S)-2-amino-1,4-dimethyl-6-oxo-1,4,5,6-tetrahydro-pyrimidin-4-yl)-phenyl]-amide; compound with trifluoro-acetic acid

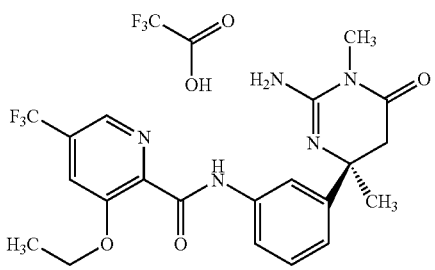 [SMILES: CCOc1cc(C(F)(F)F)cnc1C(=O)Nc1cccc([C@]2(C)CC(=O)N(C)C(N)=N2)c1 ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 3-ethoxy-5-trifluoromethyl-pyridine-2-carboxylic acid followed by deprotection of the intermediate yielded the title compound as a white solid. MS (ESI): m/z=450.2 [M+H]$^+$.

Example 75

5-Chloro-3-methyl-pyridine-2-carboxylic acid [3-((S)-2-amino-1,4-dimethyl-6-oxo-1,4,5,6-tetrahydro-pyrimidin-4-yl)-phenyl]-amide; compound with trifluoro-acetic acid

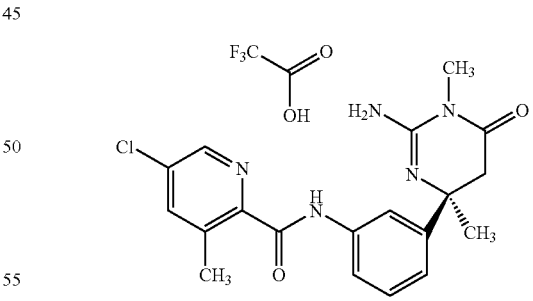

The coupling of [(S)-4-(3-amino-phenyl)-1,4-dimethyl-6-oxo-1,4,5,6-tetrahydro-pyrimidin-2-yl]-carbamic acid tert-butyl ester and 5-chloro-3-methyl-pyridine-2-carboxylic acid followed by deprotection of the intermediate yielded the title compound as a white solid. MS (ESI): m/z=386.2 [M+H]$^+$.

Example 76

5-(3-Trifluoromethyl-pyrazol-1-yl)-pyridine-2-carboxylic acid [3-((S)-2-amino-1,4-dimethyl-6-oxo-1,4,5,6-tetrahydro-pyrimidin-4-yl)-phenyl]-amide; compound with trifluoro-acetic acid

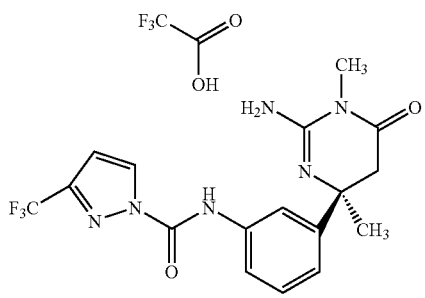 [SMILES: CN1C(=O)C[C@@](C)(c2cccc(NC(=O)n3ccc(C(F)(F)F)n3)c2)N=C1N ; O=C(O)C(F)(F)F]

A mixture of 5-chloro-pyridine-2-carboxylic acid methyl ester (1.37 g), 3-trifluoromethyl-1H-pyrazole (1.63 g) and powdered K2CO3 (1.67 g) in DMF (20 ml) was heated to 105° C. for 20 h. The mixture was evaporated and the residue partitioned between water and dichloromethane, the organic layer was washed with water, dried and evaporated. The residue was chromatographed on silica using n-heptane/ethyl acetate (gradient from 3:1 to 1:1) to give 5-(3-trifluoromethyl-pyrazol-1-yl)-pyridine-2-carboxylic acid methyl ester (70 mg) as a colorless solid. MS (ESI): m/z=272.1 [ M+H]$^+$.

To a solution of 5-(3-trifluoromethyl-pyrazol-1-yl)-pyridine-2-carboxylic acid methyl ester (67 mg) in MeOH (4 ml) and THF (0.5 ml) was added a solution of LiOH (23 mg) in water (1 ml) and stirring was continued at 22° C. for 22 h. The mixture was evaporated and the residue partitioned between 1 N aqueous HCl and ethyl acetate, the organic layer was washed with water, dried and evaporated to give 5-(3-trifluoromethyl-pyrazol-1-yl)-pyridine-2-carboxylic acid (63 mg) as a white solid. MS (ESI): m/z=255.9 [M−H]$^-$.

The coupling of [(S)-4-(3-amino-phenyl)-1,4-dimethyl-6-oxo-1,4,5,6-tetrahydro-pyrimidin-2-yl]-carbamic acid tert-butyl ester and 5-(3-trifluoromethyl-pyrazol-1-yl)-pyridine-2-carboxylic acid followed by deprotection of the intermediate yielded the title compound as a white solid. MS (ESI): m/z=472.2 [ M+H]$^+$.

Example 77

1,3-Dimethyl-1H-pyrazole-4-carboxylic acid [3-((S)-2-amino-1,4-dimethyl-6-oxo-1,4,5,6-tetrahydro-pyrimidin-4-yl)-phenyl]-amide; compound with trifluoro-acetic acid

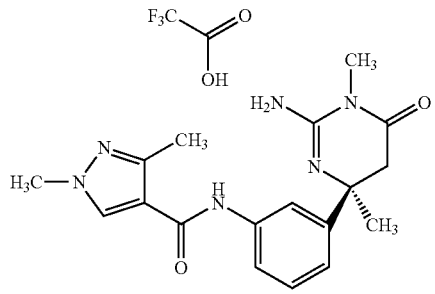 [SMILES: Cc1nn(C)cc1C(=O)Nc1cccc([C@]2(C)CC(=O)N(C)C(N)=N2)c1 ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 1,3-dimethyl-1H-pyrazole-4-carboxylic acid followed by deprotection of the intermediate yielded the title compound as a white solid. MS (ESI): m/z=355.2 [ M+H]$^+$.

Example 78

1H-Pyrrolo[2,3-b]pyridine-2-carboxylic acid [3-((S)-2-amino-1,4-dimethyl-6-oxo-1,4,5,6-tetrahydro-pyrimidin-4-yl)-phenyl]-amide; compound with trifluoro-acetic acid

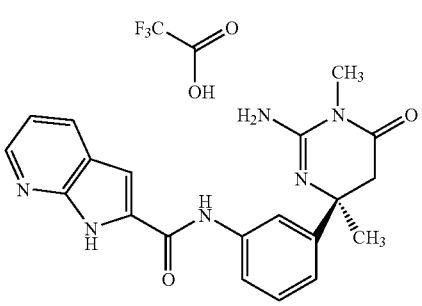 [SMILES: CN1C(=O)C[C@@](C)(c2cccc(NC(=O)c3cc4cccnc4[nH]3)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 1H-pyrrolo[2,3-b]pyridine-2-carboxylic acid followed by deprotection of the intermediate yielded the title compound as a yellow solid. MS (ESI): m/z=377.3 [ M+H]$^+$.

Example 79

2-Cyclopropyl-5-methyl-2H-pyrazole-3-carboxylic acid [3-((S)-2-amino-1,4-dimethyl-6-oxo-1,4,5,6-tetrahydro-pyrimidin-4-yl)-phenyl]-amide; compound with trifluoro-acetic acid

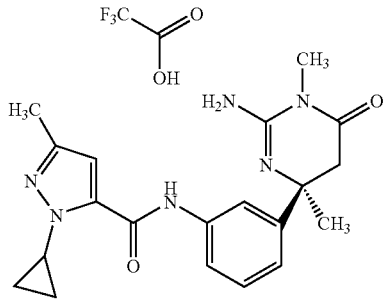 [SMILES: Cc1cc(C(=O)Nc2cccc([C@]3(C)CC(=O)N(C)C(N)=N3)c2)n(C2CC2)n1 ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 2-cyclopropyl-5-methyl-2H-pyrazole-3-carboxylic acid (prepared according to Kitamura, Shuji et al., int. patent Appl. WO 2005014576, followed by hydrolysis of the ester to the acid) followed by deprotection of the intermediate yielded the title compound as a white solid. MS (ESI): m/z=381.3 [ M+H]$^+$.

Example 80

N-[3-((S)-2-Amino-1,4-dimethyl-6-oxo-1,4,5,6-tetrahydro-pyrimidin-4-yl)-phenyl]-2-(1H-imidazol-2-yl)-benzamide; compound with trifluoro-acetic acid

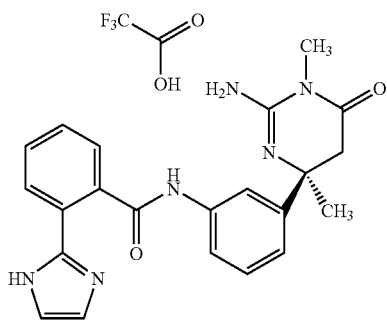 [SMILES: CN1C(=O)C[C@@](C)(c2cccc(NC(=O)c3ccccc3-c3ncc[nH]3)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 2-(1H-imidazol-2-yl)-benzoic acid followed by deprotection of the intermediate yielded the title compound as a white solid. MS (ESI): m/z=403.5 [M+H]$^+$.

Example 81

Isoxazole-3-carboxylic acid [3-((S)-2-amino-1,4-dimethyl-6-oxo-1,4,5,6-tetrahydro-pyrimidin-4-yl)-phenyl]-amide; compound with trifluoro-acetic acid

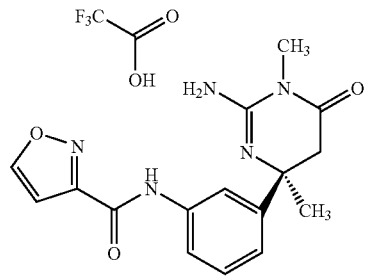 [SMILES: CN1C(=O)C[C@@](C)(c2cccc(NC(=O)c3ccon3)c2)N=C1N ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and isoxazole-3-carboxylic acid followed by deprotection of the intermediate yielded the title compound as a white solid. MS (ESI): m/z=328.2 [M+H]$^+$.

Example 82

5-Methyl-isoxazole-3-carboxylic acid [3-((S)-2-amino-1,4-dimethyl-6-oxo-1,4,5,6-tetrahydro-pyrimidin-4-yl)-phenyl]-amide; compound with trifluoro-acetic acid

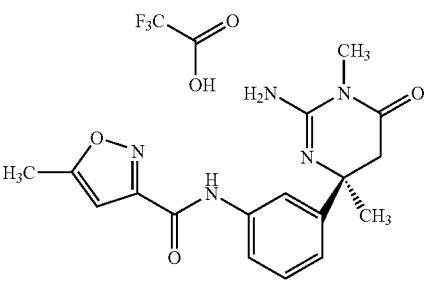 [SMILES: Cc1cc(C(=O)Nc2cccc([C@]3(C)CC(=O)N(C)C(N)=N3)c2)no1 ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 5-methyl-isoxazole-3-carboxylic acid followed by deprotection of the intermediate yielded the title compound as a white solid. MS (ESI): m/z=342.5 [M+H]$^+$.

Example 83

5-Ethyl-pyridine-2-carboxylic acid [3-((S)-2-amino-1,4-dimethyl-6-oxo-1,4,5,6-tetrahydro-pyrimidin-4-yl)-phenyl]-amide; compound with trifluoro-acetic acid

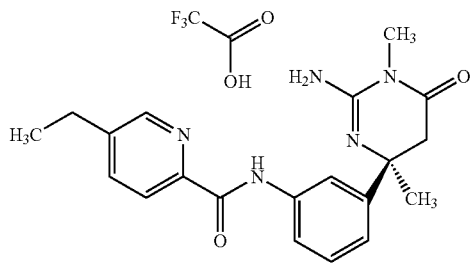 [SMILES: CCc1ccc(C(=O)Nc2cccc([C@]3(C)CC(=O)N(C)C(N)=N3)c2)nc1 ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 5-ethyl-pyridine-2-carboxylic acid followed by deprotection of the intermediate yielded the title compound as a white solid. MS (ESI): m/z=366.5 [M+H]$^+$.

Example 84

4-Methyl-1H-imidazole-2-carboxylic acid [3-((S)-2-amino-1,4-dimethyl-6-oxo-1,4,5,6-tetrahydro-pyrimidin-4-yl)-phenyl]-amide; compound with trifluoro-acetic acid

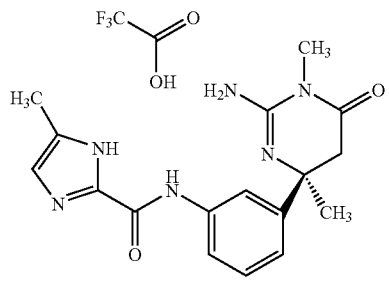 [SMILES: Cc1cnc(C(=O)Nc2cccc([C@]3(C)CC(=O)N(C)C(N)=N3)c2)[nH]1 ; O=C(O)C(F)(F)F]

The coupling of [(S)-4-(3-amino-phenyl)-1,4-dimethyl-6-oxo-1,4,5,6-tetrahydro-pyrimidin-2-yl]-carbamic acid tert-butyl ester and 5-methyl-1H-imidazole-2-carboxylic acid followed by deprotection of the intermediate yielded the title compound as a pale yellow semi solid. MS (ESI): m/z=341.1 [M+H]$^+$.

Example 85

5-Fluoro-pyridine-2-carboxylic acid [3-((S)-2-amino-4-ethyl-1-methyl-6-oxo-1,4,5,6-tetrahydro-pyrimidin-4-yl)-phenyl]-amide; compound with trifluoro-acetic acid

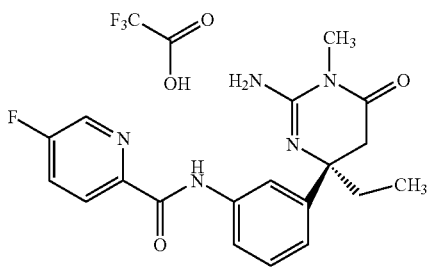 [SMILES: CC[C@@]1(c2cccc(NC(=O)c3ccc(F)cn3)c2)CC(=O)N(C)C(N)=N1 ; O=C(O)C(F)(F)F]

The coupling of [(S)-4-(3-amino-phenyl)-4-ethyl-1-methyl-6-oxo-1,4,5,6-tetrahydro-pyrimidin-2-yl]-carbamic acid tert-butyl ester and 5-fluoro-pyridine-2-carboxylic acid followed by deprotection of the intermediate yielded the title compound as a white solid. MS (ESI): m/z=370.1 [M+H]$^+$.

Example 86

5-Trifluoromethyl-pyridine-2-carboxylic acid [3-((S)-2-amino-4-ethyl-1-methyl-6-oxo-1,4,5,6-tetrahydro-pyrimidin-4-yl)-phenyl]amide; compound with trifluoro-acetic acid

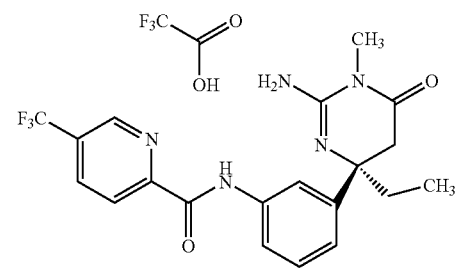 [SMILES: CC[C@@]1(c2cccc(NC(=O)c3ccc(C(F)(F)F)cn3)c2)CC(=O)N(C)C(N)=N1 ; O=C(O)C(F)(F)F]

The coupling of [(S)-4-(3-amino-phenyl)-4-ethyl-1-methyl-6-oxo-1,4,5,6-tetrahydro-pyrimidin-2-yl]-carbamic acid tert-butyl ester and 5-trifluoromethyl-pyridine-2-carboxylic acid followed by deprotection of the intermediate yielded the title compound as a white solid. MS (ESI): m/z=420.2 [M+H]$^+$.

Example 87

5-Chloro-pyridine-2-carboxylic acid [3-((S)-2-amino-1-methyl-6-oxo-4-propyl-1,4,5,6-tetrahydro-pyrimidin-4-yl)-phenyl]-amide; salt with trifluoro-acetic acid

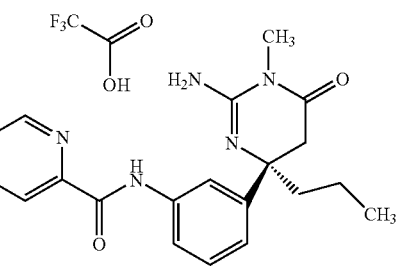

The coupling of [(S)-4-(3-amino-phenyl)-1-methyl-6-oxo-4-propyl-1,4,5,6-tetrahydro-pyrimidin-2-yl]-carbamic acid tert-butyl ester and 5-chloro-pyridine-2-carboxylic acid followed by deprotection of the intermediate yielded the title compound as a white solid. MS (ESI): m/z=400.1 [M+H]$^+$.

Example 88

Pyridine-2-carboxylic acid [3-((S)-2-amino-1-methyl-6-oxo-4-propyl-1,4,5,6-tetrahydro-pyrimidin-4-yl)-phenyl]-amide; compound with trifluoro-acetic acid

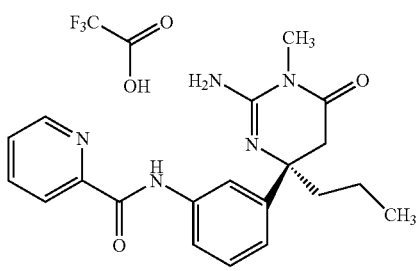 [SMILES: CCC[C@@]1(c2cccc(NC(=O)c3ccccn3)c2)CC(=O)N(C)C(N)=N1 ; O=C(O)C(F)(F)F]

The coupling of [(S)-4-(3-amino-phenyl)-1-methyl-6-oxo-4-propyl-1,4,5,6-tetrahydro-pyrimidin-2-yl]-carbamic acid tert-butyl ester and pyridine-2-carboxylic acid followed by deprotection of the intermediate yielded the title compound as a white solid. MS (ESI): m/z=366.3 [ M+H]⁺.

Example 89

1-Methyl-1H-pyrazole-3-carboxylic acid [3-((S)-2-amino-1-methyl-6-oxo-4-propyl-1,4,5,6-tetrahydro-pyrimidin-4-yl)-phenyl]-amide; compound with trifluoro-acetic acid

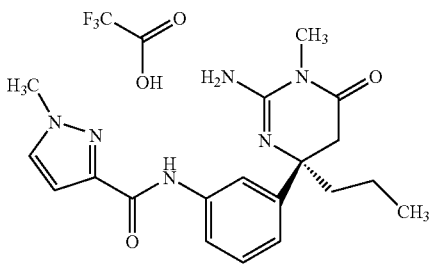 [SMILES: CCC[C@@]1(c2cccc(NC(=O)c3ccn(C)n3)c2)CC(=O)N(C)C(N)=N1 ; O=C(O)C(F)(F)F]

The coupling of [(S)-4-(3-amino-phenyl)-1-methyl-6-oxo-4-propyl-1,4,5,6-tetrahydro-pyrimidin-2-yl]-carbamic acid tert-butyl ester and 1-methyl-1H-pyrazole-3-carboxylic acid followed by deprotection of the intermediate yielded the title compound as a brownish oil. MS (ESI): m/z=369.3 [ M+H]⁺.

Example 90

2-Methyl-oxazole-4-carboxylic acid [3-((S)-2-amino-1-methyl-6-oxo-4-propyl-1,4,5,6-tetrahydro-pyrimidin-4-yl)-phenyl]-amide; salt with trifluoro-acetic acid

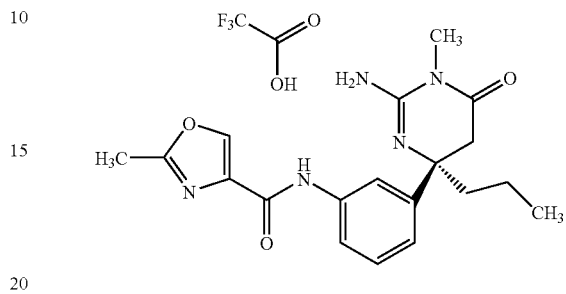

The coupling of [(S)-4-(3-amino-phenyl)-1-methyl-6-oxo-4-propyl-1,4,5,6-tetrahydro-pyrimidin-2-yl]-carbamic acid tert-butyl ester and 2-methyl-oxazole-4-carboxylic acid followed by deprotection of the intermediate yielded the title compound as a white solid. MS (ESI): m/z=370.3 [ M+H]⁺.

Example 91

5-Chloro-pyridine-2-carboxylic acid [3-((4S,5R)-2-amino-1,4,5-trimethyl-6-oxo-1,4,5,6-tetrahydro-pyrimidin-4-yl)-phenyl]amide; salt with trifluoro-acetic acid

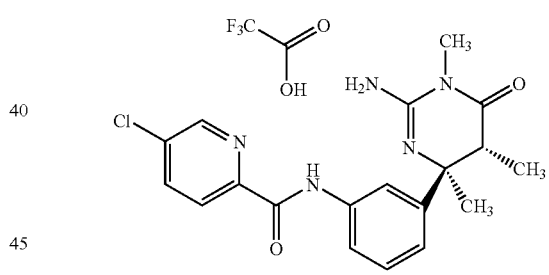

To a solution of [(S)-1,4-dimethyl-4-(3-nitro-phenyl)-6-oxo-1,4,5,6-tetrahydro-pyrimidin-2-yl]-carbamic acid tert-butyl ester (110 mg, intermediate E1) in THF (3.0 ml) was added at −78° C. a solution of LDA (3 eq., 1.95 ml) and stirring was continued for 1 h. The mixture was treated at −78° C. with a solution of iodomethane (38 µl) in THF (2.0 ml) and stirring was continued at the same temperature for 1.5 h. The mixture was quenched with saturated aqueous NH₄Cl, extracted with diethyl ether, the organic layer was dried and evaporated. The residue was chromatographed on silica using n-heptane/ethyl acetate (5:1) to give [(4S,5R)-1,4,5-trimethyl-4-(3-nitro-phenyl)-6-oxo-1,4,5,6-tetrahydro-pyrimidin-2-yl]-carbamic acid tert-butyl ester (72 mg) as a colorless foam. MS (ESI): m/z=377.4 [ M+H]⁺. The hydrogenation of the nitro group to give the aniline (intermediate F) was carried out as described in Scheme 1.

The coupling of [(4S,5R)-4-(3-amino-phenyl)-1,4,5-trimethyl-6-oxo-1,4,5,6-tetrahydro-pyrimidin-2-yl]-carbamic acid tert-butyl ester and 5-chloro-pyridine-2-carboxylic acid followed by deprotection of the intermediate yielded the title compound as a white solid. MS (ESI): m/z=386.4 [ M+H]⁺.

Example 92

5-Chloro-pyridine-2-carboxylic acid [3-((4S,5R)-2-amino-5-ethyl-1,4-dimethyl-6-oxo-1,4,5,6-tetrahydro-pyrimidin-4-yl)-phenyl]-amide; salt with trifluoro-acetic acid

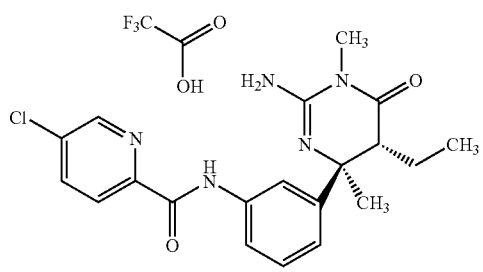 [SMILES: CC[C@H]1C(=O)N(C)C(N)=N[C@]1(C)c1cccc(NC(=O)c2ccc(Cl)cn2)c1 ; O=C(O)C(F)(F)F]

To a solution of [(S)-1,4-dimethyl-4-(3-nitro-phenyl)-6-oxo-1,4,5,6-tetrahydro-pyrimidin-2-yl]-carbamic acid tert-butyl ester (165 mg, intermediate E1) in THF (3.0 ml) was added at –78° C. a solution of LDA (3 eq., 2.8 ml) and stirring was continued for 1 h. The mixture was treated at –78° C. with a solution of iodoethane (67 µl) in THF (2.0 ml) and stirring was continued at the same temperature for 1.5 h and at –20° C. for 16 hours. The mixture was quenched with saturated aqueous NH₄Cl, extracted with diethyl ether, the organic layer was dried and evaporated. The residue was chromatographed on silica using n-heptane/ethyl acetate (4:1) to give [(4S,5R)-5-ethyl-1,4-dimethyl-4-(3-nitro-phenyl)-6-oxo-1,4,5,6-tetrahydro-pyrimidin-2-yl]-carbamic acid tert-butyl ester (96 mg) as a colorless foam. MS (ESI): m/z=391.3 [ M+H]⁺. The hydrogenation of the nitro group to give the aniline (intermediate F) was carried out as described in Scheme 1.

The coupling of [(4S,5R)-4-(3-amino-phenyl)-5-ethyl-1,4-dimethyl-6-oxo-1,4,5,6-tetrahydro-pyrimidin-2-yl]-carbamic acid tert-butyl ester and 5-chloro-pyridine-2-carboxylic acid followed by deprotection of the intermediate yielded the title compound as a white solid. MS (ESI): m/z=400.2 [ M+H]⁺.

Example 93

3-Methoxy-pyridine-2-carboxylic acid [3-((R)-2-amino-1,4,5,5-tetramethyl-6-oxo-1,4,5,6-tetrahydro-pyrimidin-4-yl)-phenyl]amide; salt with formic acid

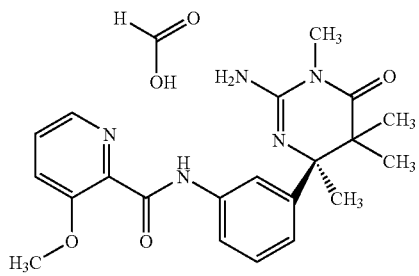 [SMILES: COc1cccnc1C(=O)Nc1cccc([C@@]2(C)N=C(N)N(C)C(=O)C2(C)C)c1 ; O=CO]

The coupling of [(R)-4-(3-amino-phenyl)-1,4,5,5-tetramethyl-6-oxo-1,4,5,6-tetrahydro-pyrimidin-2-yl]-carbamic acid tert-butyl ester and 3-methoxy-pyridine-2-carboxylic acid followed by deprotection of the intermediate yielded the title compound as a colourless amorphous solid. MS (ESI): m/z=396.3 [ M+H]⁺.

Example 94

5-Chloro-pyridine-2-carboxylic acid [3-((R)-2-amino-1,4,5,5-tetramethyl-6-oxo-1,4,5,6-tetrahydro-pyrimidin-4-yl)-phenyl]amide; salt with formic acid

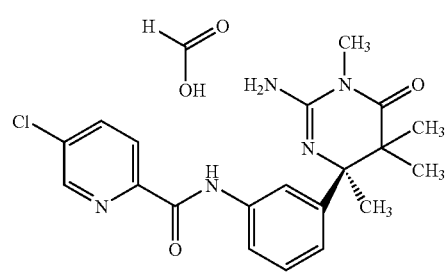 [SMILES: CN1C(=O)C(C)(C)[C@@](C)(c2cccc(NC(=O)c3ccc(Cl)cn3)c2)N=C1N ; O=CO]

The coupling of [(R)-4-(3-amino-phenyl)-1,4,5,5-tetramethyl-6-oxo-1,4,5,6-tetrahydro-pyrimidin-2-yl]-carbamic acid tert-butyl ester and 5-chloro-pyridine-2-carboxylic acid followed by deprotection of the intermediate yielded the title compound as a white solid. MS (ESI): m/z=400.2 [ M+H]⁺.

Example 95

5-Chloro-3-methyl-pyridine-2-carboxylic acid [3-((R)-2-amino-1,4,5,5-tetramethyl-6-oxo-1,4,5,6-tetrahydro-pyrimidin-4-yl)-phenyl]amide; salt with formic acid

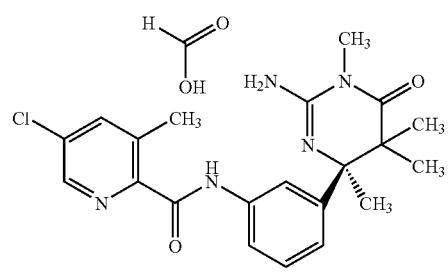

The coupling of [(R)-4-(3-amino-phenyl)-1,4,5,5-tetramethyl-6-oxo-1,4,5,6-tetrahydro-pyrimidin-2-yl]-carbamic acid tert-butyl ester,

[(S)-4-(5-amino-2-fluoro-phenyl)-1,4,5,5-tetramethyl-6-oxo-1,4,5,6-tetrahydro-pyrimidin-2-yl]-carbamic acid tert-butyl ester from experiment F7, and 5-chloro-3-methyl-pyridine-2-carboxylic acid followed by deprotection of the intermediate yielded the title compound as a white solid. MS (ESI): m/z=414.3 [ M+H]⁺.

Example 96

Thieno[2,3-c]pyridine-7-carboxylic acid [3-((R)-2-amino-1,4,5,5-tetramethyl-6-oxo-1,4,5,6-tetrahydro-pyrimidin-4-yl)-phenyl]amide; salt with formic acid

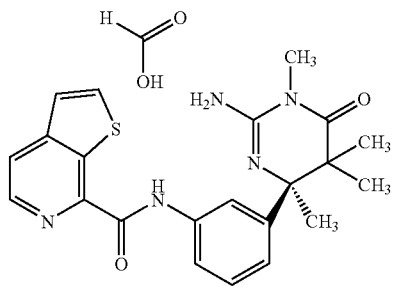

The coupling of [(R)-4-(3-amino-phenyl)-1,4,5,5-tetramethyl-6-oxo-1,4,5,6-tetrahydro-pyrimidin-2-yl]-carbamic acid tert-butyl ester and thieno[2,3-c]pyridine-7-carboxylic acid (prepared according to the lit. given in example 60 followed by deprotection of the intermediate yielded the title compound as a pale yellow solid. MS (ESI): m/z=422.2 [M+H]$^+$.

Example 97

3-(2-Chloro-phenyl)-pyridine-2-carboxylic acid [3-((R)-2-amino-1,4,5,5-tetramethyl-6-oxo-1,4,5,6-tetrahydro-pyrimidin-4-yl)-phenyl]amide; salt with trifluoro-acetic acid

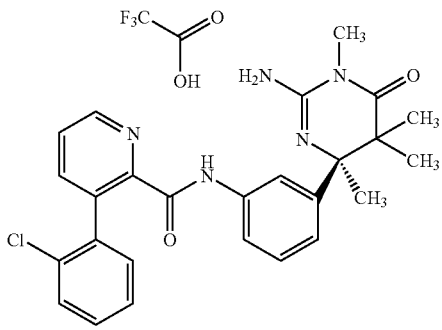 [SMILES: CN1C(=O)C(C)(C)[C@@](C)(c2cccc(NC(=O)c3ncccc3-c3ccccc3Cl)c2)N=C1N ; O=C(O)C(F)(F)F]

The coupling of [(R)-4-(3-amino-phenyl)-1,4,5,5-tetramethyl-6-oxo-1,4,5,6-tetrahydro-pyrimidin-2-yl]-carbamic acid tert-butyl ester and 3-(2-chloro-phenyl)-pyridine-2-carboxylic acid followed by deprotection of the intermediate yielded the title compound as an off-white solid. MS (ESI): m/z=476.2 [M+H]$^+$.

Example 98

1-Methyl-1H-pyrazole-3-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

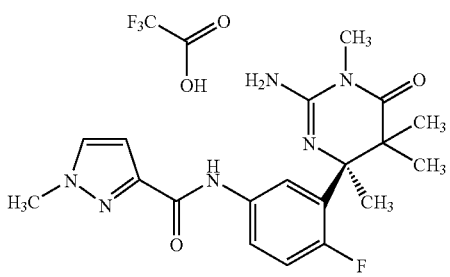

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 1-methyl-1H-pyrazole-3-carboxylic acid followed by deprotection of the intermediate yielded the title compound as a white solid. MS (ESI): m/z=387.3 [M+H]$^+$.

Example 99

5-Chloro-3-methyl-pyridine-2-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

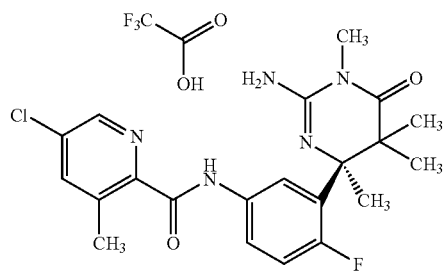 [SMILES: Cc1cc(Cl)cnc1C(=O)Nc1ccc(F)c([C@@]2(C)N=C(N)N(C)C(=O)C2(C)C)c1 ; O=C(O)C(F)(F)F]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 5-chloro-3-methyl-pyridine-2-carboxylic acid followed by deprotection of the intermediate yielded the title compound as a white solid. MS (ESI): m/z=432.4 [M+H]$^+$.

Example 100

Pyridine-2-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

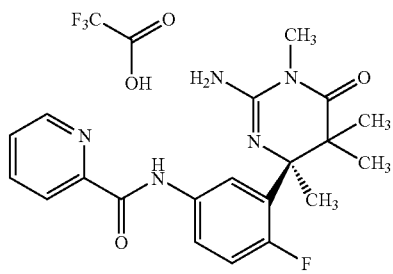 [SMILES: CN1C(=O)C(C)(C)[C@@](C)(c2cc(NC(=O)c3ccccn3)ccc2F)N=C1N ; O=C(O)C(F)(F)F]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and pyridine-2-carboxylic acid followed by deprotection of the intermediate yielded the title compound as a white solid. MS (ESI): m/z=384.3 [ M+H]$^+$.

Example 101

2-Methyl-oxazole-4-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

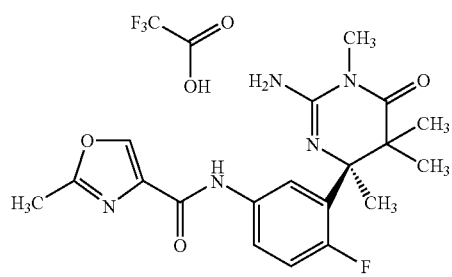

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 2-methyl-oxazole-4-carboxylic acid followed by deprotection of the intermediate yielded the title compound as a white solid. MS (ESI): m/z=388.3 [ M+H]$^+$.

Example 102

5-Methyl-thiophene-2-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

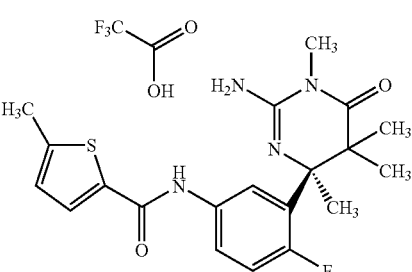

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 5-methyl-thiophene-2-carboxylic acid followed by deprotection of the intermediate yielded the title compound as a white solid. MS (ESI): m/z=403.4 [ M+H]$^+$.

Example 103

5-Difluoromethoxy-pyridine-2-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

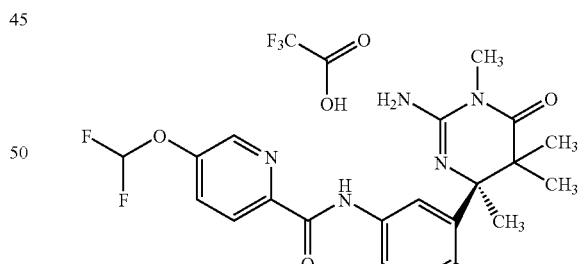

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 5-difluoromethoxy-pyridine-2-carboxylic acid followed by deprotection of the intermediate yielded the title compound as a white solid. MS (ESI): m/z=450.2 [ M+H]$^+$.

Example 104

3-Methoxy-pyridine-2-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

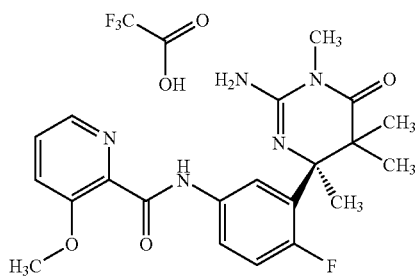 [SMILES: COc1cccnc1C(=O)Nc1ccc(F)c([C@@]2(C)N=C(N)N(C)C(=O)C2(C)C)c1 ; O=C(O)C(F)(F)F]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 3-methoxy-pyridine-2-carboxylic acid followed by deprotection of the intermediate yielded the title compound as a pale yellow solid. MS (ESI): m/z=414.3 [M+H]$^+$.

Example 105

3-Methyl-pyridine-2-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

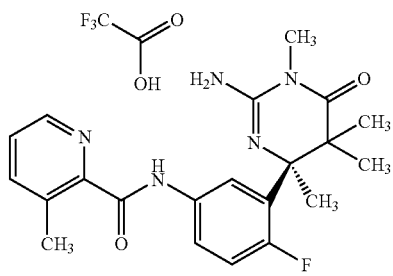 [SMILES: Cc1cccnc1C(=O)Nc1ccc(F)c([C@@]2(C)N=C(N)N(C)C(=O)C2(C)C)c1 ; O=C(O)C(F)(F)F]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 3-methyl-pyridine-2-carboxylic acid followed by deprotection of the intermediate yielded the title compound as a white solid. MS (ESI): m/z=398.3 [M+H]$^+$.

Example 106

5-Chloro-pyrimidine-2-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

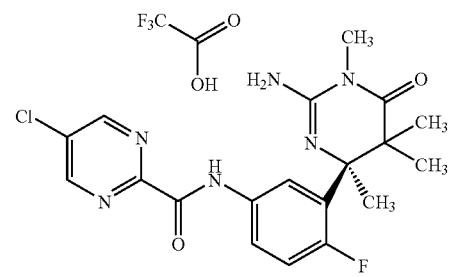 [SMILES: CN1C(=O)C(C)(C)[C@@](C)(c2cc(NC(=O)c3ncc(Cl)cn3)ccc2F)N=C1N ; O=C(O)C(F)(F)F]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 5-chloro-pyrimidine-2-carboxylic acid followed by deprotection of the intermediate yielded the title compound as a white solid. MS (ESI): m/z=419.3 [M+H]$^+$.

Example 107

5-Chloro-pyrazine-2-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

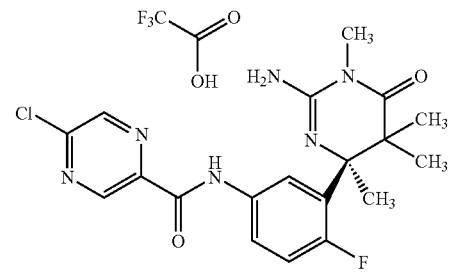 [SMILES: CN1C(=O)C(C)(C)[C@@](C)(c2cc(NC(=O)c3cnc(Cl)cn3)ccc2F)N=C1N ; O=C(O)C(F)(F)F]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 5-chloro-pyrazine-2-carboxylic acid followed by deprotection of the intermediate yielded the title compound as a pale yellow solid. MS (ESI): m/z=419.3 [M+H]$^+$.

Example 108

3-Fluoro-pyridine-2-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

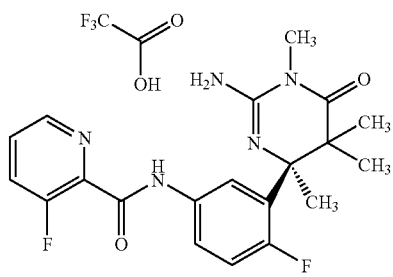 [SMILES: CN1C(=O)C(C)(C)[C@@](C)(c2cc(NC(=O)c3ncccc3F)ccc2F)N=C1N ; O=C(O)C(F)(F)F]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 3-fluoro-pyridine-2-carboxylic acid followed by deprotection of the intermediate yielded the title compound as a white solid. MS (ESI): m/z=402.4 [M+H]$^+$.

Example 109

5-Phenyl-oxazole-4-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

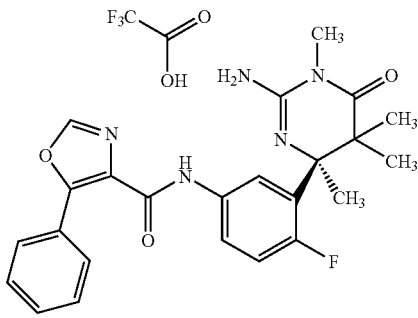 [SMILES: CN1C(=O)C(C)(C)[C@@](C)(c2cc(NC(=O)c3ncoc3-c3ccccc3)ccc2F)N=C1N ; O=C(O)C(F)(F)F]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 5-phenyl-oxazole-4-carboxylic acid followed by deprotection of the intermediate yielded the title compound as a white solid. MS (ESI): m/z=450.2 [M+H]$^+$.

Example 110

5-Trifluoromethyl-pyridine-2-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

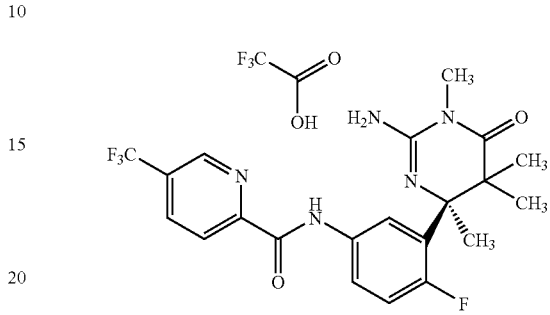

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 5-trifluoromethyl-pyridine-2-carboxylic acid followed by deprotection of the intermediate yielded the title compound as a white solid. MS (ESI): m/z=452.2 [M+H]$^+$.

Example 111

1-Methyl-1H-imidazole-2-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

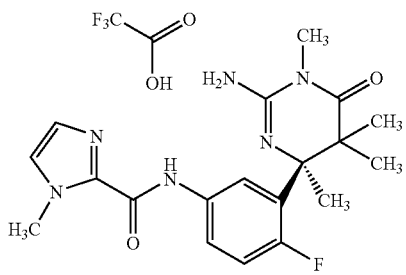 [SMILES: CN1C(=O)C(C)(C)[C@@](C)(c2cc(NC(=O)c3nccn3C)ccc2F)N=C1N ; O=C(O)C(F)(F)F]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 5-trifluoromethyl-pyridine-2-carboxylic acid followed by deprotection of the intermediate yielded the title compound as a white solid. MS (ESI): m/z=387.3 [M+H]$^+$.

Example 112

1-Methyl-1H-imidazole-4-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

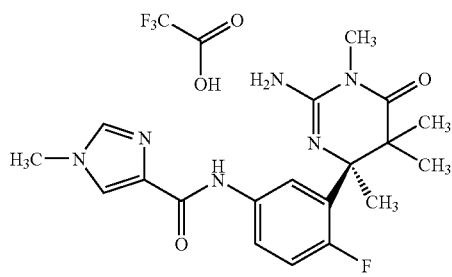

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 1-methyl-1H-imidazole-4-carboxylic acid followed by deprotection of the intermediate yielded the title compound as a white solid. MS (ESI): m/z=387.3 [M+H]$^+$.

Example 113

5-Methoxy-pyridine-2-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

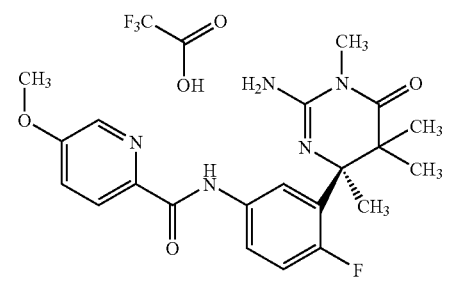 [SMILES: COc1ccc(C(=O)Nc2ccc(F)c([C@@]3(C)N=C(N)N(C)C(=O)C3(C)C)c2)nc1 ; O=C(O)C(F)(F)F]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 5-methoxy-pyridine-2-carboxylic acid followed by deprotection of the intermediate yielded the title compound as a white solid. MS (ESI): m/z=414.4 [M+H]$^+$.

Example 114

5-Fluoro-pyridine-2-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

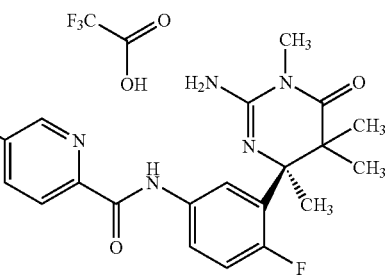

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 5-fluoro-pyridine-2-carboxylic acid followed by deprotection of the intermediate yielded the title compound as a white solid. MS (ESI): m/z=402.4 [M+H]$^+$.

Example 115

5-Cyano-pyridine-2-carboxylic acid [3-((S)-2-amino-1,4,5,5-tetramethyl-6-oxo-1,4,5,6-tetrahydro-pyrimidin-4-yl)-4-fluoro-phenyl]amide; salt with formic acid

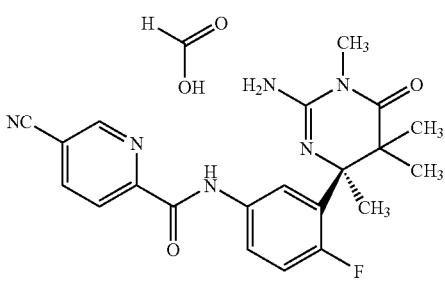

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 5-cyano-pyridine-2-carboxylic acid followed by deprotection of the intermediate yielded the title compound as a white solid. MS (ESI): m/z=409.3 [M+H]$^+$.

Example 116

5-Methyl-isoxazole-3-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

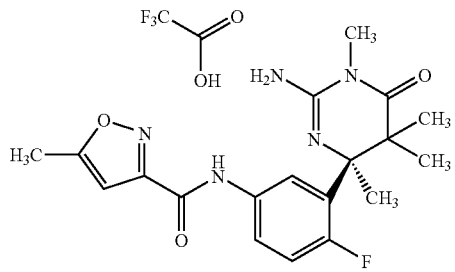

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 5-methyl-isoxazole-3-carboxylic acid followed by deprotection of the intermediate yielded the title compound as a white solid. MS (ESI): m/z=388.3 [M+H]$^+$.

Example 117

Oxazole-2-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

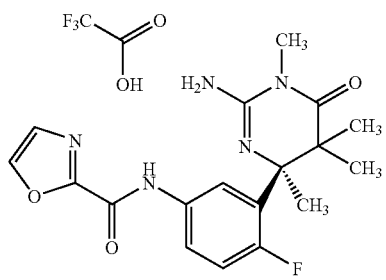 [SMILES: CN1C(=O)C(C)(C)[C@@](C)(c2cc(NC(=O)c3ncco3)ccc2F)N=C1N ; O=C(O)C(F)(F)F]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and oxazole-2-carboxylic acid followed by deprotection of the intermediate yielded the title compound as a white solid. MS (ESI): m/z=374.2 [M+H]$^+$.

Example 118

3-Chloro-5-trifluoromethyl-pyridine-2-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

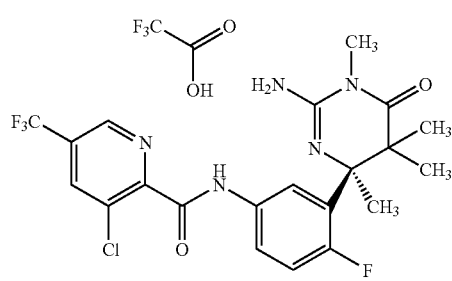 [SMILES: CN1C(=O)C(C)(C)[C@@](C)(c2cc(NC(=O)c3ncc(C(F)(F)F)cc3Cl)ccc2F)N=C1N ; O=C(O)C(F)(F)F]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 3-chloro-5-trifluoromethyl-pyridine-2-carboxylic acid followed by deprotection of the intermediate yielded the title compound as a white solid. MS (ESI): m/z=486.2 [M+H]$^+$.

Example 119

6-Chloro-3-trifluoromethyl-pyridine-2-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

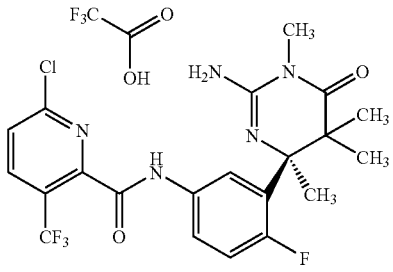 [SMILES: CN1C(=O)C(C)(C)[C@@](C)(c2cc(NC(=O)c3nc(Cl)ccc3C(F)(F)F)ccc2F)N=C1N ; O=C(O)C(F)(F)F]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 6-chloro-3-trifluoromethyl-pyridine-2-carboxylic acid followed by deprotection of the intermediate yielded the title compound as a white solid. MS (ESI): m/z=486.2 [M+H]$^+$.

Example 120

6-Chloro-imidazo[1,2-a]pyridine-2-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

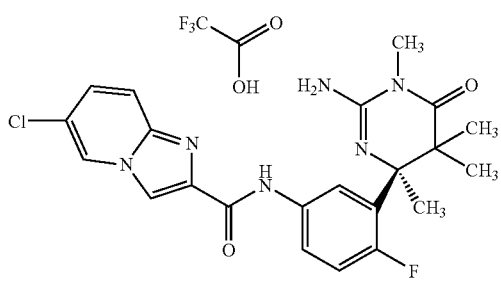 [SMILES: CN1C(=O)C(C)(C)[C@@](C)(c2cc(NC(=O)c3cn4cc(Cl)ccc4n3)ccc2F)N=C1N ; O=C(O)C(F)(F)F]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 6-chloro-imidazo[1,2-a]pyridine-2-carboxylic acid followed by deprotection of the intermediate yielded the title compound as a white solid. MS (ESI): m/z=457.3 [M+H]$^+$.

Example 121

1-Difluoromethyl-1H-pyrazole-3-carboxylic acid [3-((S)-2-amino-1,4,5,5-tetramethyl-6-oxo-1,4,5,6-tetrahydro-pyrimidin-4-yl)-4-fluoro-phenyl]amide; salt with trifluoro-acetic acid

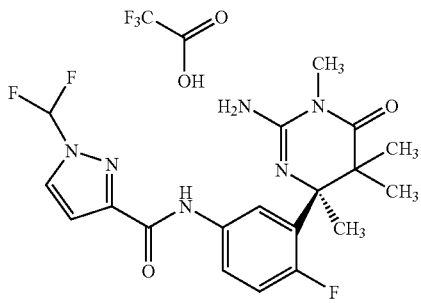 [SMILES: CN1C(=O)C(C)(C)[C@@](C)(c2cc(NC(=O)c3ccn(C(F)F)n3)ccc2F)N=C1N ; O=C(O)C(F)(F)F]

The coupling of [(S)-4-(5-amino-2-fluoro-phenyl)-1,4,5,5-tetramethyl-6-oxo-1,4,5,6-tetrahydro-pyrimidin-2-yl]-carbamic acid tert-butyl ester and 1-difluoromethyl-1H-pyrazole-3-carboxylic acid followed by deprotection of the intermediate yielded the title compound as a white solid. MS (ESI): m/z=423.2 [M+H]$^+$.

Example 122

5-Chloro-pyridine-2-carboxylic acid [3-((R)-2-amino-5-benzyloxy-1,4-dimethyl-6-oxo-1,4,5,6-tetrahydro-pyrimidin-4-yl)-4-fluoro-phenyl]amide; salt with trifluoro-acetic acid

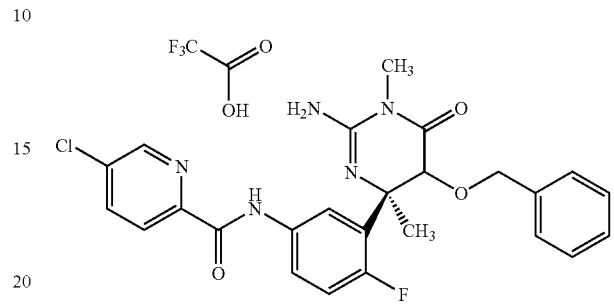

The coupling of [(R)-4-(5-amino-2-fluoro-phenyl)-5-benzyloxy-1,4-dimethyl-6-oxo-1,4,5,6-tetrahydro-pyrimidin-2-yl]-carbamic acid tert-butyl ester and 5-chloro-pyridine-2-carboxylic acid followed by deprotection of the intermediate yielded the title compound as a white solid. MS (ESI): m/z=496.3 [M+H]$^+$.

Example 123

Pyridine-2-carboxylic acid [3-((R)-2-amino-5-hydroxy-1,4-dimethyl-6-oxo-1,4,5,6-tetrahydro-pyrimidin-4-yl)-4-fluoro-phenyl]amide; salt with formic acid

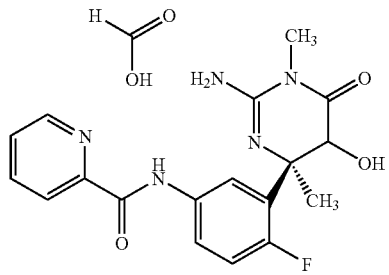 [SMILES: CN1C(=O)C(O)[C@@](C)(c2cc(NC(=O)c3ccccn3)ccc2F)N=C1N ; O=CO]

A solution of 5-chloro-pyridine-2-carboxylic acid [3-((R)-2-amino-5-benzyloxy-1,4-dimethyl-6-oxo-1,4,5,6-tetrahydro-pyrimidin-4-yl)-4-fluoro-phenyl]-amide; salt with trifluoro-acetic acid (30 mg, from example 69) was desalted by partitioning between sat. aqueous Na2CO3 and ethyl acetate. The free amine was dissolved in ethanol (2.0 ml) and NEt3 (5 ul) and hydrogenated over Pd/C (10%, 31 mg) at 22° C. and atmospheric pressure overnight. The mixture was filtered, the filtrate evaporated and the residue purified over a HPLC RP-18 column using a gradient of CH3CN/water to give the title compound as a colorless oil. MS (ESI): m/z=372.2 [M+H]$^+$.

Example 124

5-Chloro-pyridine-2-carboxylic acid [3-((S)-2-amino-1-cyclopropylmethyl-4-methyl-6-oxo-1,4,5,6-tetrahydro-pyrimidin-4-yl)-phenyl]amide; salt with trifluoro-acetic acid

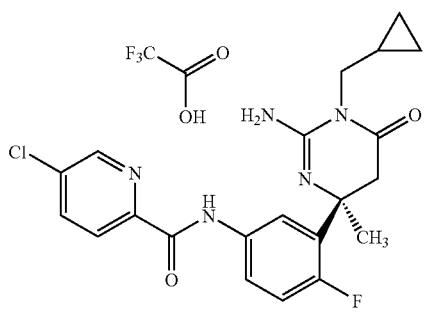 [SMILES: C[C@@]1(c2cc(NC(=O)c3ccc(Cl)cn3)ccc2F)CC(=O)N(CC2CC2)C(N)=N1 ; O=C(O)C(F)(F)F]

The coupling of (S)-2-amino-6-(3-amino-phenyl)-3-cyclopropylmethyl-6-methyl-5,6-dihydro-3H-pyrimidin-4-one and 5-chloro-pyridine-2-carboxylic acid followed by deprotection of the intermediate yielded the title compound as a white solid. MS (ESI): m/z=412.2 [ M+H]$^+$.

Example 125

5-Chloro-pyridine-2-carboxylic acid [5-((S)-2-amino-1,4-dimethyl-6-oxo-1,4,5,6-tetrahydro-pyrimidin-4-yl)-2-fluoro-phenyl]amide; salt with trifluoro-acetic acid

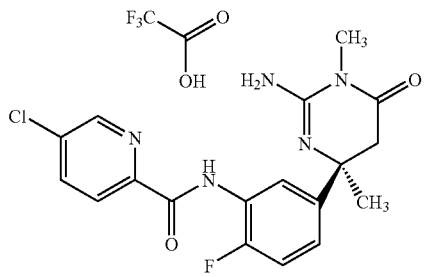 [SMILES: CN1C(=O)C[C@@](C)(c2ccc(F)c(NC(=O)c3ccc(Cl)cn3)c2)N=C1N ; O=C(O)C(F)(F)F]

The coupling of [(S)-4-(3-amino-4-fluoro-phenyl)-1,4-dimethyl-6-oxo-1,4,5,6-tetrahydro-pyrimidin-2-yl]-carbamic acid tert-butyl ester and 5-chloro-pyridine-2-carboxylic acid followed by deprotection of the intermediate yielded the title compound as a white solid. MS (ESI): m/z=390.1 [ M+H]$^+$.

Example 126

5-Chloro-pyridine-2-carboxylic acid [3-((S)-2-amino-1,4,5,5-tetramethyl-6-oxo-1,4,5,6-tetrahydro-pyrimidin-4-yl)-4-chloro-phenyl]amide; salt with trifluoro-acetic acid

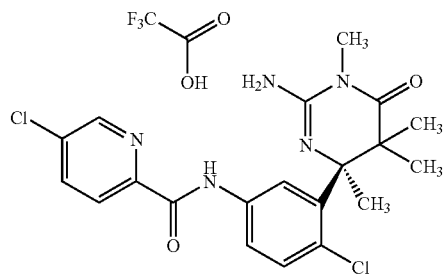 [SMILES: CN1C(=O)C(C)(C)[C@@](C)(c2cc(NC(=O)c3ccc(Cl)cn3)ccc2Cl)N=C1N ; O=C(O)C(F)(F)F]

The coupling of [(S)-4-(5-Amino-2-chloro-phenyl)-1,4,5,5-tetramethyl-6-oxo-1,4,5,6-tetrahydro-pyrimidin-2-yl]-carbamic acid tert-butyl ester and 5-chloro-pyridine-2-carboxylic acid followed by deprotection of the intermediate yielded the title compound as a white solid. MS (ESI): m/z=434.2 [ M+H]$^+$.

Example 127

N-[(1S)-2'-amino-1'-methyl-6'-oxo-2,3,5',6'-tetrahydro-1'H-spiro[indene-1,4'-pyrimidin]-6-yl]-5-chloro-pyridine-2-carboxamide; salt with trifluoro-acetic acid

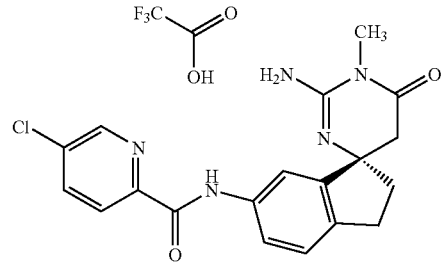 [SMILES: CN1C(=O)C[C@]2(CCc3ccc(NC(=O)c4ccc(Cl)cn4)cc32)N=C1N ; O=C(O)C(F)(F)F]

The coupling of tert-butyl [(1S)-6-amino-1'-methyl-6'-oxo-2,3,5',6'-tetrahydro-1'H-spiro[indene-1,4'-pyrimidin]-2'-yl]carbamate and 5-chloro-pyridine-2-carboxylic acid followed by deprotection of the intermediate yielded the title compound as a white solid. MS (ESI): m/z=384.2 [ M+H]$^+$.

Example 128

N-[(1S)-2'-amino-1'-methyl-6'-oxo-2,3,5',6'-tetrahydro-1'H-spiro[indene-1,4'-pyrimidin]-6-yl]pyridine-2-carboxamide; salt with trifluoro-acetic acid

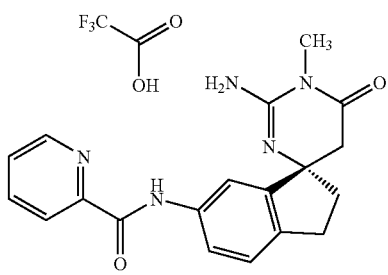 [SMILES: CN1C(=O)C[C@]2(CCc3ccc(NC(=O)c4ccccn4)cc32)N=C1N ; O=C(O)C(F)(F)F]

The coupling of tert-butyl [(1S)-6-amino-1'-methyl-6'-oxo-2,3,5',6'-tetrahydro-1'H-spiro[indene-1,4'-pyrimidin]-2'-yl]carbamate and pyridine-2-carboxylic acid followed by deprotection of the intermediate yielded the title compound as a brownish solid. MS (ESI): m/z=350.4 [ M+H]$^+$.

Example 129

N-[(1S)-2'-amino-1'-methyl-6'-oxo-2,3,5',6'-tetrahydro-1'H-spiro[indene-1,4'-pyrimidin]-6-yl]-5-(2,2,2-trifluoro-ethoxy)-pyridine-2-carboxamide; salt with trifluoro-acetic acid

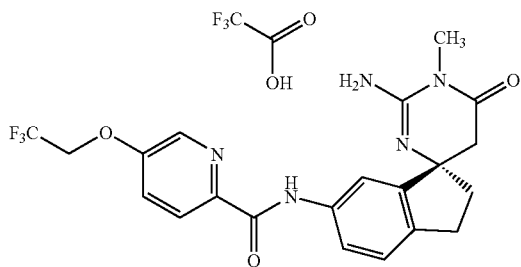 [SMILES: CN1C(=O)C[C@]2(CCc3ccc(NC(=O)c4ccc(OCC(F)(F)F)cn4)cc32)N=C1N ; O=C(O)C(F)(F)F]

The coupling of tert-butyl [(1S)-6-amino-1'-methyl-6'-oxo-2,3,5',6'-tetrahydro-1'H-spiro[indene-1,4'-pyrimidin]-2'-yl]carbamate and 5-(2,2,2-trifluoro-ethoxy)-pyridine-2-carboxylic acid (preparation described in example 63) followed by deprotection of the intermediate yielded the title compound as a white solid. MS (ESI): m/z=448.2 [ M+H]$^+$.

Example 130

N-[(1S)-2'-amino-1'-methyl-6'-oxo-2,3,5',6'-tetrahydro-1'H-spiro[indene-1,4'-pyrimidin]-6-yl]-3-trifluoromethyl-pyridine-2-carboxamide; salt with trifluoro-acetic acid

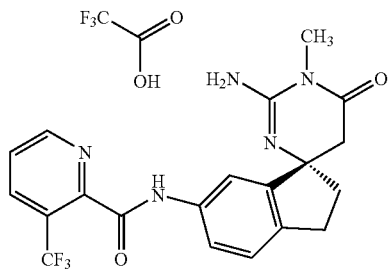 [SMILES: CN1C(=O)C[C@]2(CCc3ccc(NC(=O)c4ncccc4C(F)(F)F)cc32)N=C1N ; O=C(O)C(F)(F)F]

The coupling of tert-butyl [(1S)-6-amino-1'-methyl-6'-oxo-2,3,5',6'-tetrahydro-1'H-spiro[indene-1,4'-pyrimidin]-2'-yl]carbamate and 3-trifluoromethyl-pyridine-2-carboxylic acid followed by deprotection of the intermediate yielded the title compound as an off-white solid. MS (ESI): m/z=418.3 [ M+H]$^+$.

Example 131

The following test was carried out in order to determine the activity of the compounds of formula I:
Fluorescent-Peptide Cleavage Assay for BACE2 Inhibition BACE2 enzyme ectodomain (derived from plasmid "pET17b-T7-hu proBACE2") was prepared as described in Ostermann et al., "Crystal Structure of Human BACE2 in Complex with a Hydroxyethylamine Transition-state Inhibitor", Journal of Molecular Biology 2006, 355, 249-261. The pro-enzyme was stored at 4° C. at a concentration of 70 μg/ml.

A fluorescent peptide with the amino acid sequence WS EVNLD AEFRC-MR121 was synthesised and a stock solution of 1.5 mM in DMSO prepared and stored at −20° C. MR121 is a fluorophore with an excitation wavelength of 630 nm and emission wavelength of 695 nm. The MR121 fluorescence is quenched by the N-terminal tryptophan until the peptide is cleaved by BACE2.

Assays were all made in a Corning 384-well black polystyrene non-binding surface microtitre plate with clear flat bottom and using a Plate:Vision (Perkin Elmer) fluorescence reader. To perform the assay an 80 nM solution of BACE2 was prepared in assay buffer (assay buffer is 100 mM Na-acetate; 20 mM EDTA; 0.05% BSA; pH 4.5) and incubated at room temperature for 1 hour to activate the enzyme. 39 μl of the activated BACE2 was placed in each assay well, followed by 1 μl compound to be tested at an appropriate concentration in 100% DMSO. The plate was then mixed and incubated for 10 minutes at room temperature. To start the assay, 10 μl of a 1.5 μM solution fluorescent peptide in assay buffer was added and the fluorescence intensity in the assay mixture measured at 695 nm with an excitation wavelength of 630 nm for 30 minutes.

The assay readout is the rate of change of fluorescence intensity giving a relative measure of BACE2 activity. Small values correspond to high inhibition and larger values to low inhibition. To determine IC$_{50}$ values (i.e. the concentration inhibiting the enzyme activity by 50%) of the compound for BACE2, typically, 15 assays were made with a range of concentrations chosen empirically to give low, high and intermediate inhibition of the protease. $IC_{50}$ values were determined using these assay values generated for a range of inhibitor concentrations and the curve fitting software XLfit (IDBS) using the Sigmoidal Dose-Response Model.

The preferred compounds according to formula I have an inhibitory activity in the above assay ($IC_{50}$) preferably of 5 nM to 10 µM, more preferably of 5 nM to 0.5 µM and most preferably of 5 nM to 100 nM.

For example, the following compounds showed the following $IC_{50}$ values in the assay described above:

| Example | $IC_{50}$ (BACE2) [nM] |
|---|---|
| 1 | 13 |
| 2 | 14 |
| 3 | 86 |
| 4 | 98 |
| 5 | 121 |
| 6 | 307 |
| 7 | 1011 |
| 8 | 126 |
| 9 | 110 |
| 10 | 7 |
| 11 | 28 |
| 12 | 37 |
| 13 | 9 |
| 14 | 25 |
| 15 | 10 |
| 16 | 458 |
| 17 | 120 |
| 18 | 50 |
| 19 | 549 |
| 20 | 6 |
| 21 | 4200 |
| 22 | 123 |
| 23 | 58 |
| 24 | 217 |
| 25 | 10 |
| 26 | 960 |
| 27 | 18 |
| 28 | 18 |
| 29 | 48 |
| 30 | 150 |
| 31 | 30 |
| 32 | 220 |
| 33 | 1100 |
| 34 | 200 |
| 35 | 6420 |
| 36 | 42 |
| 37 | 21 |
| 38 | 9 |
| 39 | 11 |
| 40 | 39 |
| 41 | 95 |
| 42 | 125 |
| 43 | 87 |
| 44 | 7 |
| 45 | 7 |
| 46 | 14 |
| 47 | 8 |
| 48 | 9 |
| 49 | 15 |
| 50 | 10 |
| 51 | 33 |
| 52 | 11 |
| 53 | 8 |
| 54 | 976 |
| 55 | 349 |
| 56 | 2980 |
| 57 | 110 |
| 58 | 410 |
| 59 | 1700 |
| 60 | 240 |
| 61 | 240 |
| 62 | 150 |
| 63 | 60 |
| 64 | 60 |
| 65 | 160 |
| 66 | 1550 |
| 67 | 160 |
| 68 | 102 |
| 69 | 61 |
| 70 | 16 |
| 71 | 1310 |
| 72 | 1515 |
| 73 | 2070 |
| 74 | 79 |
| 75 | 17 |
| 76 | 300 |
| 77 | 1580 |
| 78 | 800 |
| 79 | 190 |
| 80 | 2100 |
| 81 | 170 |
| 82 | 590 |
| 83 | 40 |
| 84 | 390 |
| 85 | 300 |
| 86 | 250 |
| 87 | 170 |
| 88 | 1785 |
| 89 | 4755 |
| 90 | 1110 |
| 91 | 17 |
| 92 | 24 |
| 93 | 158 |
| 94 | 20 |
| 95 | 19 |
| 96 | 370 |
| 97 | 180 |
| 98 | 35 |
| 99 | 13 |
| 100 | 43 |
| 101 | 21 |
| 102 | 52 |
| 103 | 25 |
| 104 | 150 |
| 105 | 49 |
| 106 | 28 |
| 107 | 27 |
| 108 | 28 |
| 109 | 170 |
| 110 | 20 |
| 111 | 190 |
| 112 | 1260 |
| 113 | 21 |
| 114 | 43 |
| 115 | 63 |
| 116 | 840 |
| 117 | 230 |
| 118 | 19 |
| 119 | 560 |
| 120 | 43 |
| 121 | 17 |
| 122 | 10 |
| 123 | 350 |
| 124 | 42 |
| 125 | 310 |
| 126 | 36 |
| 127 | 160 |
| 128 | 1670 |
| 129 | 220 |
| 130 | 1340 |

Example A

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxyde (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula I | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula I | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesiumstearate and the flavouring additives and filled into sachets.

The invention claimed is:
1. A compound of the formula

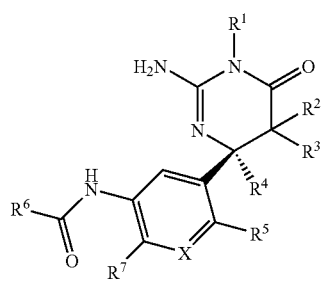

I wherein
X is CH or N;
$R^1$ is selected from the group consisting of hydrogen, $C_{1-7}$-alkyl, and benzyl;
$R^2$ is hydrogen or $C_{1-7}$-alkyl;
$R^3$ is hydrogen or $C_{1-7}$-alkyl;
or $R^2$ and $R^3$, together with the C atom to which they are attached, form a $C_{3-7}$-cycloalkyl ring;
$R^4$ is $C_{1-7}$-alkyl or $C_{3-7}$-cycloalkyl;

R⁵ is selected from the group consisting of hydrogen, $C_{1-7}$-alkyl, halogen, cyano and $C_{1-7}$-alkoxy;

R⁶ is aryl or heteroaryl, said aryl or heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo, and phenyl; and R⁷ is hydrogen;

or a pharmaceutically acceptable salt thereof.

2. A compound according to claim 1, wherein X is CH.

3. A compound according to claim 1, wherein X is N.

4. A compound according to claim 1, wherein R¹ is $C_{1-7}$-alkyl.

5. A compound according to claim 1, wherein R¹ is methyl.

6. A compound according to claim 1, wherein R² and R³ are hydrogen.

7. A compound according to any one of claim 1, wherein R² and R³ are methyl.

8. A compound according to claim 1, wherein R⁴ is methyl or ethyl.

9. A compound according to claim 1, wherein R⁵ is hydrogen or halogen.

10. A compound according to claim 1, wherein R⁵ is fluoro.

11. A compound according to claim 1, wherein R⁶ is heteroaryl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo, and phenyl.

12. A compound according to claim 1, wherein R⁶ is heteroaryl selected from the group consisting of thienyl, oxazolyl, pyridyl, pyrimidinyl and pyrazinyl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo, and phenyl.

13. A compound according to claim 1, wherein R⁶ is phenyl, said phenyl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

14. A compound according to claim 1, selected from the group consisting of:
(5-methyl-thiophene-2-carboxylic acid [3-((S)-2-amino-1,4-dimethyl-6-oxo-1,4,5,6-tetrahydro-pyrimidin-4-yl)-phenyl]-amide,
5-chloro-thiophene-2-carboxylic acid [3-((S)-2-amino-1,4-dimethyl-6-oxo-1,4,5,6-tetrahydro-pyrimidin-4-yl)-phenyl]-amide,
2,5-dimethyl-thiophene-3-carboxylic acid [3-((S)-2-amino-1,4-dimethyl-6-oxo-1,4,5,6-tetrahydro-pyrimidin-4-yl)-phenyl]-amide,
2,5-dimethyl-oxazole-4-carboxylic acid [3-((S)-2-amino-1,4-dimethyl-6-oxo-1,4,5,6-tetrahydro-pyrimidin-4-yl)-phenyl]-amide,
2,4-dimethyl-oxazole-5-carboxylic acid [3-((S)-2-amino-1,4-dimethyl-6-oxo-1,4,5,6-tetrahydro-pyrimidin-4-yl)-phenyl]-amide,
3-methyl-isoxazole-5-carboxylic acid [3-((S)-2-amino-1,4-dimethyl-6-oxo-1,4,5,6-tetrahydro-pyrimidin-4-yl)-phenyl]-amide,
1,5-dimethyl-1H-pyrazole-3-carboxylic acid [3-((S)-2-amino-1,4-dimethyl-6-oxo-1,4,5,6-tetrahydro-pyrimidin-4-yl)-phenyl]-amide,
2,5-dimethyl-2H-pyrazole-3-carboxylic acid [3-((S)-2-amino-1,4-dimethyl-6-oxo-1,4,5,6-tetrahydro-pyrimidin-4-yl)-phenyl]-amide,
imidazo[1,2-a]pyridine-2-carboxylic acid [3-((S)-2-amino-1,4-dimethyl-6-oxo-1,4,5,6-tetrahydro-pyrimidin-4-yl)-phenyl]-amide,
5-chloro-pyridine-2-carboxylic acid [3-((S)-2-amino-1,4-dimethyl-6-oxo-1,4,5,6-tetrahydro-pyrimidin-4-yl)-phenyl]-amide,
and
pharmaceutically acceptable salts thereof.

15. A pharmaceutical composition comprising a compound according to claim 1 and a pharmaceutically acceptable carrier and/or adjuvant.

16. A compound according to claim 1, selected from the group consisting of:
5-trifluoromethyl-pyridine-2-carboxylic acid [3-((S)-2-amino-1,4-dimethyl-6-oxo-1,4,5,6-tetrahydro-pyrimidin-4-yl)-phenyl]-amide,
5-methyl-pyridine-2-carboxylic acid [3-((S)-2-amino-1,4-dimethyl-6-oxo-1,4,5,6-tetrahydro-pyrimidin-4-yl)-phenyl]-amide,
pyridine-2-carboxylic acid [3-((S)-2-amino-1,4-dimethyl-6-oxo-1,4,5,6-tetrahydro-pyrimidin-4-yl)-phenyl]-amide,
5-methoxy-pyridine-2-carboxylic acid [3-((S)-2-amino-1,4-dimethyl-6-oxo-1,4,5,6-tetrahydro-pyrimidin-4-yl)-phenyl]-amide,
5-cyano-pyridine-2-carboxylic acid [3-((S)-2-amino-1,4-dimethyl-6-oxo-1,4,5,6-tetrahydro-pyrimidin-4-yl)-phenyl]-amide,
5-hydroxymethyl-pyridine-2-carboxylic acid [3-((S)-2-amino-1,4-dimethyl-6-oxo-1,4,5,6-tetrahydro-pyrimidin-4-yl)-phenyl]-amide,
N-[3-((S)-2-amino-1,4-dimethyl-6-oxo-1,4,5,6-tetrahydro-pyrimidin-4-yl)-phenyl]-4-methyl-benzamide,
N-[3-((S)-2-amino-1,4-dimethyl-6-oxo-1,4,5,6-tetrahydro-pyrimidin-4-yl)-phenyl]-4-chloro-benzamide,
N-[3-((S)-2-amino-1,4-dimethyl-6-oxo-1,4,5,6-tetrahydro-pyrimidin-4-yl)-phenyl]-6-chloro-nicotinamide,
5-chloro-pyrimidine-2-carboxylic acid [3-((S)-2-amino-1,4-dimethyl-6-oxo-1,4,5,6-tetrahydro-pyrimidin-4-yl)-phenyl]-amide,
and pharmaceutically acceptable salts thereof.

17. A compound according to claim 1, selected from the group consisting of:
1-methyl-6-oxo-1,6-dihydro-pyridazine-3-carboxylic acid [3-((S)-2-amino-1,4-dimethyl-6-oxo-1,4,5,6-tetrahydro-pyrimidin-4-yl)-phenyl]-amide,
5-methyl-pyrazine-2-carboxylic acid [3-((S)-2-amino-1,4-dimethyl-6-oxo-1,4,5,6-tetrahydro-pyrimidin-4-yl)-phenyl]-amide,
6-oxo-1,6-dihydro-pyridazine-3-carboxylic acid [3-((S)-2-amino-1,4-dimethyl-6-oxo-1,4,5,6-tetrahydro-pyrimidin-4-yl)-phenyl]-amide,
6-methyl-pyrazine-2-carboxylic acid [3-((S)-2-amino-1,4-dimethyl-6-oxo-1,4,5,6-tetrahydro-pyrimidin-4-yl)-phenyl]-amide,
5-chloro-pyrazine-2-carboxylic acid [3-((S)-2-amino-1,4-dimethyl-6-oxo-1,4,5,6-tetrahydro-pyrimidin-4-yl)-phenyl]-amide,
N-[3-((S)-2-amino-1,4-dimethyl-6-oxo-1,4,5,6-tetrahydro-pyrimidin-4-yl)-phenyl]-isonicotinamide,
5-fluoro-pyridine-2-carboxylic acid [3-((S)-2-amino-1,4-dimethyl-6-oxo-1,4,5,6-tetrahydro-pyrimidin-4-yl)-phenyl]-amide,
3-chloro-pyridine-2-carboxylic acid [3-((S)-2-amino-1,4-dimethyl-6-oxo-1,4,5,6-tetrahydro-pyrimidin-4-yl)-phenyl]-amide, 4-chloro-pyridine-2-carboxylic acid [3-((S)-2-amino-1,4-dimethyl-6-oxo-1,4,5,6-tetrahydro-pyrimidin-4-yl)-phenyl]-amide, 4-methyl-pyridine-2-carboxylic acid [3-((S)-2-amino-1,4-dimethyl-6-oxo-1,4,5,6-tetrahydro-pyrimidin-4-yl)-phenyl]-amide, and pharmaceutically acceptable salts thereof.

18. A compound according to claim 1, selected from the group consisting of:

6-chloro-pyridine-2-carboxylic acid [3-((S)-2-amino-1,4-dimethyl-6-oxo-1,4,5,6-tetrahydro-pyrimidin-4-yl)-phenyl]-amide, 6-methyl-pyridine-2-carboxylic acid [3-((S)-2-amino-1,4-dimethyl-6-oxo-1,4,5,6-tetrahydro-pyrimidin-4-yl)-phenyl]-amide, N-[3-((S)-2-amino-1,4-dimethyl-6-oxo-1,4,5,6-tetrahydro-pyrimidin-4-yl)-phenyl]-nicotinamide, N-[3-((S)-2-amino-1,4-dimethyl-6-oxo-1,4,5,6-tetrahydro-pyrimidin-4-yl)-phenyl]-benzamide; salt with formic acid, 2-methyl-pyrimidine-5-carboxylic acid [3-((S)-2-amino-1,4-dimethyl-6-oxo-1,4,5,6-tetrahydro-pyrimidin-4-yl)-phenyl]-amide, 5-oxo-4,5-dihydro-pyrazine-2-carboxylic acid [3-((S)-2-amino-1,4-dimethyl-6-oxo-1,4,5,6-tetrahydro-pyrimidin-4-yl)-phenyl]-amide, 3-phenyl-pyridine-2-carboxylic acid [3-((S)-2-amino-1,4-dimethyl-6-oxo-1,4,5,6-tetrahydro-pyrimidin-4-yl)-phenyl]-amide, 2-methyl-oxazole-4-carboxylic acid [3-((S)-2-amino-1,4-dimethyl-6-oxo-1,4,5,6-tetrahydro-pyrimidin-4-yl)-phenyl]-amide, 5-chloro-pyridine-2-carboxylic acid [3-((S)-2-amino-4-ethyl-1-methyl-6-oxo-1,4,5,6-tetrahydro-pyrimidin-4-yl)-phenyl]-amide, pyridine-2-carboxylic acid [3-((S)-2-amino-4-ethyl-1-methyl-6-oxo-1,4,5,6-tetrahydro-pyrimidin-4-yl)-phenyl]-amide, and pharmaceutically acceptable salts thereof.

19. A compound according to claim 1, selected from the group consisting of:

5-chloro-thiophene-2-carboxylic acid [3-((S)-2-amino-4-ethyl-1-methyl-6-oxo-1,4,5,6-tetrahydro-pyrimidin-4-yl)-phenyl]-amide, 6-chloro-pyridine-2-carboxylic acid [3-((S)-2-amino-4-ethyl-1-methyl-6-oxo-1,4,5,6-tetrahydro-pyrimidin-4-yl)-phenyl]-amide, 3-chloro-pyridine-2-carboxylic acid [3-((S)-2-amino-4-ethyl-1-methyl-6-oxo-1,4,5,6-tetrahydro-pyrimidin-4-yl)-phenyl]-amide, 5-chloro-pyrimidine-2-carboxylic acid [3-((S)-2-amino-4-ethyl-1-methyl-6-oxo-1,4,5,6-tetrahydro-pyrimidin-4-yl)-phenyl]-amide, 5-chloro-pyridine-2-carboxylic acid [3-((S)-2-amino-1,4-dimethyl-6-oxo-1,4,5,6-tetrahydro-pyrimidin-4-yl)-4-fluoro-phenyl]-amide, 5-chloro-pyrimidine-2-carboxylic acid [3-((S)-2-amino-1,4-dimethyl-6-oxo-1,4,5,6-tetrahydro-pyrimidin-4-yl)-4-fluoro-phenyl]-amide, pyridine-2-carboxylic acid [3-((S)-2-amino-1,4-dimethyl-6-oxo-1,4,5,6-tetrahydro-pyrimidin-4-yl)-4-fluoro-phenyl]-amide, 5-trifluoromethyl-pyridine-2-carboxylic acid [3-((S)-2-amino-1,4-dimethyl-6-oxo-1,4,5,6-tetrahydro-pyrimidin-4-yl)-4-fluoro-phenyl]-amide, 5-chloro-pyridine-2-carboxylic acid [3-((S)-2-amino-1-ethyl-4-methyl-6-oxo-1,4,5,6-tetrahydro-pyrimidin-4-yl)-phenyl]-amide, 5-chloro-pyridine-2-carboxylic acid [3-((S)-2-amino-1-benzyl-4-methyl-6-oxo-1,4,5,6-tetrahydro-pyrimidin-4-yl)-phenyl]-amide, and pharmaceutically acceptable salts thereof.

20. A compound according to claim 1, selected from the group consisting of:

5-chloro-pyridine-2-carboxylic acid [3-((S)-2-amino-4-methyl-6-oxo-1,4,5,6-tetrahydro-pyrimidin-4-yl)-phenyl]-amide, 5-chloro-pyridine-2-carboxylic acid [5-((S)-2-amino-1,4-dimethyl-6-oxo-1,4,5,6-tetrahydro-pyrimidin-4-yl)-pyridin-3-yl]-amide, 5-chloro-pyridine-2-carboxylic acid [3-((S)-2-amino-1,4,5,5-tetramethyl-6-oxo-1,4,5,6-tetrahydro-pyrimidin-4-yl)-4-fluoro-phenyl]-amide, and pharmaceutically acceptable salts thereof.

\* \* \* \* \*